(12) United States Patent
Okubo et al.

(10) Patent No.: US 8,404,803 B2
(45) Date of Patent: Mar. 26, 2013

(54) CANCER-ASSOCIATED ANTIGEN ANALOGUE PEPTIDES AND USES THEREOF

(75) Inventors: Mitsuo Okubo, Saitama (JP); Hiroo Maeda, Saitama (JP); Satoru Takeda, Saitama (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 883 days.

(21) Appl. No.: 11/910,129

(22) PCT Filed: Mar. 31, 2006

(86) PCT No.: PCT/JP2006/306819
§ 371 (c)(1),
(2), (4) Date: Mar. 30, 2009

(87) PCT Pub. No.: WO2006/106912
PCT Pub. Date: Oct. 12, 2006

(65) Prior Publication Data
US 2011/0229481 A1    Sep. 22, 2011

(30) Foreign Application Priority Data

Mar. 31, 2005  (JP) .................................. 2005-105376
Jun. 7, 2005   (JP) .................................. 2005-167589

(51) Int. Cl.
*C07K 5/00* (2006.01)
(52) U.S. Cl. ........ 530/324; 530/325; 530/326; 530/327; 530/328
(58) Field of Classification Search .................... None
See application file for complete search history.

(56) References Cited

U.S. PATENT DOCUMENTS 6,858,710 B2 * 2/2005 Bangur et al. ................. 530/386
2007/0099251 A1 * 5/2007 Zhang et al. .................. 435/7.23

FOREIGN PATENT DOCUMENTS

WO  WO 02/083866     10/2002
WO     02/092836  * 11/2002
WO  WO 02/092836    11/2002

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Gura (Science, 1997, 278:1041-1042).*
Jain (Sci. Am., 1994, 271:58-65).*
Bast et al., "Reactivity of a monoclonal antibody with human ovarian carcinoma", J. Clin. Invest. 68:1331-1337, 1981.
Ikeba et al., "Five year results of cyclic semi-high dose neoadjuvant chemotherapy supported by autologous peripheral blood stem-cell transplantation in patients with advanced ovarian cancer", Int. J. Clin. Oncol. 9(2):113-119, 2004.
Maeda et al., "A new monoclonal antibody (SH-9) recognizes the low molecular mass of ovarian cancer antigen CA125", Acta Obst. Gynaec Jpn. 42(4):320-326, 1990.
Matsuoka et al., "Recognition of ovarian cancer antigen CA125 by murine monoclonal antibody produced by immunization of lung cancer cells", Cancer Research 47:6335-6340, 1987.
Mehrotra et al., "Regulation of melanoma epitope-specific cytolytic T lymphocyte response by immature and activated dendritic cells, in vitro", Cancer Research 63:5607-5614, 2003.
Nozawa et al., "Ovarian cancer", The Journal of the Japan Medical Association 131(5):647-648, 2004.
Okubo et al., "Analysis of HLA-DRB1*0901-binding HPV-16 E7 helper T cell epitope", J. Obstet. Gynaecol. Res. 30(2):120-129, 2004.
Okubo et al., "Dendrick cell therapy", Tuketsugaku (Transfusiology), pp. 948-957, 2004.
Rosenberg et al., "A new approach to the adoptive immunotherapy of cancer with tumor-infiltrating lymphocytes", Science 233:1318-1321, 1986.
Rosenberg et al., "Immunologic and therapeutic evaluation of a synthetic peptide vaccine for the treatment of patients with metastatic melanoma", Nature Medicine 4(3):321-327, 1998.
Sakahara et al., "Effect of circulating antigen on imunoscintigraphy of ovarian cancer patients using anti-CA125 monoclonal antibody", Jpn. J. Cancer Res. 87:655-661, 1996.
Yin et al., "Monoclonal cloning of the CA125 ovarian cancer antigen", The Journal of Biological Chemistry 276(29):27371-27375, 2001.

* cited by examiner

*Primary Examiner* — Sheela J Huff
(74) *Attorney, Agent, or Firm* — Fish & Richardson P.C.

(57) ABSTRACT

First, to solve the problems of the present invention, the present inventors confirmed the presence of ovarian cancer antigen-specific T cells in the peripheral blood of ovarian cancer patients by using an experimental system that detects combinations of CD4 and IL-4 or IFNγ. Next, using analogue peptides of the core protein MUC 16 of the ovarian cancer-associated antigen CA 125, the present inventors revealed that antigen-specific CD4-positive T cells are present at an average frequency of about 4% in the peripheral mononuclear cells of patients and healthy subjects. Then, the present inventors analyzed the epitope for T cells in the core protein MUC 16 of the ovarian cancer-associated antigen CA 125, and determined the amino acid sequence FTLNFTITN (SEQ ID NO: 1) to be a shorter epitope. The present inventors further discovered that the analogue peptide OVCA11: GHTAPG-PLLVPFTLNFTITN (SEQ ID NO:11) is suitable for T cell activation.

11 Claims, 18 Drawing Sheets

| REPEAT 1 | SEQ ID NO |
|---|---|
| LFKSTSVGPLYSGCRLTLLRPKKRKVATRVDTICTLRLDPTGPRLNRQRLYLKLSQLTNSVTELGPYTLDRDSLYVNG | (16) |
| LFKSTSVGPLYSGCRLTLLRPEKDGEATKVDAICTLRLDPLIPGLDRERLYWELSQLTNSVTELGPYTLDRDSLYVNG | (17) |
| LFKSTSVGPLYSGCRLTLLRPEKDGAATGVDAICTLRLDPQGPGLDRERLYWELSQLTNSVTELGPYTLDRDSLYVNG | (18) |
| RVDPIGPGLDRERLYWELSQLTNSITELGPYTLDRDSLYVNG | (19) |
| LFKNTSVGPLYSGCRLTLLRPEKGAATGVDAICTLRLDPTGPGLDRERLYWELSQLTNSVTELGPYTLDRDSLYVNG | (20) |
| LFKNTSVGPLYSGCRLTLLRPEKRGAATGVDTICTLRLDPLNPGLDREQLYWELSKLTRGIIELGPYLLDRGSLYVNG | (21) |
| LFKNTSIGPLYSSGCRLTLLRPEKDKAATRVDAICTHHPDPQSPGLNREQLYWELSQLTHGITELGPYTLDRDSLYVDG | (22) |
| LFKNTSVGPLYSGCRLTLLRPEKGDVATRVDAICTHRPDPKIPGLDRQQLYWELSQLTHWITELGPYTLDRDSLYVNG | (23) |
| LFKNTSVSSLYSGCRLTLLRPEKGAATRVDAVCTHRPDPKSPGLDRERLYWKLSQLTHGITELGPYTLDRHSLYVNG | (24) |
| VFKNTSVGPLYSGCRLTLLRPKKDGAATKVDAICTYRPDPKSPGLDREQLYWELSQLTHSITELGPYTLDRDSLYVNG | (25) |
| LFKNTSVGPLYSGPLTLLRPEKDGTATGVDAICTHHPDPKSPRLDREQLYWELSQLTHNITELGPYALDNDSLFVNG | (26) |
| LFKNTSVGPLYSGSRLTLLRPEKDGEATGVDAICTHRPDPTGPGLDREQLYELSQLTHSITELGPYTLDRDSLYVNG | (27) |

| ANALOGUE PEPTIDE SEQUENCE 1 | |
| LFKSTSVGPLYSGCRLTLLRPEKDGAATGVDAICTLRPDPKSPGLDREQLYWELSQLTHSITELGPYTLDRDSLYVNG | (28) |

FIG. 1

| REPEAT 2 | SEQ ID NO |
|---|---|
| FNPWSFMTTTRIGDVPAMDLATSEIPSSKSRPITTVHLLVLFTLNFTITNLQYMADMGQPGSLKFNTTERVMQGLLKP | (29) |
| FTQQSVSTTSIPVTSIVYLETSRTPPSLPETSAASPLLVPFTLNFTITNLQYEEAMQHPGSRKFNTTERVLQGLLSP | (30) |
| FTHRSSVPTTSIPGTSAVHLETSKTPASLPGHTAPGPLLVPFTLNFTITNLQYEEDMWHPGSRKFNTTERVLQGLLKP | (31) |
| FNPWSSVPTTSTPGTSTVHLATSGTPSSLPGHTAPVPLLIPFTLNFTITNLHYEENMQHPGSRKFNTTERVLQGLLKP | (32) |
| FTHRSSVPTTSIPGTSAVHLETSGTPASLPGHTAPGPLLVPFTLNFTITNLQYEEDMRHPGSRKFNTTERVLQGLLKP | (33) |
| PTHRNFVPITSTPGTSTVHLGTSETPSSLPRPIVPGPLLVPFTLNFTITNLQYEEAMRHPGSRKFNTTERVLQGLLRP | (34) |
| PTHWSPIPTTSTPGTSIVNLGTSGIPPSLPETTATGPLLVPFTLNFTITNLQYEENMGRPGSRKFNITESVLQGLLRP | (35) |
| FTHQSSMTTRTPDTSTMHLATSRTPASLSGPTTASPLLVLFTLNFTITNLRYEENMHHPGSRKFFTTERVLQGLLRP | (36) |
| FTQRSSVPTTSIPGTPTVDLGTSGTPVSKPGPSAASPLLVLFTLNFTITNLRYEENMQHPGSRKFNTTERVLQGLLRS | (37) |
| FTHRSSVSTTSTPGTPTVYLGASKTPASIFGPSAASHLLILFTLNFTITNLRYEENMW-PGSRKFNTTERVLQGLLRP | (38) |
| FTHRSSVPTTSTPGTSTGVVSEE----------PFTLNFTINNLRYMADMGQPGSLKFNITDNVMQHLLSP | (39) |
| ANALOGUE PEPTIDE SEQUENCE 2 | |
| FTHRSSVPTTSTPGTSTVHLGTSGTPASLPGHTAPGPLLVPFTLNFTITNLRYEENMRHPGSRKFNTTERVLQGLLRP | (40) |

FIG. 2

LFQRSSLGARYTGCRVIALRSVKNGAETRVDLLCTYLQPLSGPGLPIKQVFHELSQQTHGITRLGPYSLDKDSLYLNG
YNEPGPDEPPTTPKPATTLPPLSEATTAMGYHLKTLTLNFTISNLQYSPDMGKGSATFNSTEGVLQHLLRPLFQKSS
MGPFYLGCQLISLRPEKDGAATGVDTTCTYHPDPVGPGLDIQQLYWELSQLTHGVTQLGFYVLDRDSLFINGYAPQFL
SIRGEYQINFHIVNWNLSNPDPTSSEYITLLRDIQDKVTTLYKGSQLHDTFRFCLVTNLTMDSVLVTVKALFSSNLDP
SLVEQVFLDKTLFASFHWLGSTYQLVDIHVTEMESSVYQPGSSSSTQHFYPNFITTNLPYSQDKAQPGTTNYQRNKRN
IEDALNQLFRNSSIKSYFSDCQVSTFRSVPNRHHTGVDSLCNFSPLARRVDRVAIYEEFLRMTRNGTQLQNFTLDRSS
VLVDGYSPNRNEPLTGNSDLPFWAVILIGLAGLLGLITCLICGVLVTTRRRKKEGEYNVQQCPGYYQSHLDLEDLQ
(SEQ ID NO: 41)

FIG. 3

ANALOGUE PEPTIDE
PTHRSSVPTTSTPGTSTVHLGTSGTPASLPGHTAPGPLLVPFTLNFTITNLRYEENMRHPGSRKFNTTERVLQGLLRP (SEQ ID NO: 40)

SCREENED SYNTHETIC ANALOGUE PEPTIDE SERIES OF 20 AMINO ACID RESIDUES

PTHRSSVPTTSTPGTSTVHL: OVCA 8 (SEQ ID NO: 42)
STPGTSTVHLGTSGTPASLP: OVCA 9 (SEQ ID NO: 14)
GTSGTPASLPGHTAPGPLLV: OVCA 10 (SEQ ID NO: 13)
GHTAPGPLLVPFTLNFTITN: OVCA 11 (SEQ ID NO: 11)
PFTLNFTITNLRYEENMRHP: OVCA 12 (SEQ ID NO: 12)
LRYEENMRHPGSRKFNTTER: OVCA 13 (SEQ ID NO: 15)
GSRKFNTTERVLQGLLRP: OVCA 14 (SEQ ID NO: 43)

FIG. 4

| ID | SEQUENCE | MW | pI | HYDROPHILICITY | SEQ ID NO |
|---|---|---|---|---|---|
| OVCA10 | GTSGTPASLPGHTAPGPLLV | 1830.03 | 7.90 | 30% | 13 |
| OVCA11 | GHTAPGPLLVPFTLNPTITN | 2110.38 | 7.90 | 35% | 11 |
| OVCA12 | PFTLNFTITNLRYEENMRHP | 1867.99 | 7.60 | 50% | 12 |
| OVCA107 | PFTLNFTITN | 1167.29 | 6.34 | 50% | 2 |
| OVCA108 | LFTLNFTITN | 1183.34 | 5.94 | 50% | 3 |
| OVCA101 | GHTAPVPLLI | 1017.22 | 7.90 | 20% | 4 |
| OVCA102 | GHTAPGPLLV | 961.11 | 7.90 | 20% | 5 |
| OVCA103 | RPIVPGPLLV | 1060.33 | 10.75 | 10% | 6 |
| OVCA104 | ETTATGPLLV | 1001.12 | 3.30 | 40% | 7 |
| OVCA105 | GPTTASPLLV | 955.10 | 6.04 | 30% | 8 |
| OVCA106 | GPSAASPLLV | 911.06 | 6.04 | 20% | 9 |
| OVCA115 | LRYEENMRHP | 1344.50 | 7.78 | 70% | 10 |

FIG. 5

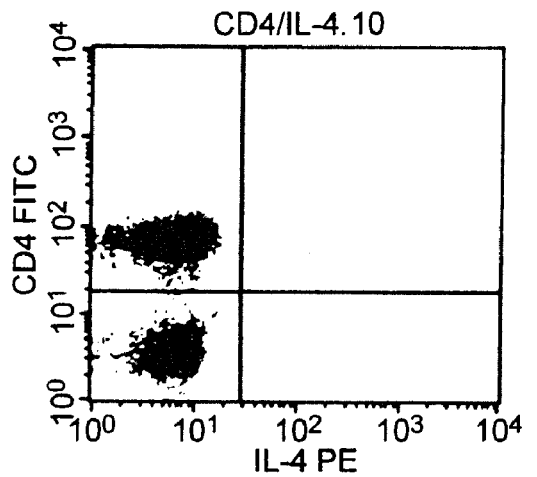
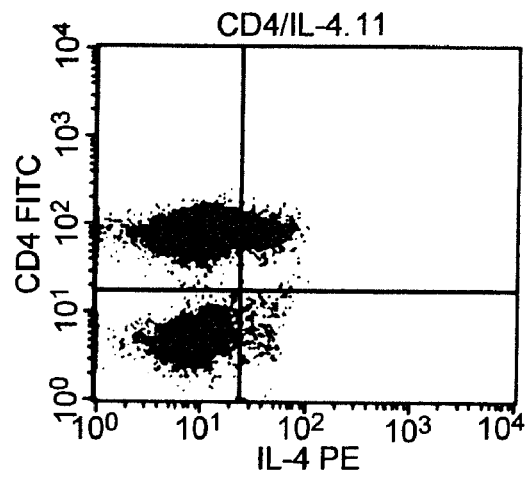
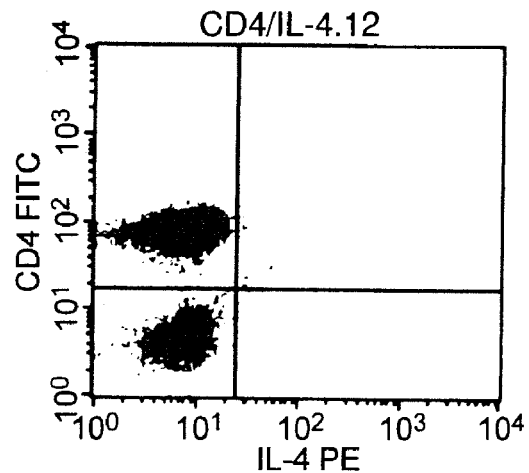
FIG. 7

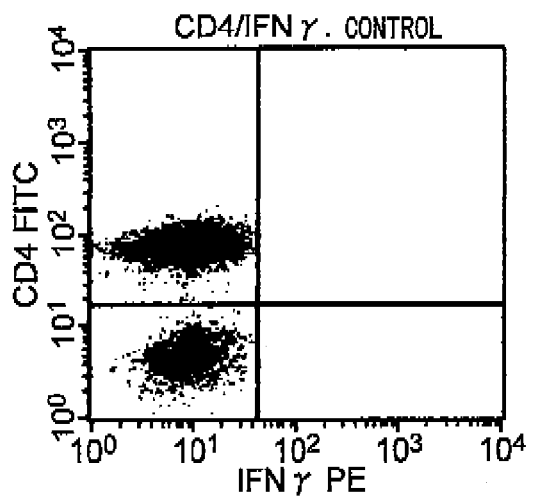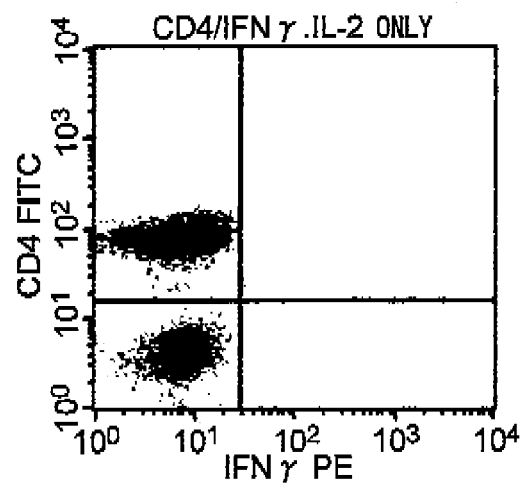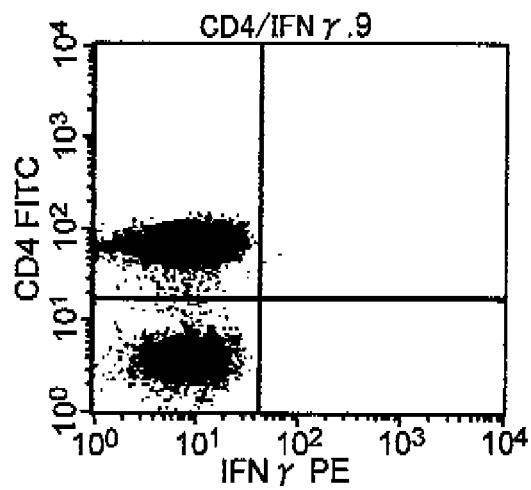
FIG. 9

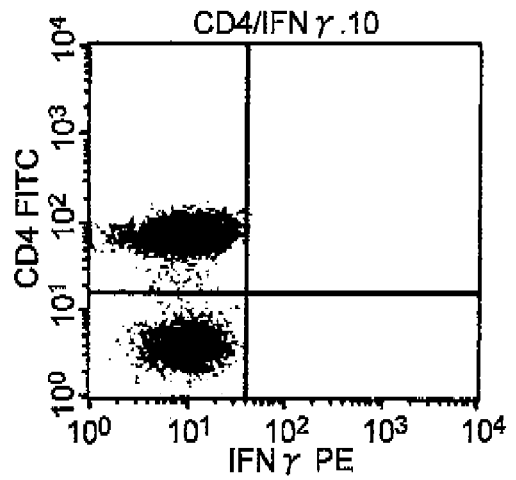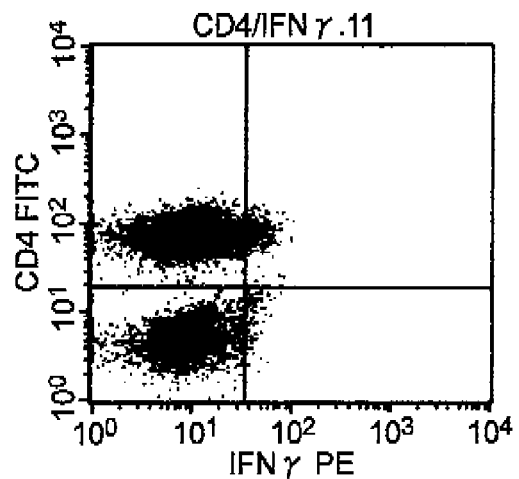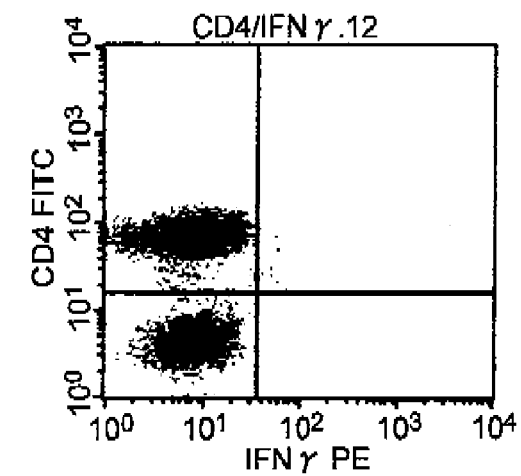
FIG. 10

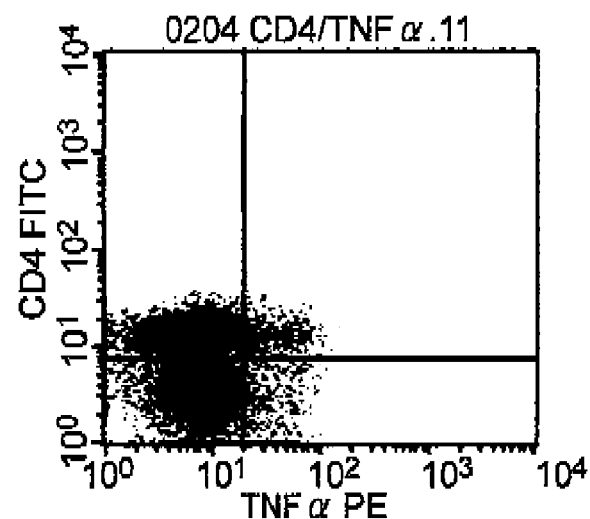
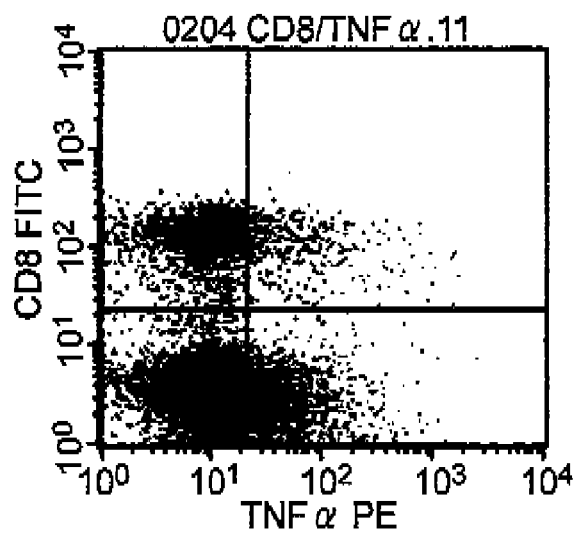
FIG. 12

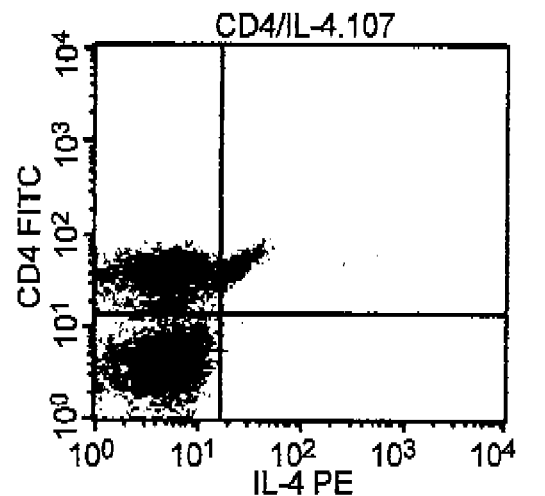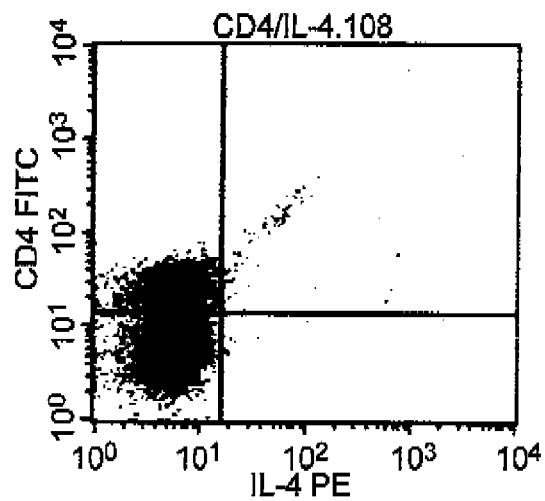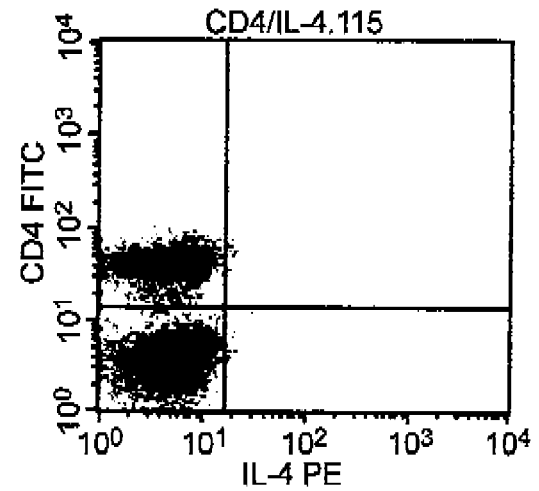
FIG. 13

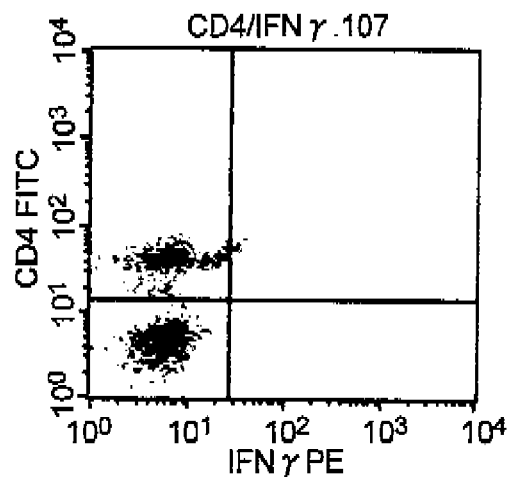
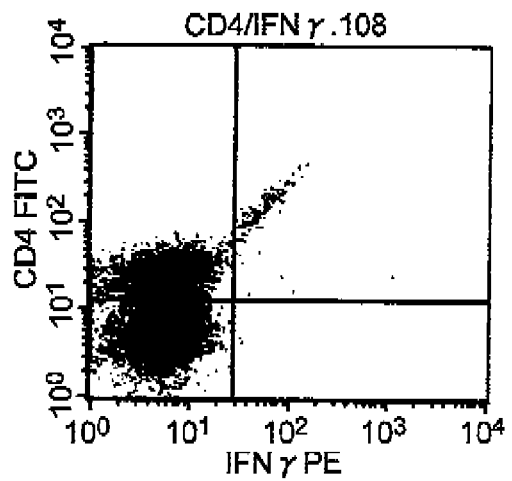
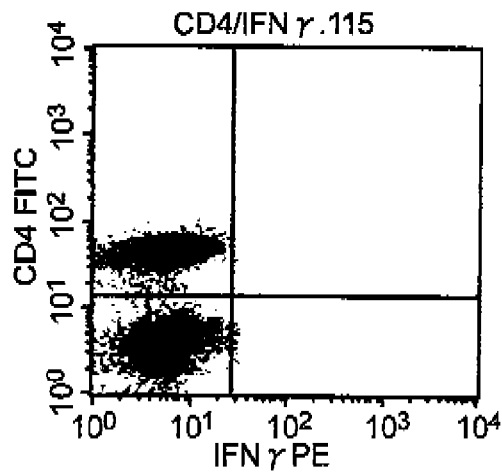
FIG. 15

CANCER-ASSOCIATED ANTIGEN ANALOGUE PEPTIDES AND USES THEREOF

CROSS-REFERENCE TO RELATED APPLICATIONS

This application is the National Stage of International Application No. PCT/JP2006/306819, filed on Mar. 31, 2006, which claims the benefit of Japanese Patent Applications Ser. No. 2005/105376, filed on Mar. 31, 2005, and Ser. No. 2005/167589, filed on Jun. 7, 2005. The contents of all of the foregoing applications are hereby incorporated by reference in their entireties.

TECHNICAL FIELD

The present invention relates to cancer-associated antigen analogue peptides and uses thereof.

BACKGROUND ART

In Japan, the number of ovarian cancer patients is increasing year by year; the National Cancer Center (Japan) reports that 6742 people developed ovarian cancer in 1998, with annual fatalities also increasing to 4154 people in 2001. Advanced ovarian cancer at stages III-IV of the disease classification, is difficult to treat by surgery alone, and chemotherapy using anti-cancer agents is often performed. However, the prognosis for advanced ovarian cancer is poor, and figures from the National Cancer Center (Japan) for the year 2000 suggest the five-year survival rate for stage III ovarian cancer is 30%, while that of stage IV is as low as 12%. The development of novel therapeutic methods has thus been long awaited.

"Cell therapy" uses the cellular immune reactions of a living body based on scientific grounds (a point which distinguishes it from folk medicine using cells), and is a cancer therapy method that supplements surgery and chemotherapy (Non-Patent Document 1). One well-known example of "cell therapy" is "lymphocyte activated killer (LAK) therapy: adoptive immunotherapy", developed by Rosenberg et al. in the 1980s (Non-Patent Document 2). In this method, blood comprising natural killer cells (NK cells) and T cells of a patient's blood is cultured in vitro, then the blood is returned into the veins of that same patient. For certain kinds of advanced cancer, adoptive immunotherapy has a definite effect; however, whether or not this therapeutic method achieves its tumor-reducing effect via a cancer antigen-specific immune reaction has been unclear, since the method does not limit the type of cancer cells. Therefore, for cellular therapies targeting malignant melanomas, a method wherein antigen-specific CD8-positive cytotoxic T cells are activated in vitro using peptides synthesized based on amino acid sequences of cancer antigens and returned to the body were selected and showed some effect. This method was beneficial in that it demonstrated that therapeutic strategies in which peptide-stimulated T cells reduce tumors in an antigen-specific manner were possible (Non-Patent Document 3).

However, there are several problems when it comes to applying this therapeutic method to other cancers, and the method has not yet been put to practical use. The following three problems have been mentioned: (1) time and labor are required in the conventional methods to determine cancer tumor-rejection antigens for each organ, and this is not easy; (2) it takes time to culture and obtain the necessary number of T cells; and (3) there is a high possibility that CD8-positive cytotoxic T cells by themselves have an established immunological tolerance (herein after called 'tolerance') to the cancer tumor-rejection antigen (Non-Patent Document 4).

[Non-Patent Document 1] Mitsuo Okubo, Cell therapy, pp. 948-957, Transfusion science revised 3rd edition, Hiroshi Tohyama et al., Chugai Igaku, Tokyo, 2004.

[Non-Patent Document 2] Rosenberg S A, Spiess P, Lafreiere R: A new approach to the adoptive immunotherapy of cancer with tumor-infiltrating lymphocyte. Science. 233: 1318-21, 1986.

[Non-Patent Document 3] Rosenberg S A, Yang J C, Schwartzentruber D J, et al.: Immunologic and therapeutic evaluation of a synthetic peptide vaccine for the treatment of patients with metastatic melanoma. Nature Med. 4:321-327, 1998.

[Non-Patent Document 4] Mehrotra S, Stevens R, Zengou R, et al: Regulation of melanoma epitope-specific cytolytic T lymphocyte response by immature and activated dendritic cells, in vitro. Cancer Research. 63:5607-5614, 2003.

DISCLOSURE OF THE INVENTION

Problems to be Solved by the Invention

Advanced ovarian cancer is treated by surgery and chemotherapy with anti-cancer agents; however, the prognosis when conventionally treated is poor and the development of new therapeutic methods has been desired. "Cancer antigen-specific cellular therapies", that is, therapeutic methods which use cancer-associated antigen analogue peptides and T cells activated by these peptides, did not exist to date for ovarian cancer treatments.

The present invention was accomplished in view of the above-mentioned situation. An objective of the invention is to provide ovarian cancer-associated antigen analogue peptides comprising the amino acid sequence Phe-Thr-Leu-Asn-Phe-Thr-Ile-Thr-Asn (SEQ ID NO: 1). A further objective of the invention is to provide T cells that are activated by the administration of such peptides or antibodies binding to these peptides. Moreover, another objective of the invention is to provide methods for preventing or treating cancer diseases and such by using these peptides, these T cells, or these antibodies. A further objective of the invention is to provide agents for preventing or treating cancer diseases and such, where the active ingredients of the agents are these peptides, these antibodies, or these T cells.

Means for Solving the Problems

To solve the above problems, the present inventors planned a novel T cell treatment protocol for treating cancer diseases, which supplements chemotherapy. In this plan, following chemotherapy using anti-cancer agents, autologous T cells stimulated with cancer-associated antigen peptide analogues are returned into the body to induce anti-tumor effects.

First, the present inventors confirmed that T cell therapy can be performed after chemotherapy with anti-cancer agents by analyzing cellular fractions comprised in the blood samples of patients after chemotherapy with anti-cancer agents and by confirming that the numbers of T cells and B cells were within a normal range, while the numbers of CD4-positive memory cells and monocytes were increased. Next, the presence of ovarian cancer antigen-specific T cells in the peripheral blood of ovarian cancer patients was confirmed using an experimental system that detects CD4 and IL-4 or IFNγ in combination. The present inventors analyzed antigen-specific CD4-positive T cells in the body of patients and healthy individuals using analogue peptides of the core protein MUC16 of the ovarian cancer-associated antigen CA125.

The results of the above analysis revealed for the first time that T cells recognizing a specific amino acid sequence (analogue peptide) of the ovarian cancer antigen were present among the peripheral mononuclear cells of patients at an average frequency of about 4%.

Further, the present inventors performed T cell epitope analysis on the core protein MUC16 of the ovarian cancer-associated antigen CA125, thus determining the amino acid sequence FTLNFTITN (SEQ ID NO: 1) as a much shorter epitope, and hence discovering that the analogue peptide OVCA11: GHTAPGPLLVPFTLNFTITN (SEQ ID NO: 11), which comprises this epitope, is more suitable for activating T cells.

In a previous report, the present inventors used synthetic peptides of cervical cancer-associated antigens to determine an epitope recognized by a patient's helper T cells (Okubo M, Saito M, Inoku H, et al., Analysis of HLA-DRB*0901-binding HPV-16 E7 helper T cell epitope, J Obstet Gynaecol Res. 30: 120-129, 2004). They further succeeded in inducing Th1-type T cells that, although being CD4-positive, have cytotoxic activity by culturing peripheral blood mononuclear cells with IL-12 in vitro when stimulating them with this synthetic peptide (WO 2002/100889).

In ovarian cancer, which is the subject of the present invention, CD4-positive Th1-type T cells could be increased in a patients mononuclear cell samples through stimulation with analogue peptides in the absence of IL-12. Moreover, CD4-positive TNFα-producing T cells and CD8-positive TNFα-producing T cells could also be induced. Therefore, it is considered that anti-tumor effects can be exerted through antigen-specific immune reactions, such as direct damage to CA125-producing cells, supplementation of CD8-positive cells, and specific antibody production, by stimulating these cells with the analogue peptide to antigen-specifically reactivate memory T cells, and then introducing these into the peritoneal cavity (ascites), peripheral blood vessels, or lymph vessels of the patient. In particular, in cases where recurrence is feared even though tumor cells have almost completely been removed by surgery, the cancer antigen analogue peptides can be administered to reactivate memory T cells and suppress recurrence; thus the treatment is being effective as a treatment that improves long-term prognosis.

Specifically, the present inventors specified the epitopes of ovarian cancer-associated antigens, and discovered that cancer-associated antigen analogue peptides comprising these epitopes activate T cells. They further succeeded in inducing an anti-tumor effect by returning autologous T cells to the body after activating them with these cancer-associated antigen analogue peptides, following chemotherapy with anti-cancer agents; and thus they completed the present invention.

More specifically, the present invention provides (1) to (30) described below:

(1) a peptide comprising the formula below:

X1-X2-X3-X4-X5-X6

(wherein X1, X2, X3, X5, and X6 represent an optional amino acid residue or optional amino acid sequence, and X4 is Phe-Thr-Leu-Asn-Phe-Thr-Ile-Thr-Asn (SEQ ID NO: 1));
(2) the peptide of (1), wherein X3 is Pro or Leu;
(3) the peptide of (1) or (2), wherein X2 is any one of:

Gly-His-Thr-Ala-Pro-Val-Pro-Leu-Leu-Ile, (SEQ ID NO: 4)

Gly-His-Thr-Ala-Pro-Gly-Pro-Leu-Leu-Val, (SEQ ID NO: 5)

Arg-Pro-Ile-Val-Pro-Gly-Pro-Leu-Leu-Val, (SEQ ID NO: 6)

Glu-Thr-Thr-Ala-Thr-Gly-Pro-Leu-Leu-Val, (SEQ ID NO: 7)

Gly-Pro-Thr-Thr-Ala-Ser-Pro-Leu-Leu-Val, (SEQ ID NO: 8)

Gly-Pro-Ser-Ala-Ala-Ser-Pro-Leu-Leu-Val, (SEQ ID NO: 9)
and

Gly-Thr-Ser-Gly-Thr-Pro-Ala-Ser-Leu-Pro-Gly-His-Thr-Ala-Pro-Gly-Pro-Leu-Leu-Val; (SEQ ID NO: 13)

(4) the peptide of (1) or (2), wherein X2 is any one of:

Ala-Pro-Val-Pro-Leu-Leu-Ile, (SEQ ID NO: 46)

Ala-Pro-Gly-Pro-Leu-Leu-Val, (SEQ ID NO: 47)

Ala-Ser-Pro-Leu-Leu-Val, (SEQ ID NO: 48)

Gly-Pro-Leu-Leu-Val, (SEQ ID NO: 49)
and

Pro-Leu-Leu-Val; (SEQ ID NO: 50)

(5) the peptide of any one of (1) to (4), wherein X5 is Leu-Arg-Tyr-Glu-Glu-Asn-Met-Arg-His-Pro (SEQ ID NO: 10);
(6) the peptide of any one of (1) to (5), which comprises 30 or fewer amino acid residues;
(7) the peptide of any one of (1) to (6), which is derived from the core protein MUC16 of ovarian cancer-associated antigen CA125;
(8) a DNA encoding the peptide of any one of (1) to (7);
(9) a vector comprising the DNA of (8);
(10) a transformant into which the vector of (9) has been introduced;
(11) a method for producing the peptide of any one of (1) to (8), wherein the method comprises the step of culturing or developing the transformant of (10), and recovering a recombinant protein from the cell or its culture supernatant;
(12) an antibody that binds to the peptide of any one of (1) to (7);
(13) the antibody of (12), which is a monoclonal antibody;
(14) a method for detecting in a subject a cancer cell, a cancer cell-associated antigen, or an endometrial cell that developed at a site other than the inside of a uterus, wherein the method comprises the step of administering the antibody of (12) or (13) to the subject;.
(15) a method for activating a T cell in a subject, wherein the method comprises the step of administering the peptide of any one of (1) to (7) to the subject;
(16) the method of (15), wherein the T cell is an IL-4-producing human CD4-positive T cell, IFNγ-producing human CD4-positive T cell, TNFα-producing human CD4-positive T cell, or TNFα-producing human CD8-positive T cell;
(17) a T cell activated by the method of (15) or (16);
(18) a method for preventing or treating a cancer disease or an endometriosis in a subject, wherein the method comprises the step of administering the peptide of any one of (1) to (7) to the subject;
(19) a method for preventing or treating a cancer disease or an endometriosis in a subject, wherein the method comprises the step of administering the antibody of (12) or (13) to the subject;

(20) a method for preventing or treating a cancer disease or an endometriosis in a subject, wherein the method comprises the steps (a) to (c) below:
(a) adding the peptide of any one of (1) to (7) to a T cell;
(b) culturing the T cell of (a); and
(c) administering the T cell obtained in (b) to a subject;
(21) the method of (20), wherein the method comprises the step of performing chemotherapy with an anti-cancer agent to a subject prior to step (a);
(22) the method of (21), wherein the chemotherapy with the anti-cancer agent is chemotherapy combined with autologous peripheral blood stem cell transplantation;
(23) the method of any one of (18) to (22), wherein the cancer disease is ovarian cancer, pancreatic cancer, or lung cancer;
(24) the method of any one of (18) to (22), wherein the endometriosis is adenomyosis uteri;
(25) an agent for preventing or treating a cancer disease or an endometriosis, which comprises the peptide of any one of (1) to (7) as an active ingredient;
(26) an agent for preventing or treating a cancer disease or an endometriosis, which comprises the antibody of (12) or (13) as an active ingredient;
(27) an agent for preventing or treating a cancer disease or an endometriosis, which comprises the T cell of (17) as an active ingredient;
(28) the agent of any one of (25) to (27), wherein the cancer disease is ovarian cancer, pancreatic cancer, or lung cancer;
(29) the agent of any one of (25) to (27), wherein the endometriosis is adenomyosis uteri; and
(30) a cancer tumor marker, an antibody for immunostaining, or an endometrial cell marker that comprises the antibody of (12) or (13) as an active ingredient.

BRIEF DESCRIPTION OF THE DRAWINGS

FIG. 1 shows the amino acid sequence of MUC16 of CA125. "Repeat 1" and "analogue peptide sequence 1" are shown. Different amino acid sequences from among the 12 repeat sequences were substituted with common amino acids to design the novel "analogue peptide sequence 1". This sequence was divided into fragments of 20 amino acid residues each, and synthetic peptides were prepared.

FIG. 2 shows the amino acid sequence of MUC16 of CA125. "Repeat 2" and "analogue peptide sequence 2" are shown. The different amino acid sequences from among the 11 repeat sequences were substituted with common amino acids to design the novel "analogue peptide sequence 2". This sequence was divided into fragments of 20 amino acid residues each, and synthetic peptides were prepared.

FIG. 3 shows the amino acid sequence of MUC16 of CA125. An amino acid sequence without repeats is shown. This sequence was divided into fragments of 20 amino acid residues each, and synthetic peptides were prepared.

FIG. 4 shows a series of the 20 amino acid residue synthetic analogue peptides derived from the "analogue peptide sequence 2" of MUC16. "Analogue peptide sequence 2", which showed a positive reaction in preliminary experiments, was prepared as a series of 20 amino acid residue synthetic analogue peptides OVCA8-14, in which the peptides each overlap by 10 amino acid residues with each other.

FIG. 5 shows the peptide sequences of ten amino acid residues for determining the epitope for the T cells. Peptides OVCA101-115 are shown, which are the original sequences (original MUC16) for the analogue peptides OVCA 11 and OVCA12 for which a positive reaction was obtained.

FIG. 7 shows examples of the results of flow cytometry analysis detecting CD4 and IL-4. Upper panel: mononuclear cell sample to which IL-2 and analogue peptide OVCA10 were added. Middle panel: mononuclear cell sample to which IL-2 and analogue peptide OVCA11 were added. Lower panel: mononuclear cell sample to which IL-2 and analogue peptide OVCA12 were added. The mononuclear cell sample to which analogue peptide OVCA11 had been added comprised 7.06% CD4-positive/IL-4 positive T cells.

FIG. 9 shows examples of the results of flow cytometry analysis detecting CD4 and IFNγ. Upper panel: background without addition of IL-2 or analogue peptide. Middle panel: control to which IL-2 but not analogue peptide was added. Lower panel: mononuclear cell sample to which IL-2 and analogue peptide OVCA9 were added. The frequencies of CD4-positive/IFNγ-positive T cells in the three mononuclear cell samples were 0.02%, 0.08% and, 0.02% respectively; thus, such T cells were hardly detected.

FIG. 10 shows examples of the results of flow cytometry analysis detecting CD4 and IFNγ. Upper panel: sample to which IL-2 and analogue peptide OVCA10 were added. Middle panel: sample to which IL-2 and analogue peptide OVCA11 were added. Lower panel: sample to which IL-2 and analogue peptide OVCA12 were added. The sample to which analogue peptide OVCA11 had been added comprised 3.12% CD-4-positive/IFNγ-positive T cells.

FIG. 12 shows examples of the results of flow cytometry analysis detecting CD4 and TNFα, and CD8 and TNFα. Upper panel: sample to which IL-2 and analogue peptide OVCA11 were added. Lower panel: sample to which IL-2 and analogue peptide OVCA11 were added. The sample to which analogue peptide OVCA11 was added comprised 5.76% CD4-positive/TNFα-positive T cells and 3.98% CD8-positive/TNFα-positive T cells.

FIG. 13 shows examples of the results of flow cytometry analysis detecting CD4 and IL-4 at the time of epitope determination. Upper panel: mononuclear cell sample to which IL-2 and analogue peptide OVCA107 were added. Middle panel: mononuclear cell sample to which IL-2 and analogue peptide OVCA108 were added. Lower panel: mononuclear cell sample to which IL-2 and analogue peptide OVCA115 were added. The mononuclear cell samples to which either analogue peptide OVCA107 or OVCA108 had been added comprised CD4-positive/IL-4-positive T cells at 6.32% and 1.17%, respectively.

FIG. 15 shows examples of the results of flow cytometry analysis detecting CD4 and IFNγ at the time of epitope determination. Upper panel: mononuclear cell sample to which IL-2 and analogue peptide OVCA107 were added. Middle panel: mononuclear cell sample to which IL-2 and analogue peptide OVCA108 were added. Lower panel: mononuclear cell sample to which IL-2 and analogue peptide OVCA115 were added. The mononuclear cell samples to which either analogue peptide OVCA107 or OVCA108 were added comprised CD4-positive/IFNγ-positive T cells at 2.10% and 1.27%, respectively.

BEST MODE FOR CARRYING OUT THE INVENTION

Figure 6:
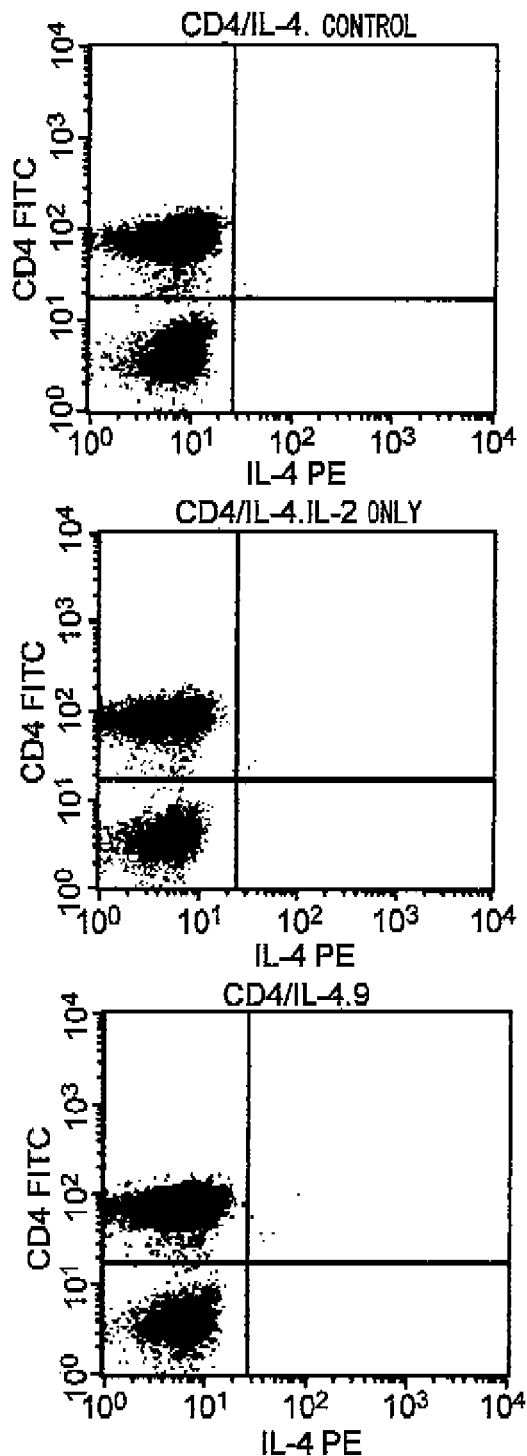
FIG. 6 shows examples of the results of flow cytometry analysis detecting CD4 and IL-4. Upper panel: background without addition of IL-2 or analogue peptide. Middle panel: control to which IL-2 but not analogue peptide was added. Lower panel: mononuclear cell sample to which IL-2 and analogue peptide OVCA9 were added. The frequencies of CD4-positive/IL-4positive T cells in the three mononuclear cell samples were 0.04%, 0% and 0.05% respectively; thus, such T cells were hardly detected.

The present invention relates to peptides comprising the amino acid sequence Phe-Thr-Leu-Asn-Phe-Thr-Ile-Thr-Asn (SEQ ID NO: 1). The amino acid sequences of other portions of the peptides of the present invention are not particularly limited, so long as the peptides comprise the amino acid sequence Phe-Thr-Leu-Asn-Phe-Thr-Ile-Thr-Asn (SEQ ID NO: 1).

In one embodiment of the peptides of the present invention, peptides comprising the following formula are preferable examples:

X1-X2-X3-X4-X5-X6

In the formula, X4 is Phe-Thr-Leu-Asn-Phe-Thr-Ile-Thr-Asn (SEQ ID NO: 1) and X1, X2, X3, X5 and X6 are amino acid residues or amino acid sequences that may be optionally included; the amino acid sequence constitution is not particularly limited, so long as the peptides are functionally equivalent to the peptides of the present invention.

Herein, "functionally equivalent" means that the subject peptides have a similar immunogenicity to the peptides of the present invention. Examples of immunogenicity in the present invention include T cell activation, enhancement of antibody producing ability, and so on.

The amino acid residue corresponding to X3 of the above formula can be Pro or Leu, but is not limited thereto.

Furthermore, the amino acid sequence corresponding to X2 of the above formula includes, without limitation, any one of Gly-His-Thr-Ala-Pro-Val-Pro-Leu-Leu-Ile (SEQ ID NO: 4), Gly-His-Thr-Ala-Pro-Gly-Pro-Leu-Leu-Val (SEQ ID NO: 5), Arg-Pro-Ile-Val-Pro-Gly-Pro-Leu-Leu-Val (SEQ ID NO: 6), Glu-Thr-Thr-Ala-Thr-Gly-Pro-Leu-Leu-Val (SEQ ID NO: 7), Gly-Pro-Thr-Thr-Ala-Ser-Pro-Leu-Leu-Val (SEQ ID NO: 8), Gly-Pro-Ser-Ala-Ala-Ser-Pro-Leu-Leu-Val (SEQ ID NO: 9), or Gly-Thr-Ser-Gly-Thr-Pro-Ala-Ser-Leu-Pro-Gly-His-Thr-Ala-Pro-Gly-Pro-Leu-Leu-Val (SEQ ID NO: 13).

Moreover, the amino acid sequence corresponding to X2 of the above formula includes any one of Ala-Pro-Val-Pro-Leu-Leu-Ile (SEQ ID NO: 46), Ala-Pro-Gly-Pro-Leu-Leu-Val (SEQ ID NO: 47), Ala-Ser-Pro-Leu-Leu-Val (SEQ ID NO: 48), Gly-Pro-Leu-Leu-Val (SEQ ID NO: 49), or Pro-Leu-Leu-Val (SEQ ID NO: 50), without limitation.

In addition, the amino acid sequence corresponding to X5 of the above formula includes Leu-Arg-Tyr-Glu-Glu-Asn-Met-Arg-His-Pro (SEQ ID NO: 10), but is not limited thereto.

The number of the amino acid residues of the peptides of the present invention is not particularly limited; however, it is preferably 30 amino acid residues or less (more specifically, 30, 25, 20, 15, 10 or less).

The origin of the peptides of the present invention is not particularly limited; however, peptides derived from cancer-associated antigens, more preferably, peptides derived from the core protein MUC16 of the ovarian cancer-associated antigen CA125, can be mentioned as preferable examples of the peptides of the present invention.

The present invention relates to DNAs encoding the above-mentioned peptides of the present invention. The DNAs encoding the peptides of the present invention include genomic DNAs, cDNAs, and chemically synthesized DNAs. Genomic DNAs and cDNAs can be prepared by methods conventional to those skilled in the art. For example, genomic DNAs can be prepared by extracting genomic DNAs from cancer-associated antigens (preferably ovarian cancer antigens), preparing genomic libraries (plasmids, phages, cosmids, BAC, PAC and such may be used as the vectors), developing the libraries, and then performing colony hybridization or plaque hybridization using probes prepared based on the DNAs encoding the peptides of the present invention. Genomic DNAs can also be prepared by producing primers specific to the DNAs encoding the peptides of the present invention, and then performing PCR using the primers. Moreover, for example, cDNAs can be prepared by synthesizing cDNAs based on mRNAs extracted from cancer-associated antigens (preferably ovarian cancer antigens), inserting the cDNAs into vectors such as λZAP to produce cDNA libraries, developing the libraries, and then performing colony hybridization or plaque hybridization, or alternatively, performing PCR, similarly to the above.

The DNAs of the present invention can be used, for example, for the large-scale expression of epitopes of cancer-associated antigens, or the large-scale preparation of recombinant peptides.

The present invention relates to vectors comprising these DNAs, and transformants (host cells) into which these vectors have been introduced. The present invention also relates to methods for producing these peptides, which comprise the steps of culturing or developing the transformants and recovering recombinant proteins from the cells or culture supernatants thereof.

The vectors of the present invention are useful for retaining the DNAs of the present invention in host cells and for expressing the proteins of the present invention.

When E. coli is used as a host cell, there is no limitation other than that the vector should have an "ori" to amplify in large amount and mass-produce the vector in E. coli (e.g., JM109, DH5α, HB101, XL1Blue, and such) and a marker gene for selecting the transformed E. coli (e.g., a drug-resistance gene that allows to select using a drug, such as ampicillin, tetracycline, kanamycin, or chloramphenicol).

For example, M13-series vectors, pUC-series vectors, pBR322, pBluescript, pCR-Script, and such can be used. Besides the above vectors, pGEM-T, pDIRECT, pT7, and such can also be used for subcloning and excision of the cDNAs.

When vectors are used to produce the proteins of the present invention, expression vectors are especially useful. When the expression vectors are expressed, for example, in *E. coli*, they should comprise the above characteristics in order to be amplified in *E. coli*. Additionally, when *E. coli* such as JM109, DH5α, HB101, or XL1-Blue are used as host cells, the vectors should have promoters that allow efficient expression in *E. coli*, e.g. lacZ promoter, araB promoter, or T7 promoter. Other examples of the vectors include pGEX-5X-1 (Pharmacia), "QIAexpress system" (QIAGEN), pEGFP, and pET (for this vector, BL21, a strain expressing T7 RNA polymerase, is preferably used as the host).

Furthermore, the vectors may comprise signal sequences for protein secretion. When producing proteins in to the periplasm of *E. coli*, the pelB signal sequence may be used as a signal sequence for protein secretion. For example, calcium chloride methods or electroporation may be used to introduce the vectors into host cells.

In addition to using *E. coli*, the proteins of the present invention may also be produced using, for example, expression vectors derived from mammals (e.g., pCDNA3 (Invitrogen), pEGF-BOS, pEF, pCDM8); insect cells (e.g., "Bac-to-BAC baculovirus expression system" (GIBCO-BRL), pBacPAK8); plants (e.g. pMH1, pMH2); animal viruses (e.g., pHSV, pMV, pAdexLcw); retroviruses (e.g. pZIPneo); yeasts (e.g., "*Pichia* Expression Kit" (Invitrogen), pNV11, SP-Q01); and *Bacillus subtilis* (e.g. pPL608, pKTH50).

In order to express proteins in animal cells, such as CHO, COS, and NIH3T3 cells, the vectors must comprise a promoter necessary for expression in such cells (e.g., SV40 promoter, MMLV-LTR promoter, EF1α promoter, and CMV promoter). The vectors also preferably comprise marker genes for selecting transformants. Examples of vectors with such characteristics include pMAM, pDR2, pBK-RSV, pBK-CMV, pOPRSV, pOP13, and such.

Furthermore, when aiming to stably express a gene and to amplify its copy number in cells, methods can be used that, for example, introduce CHO cells defective in a nucleic acid synthesis pathway with a vector (such as pCHOI) carrying a DHFR gene that compensates for the defect, and then amplify the vector with methotrexate (MTX). Alternatively, when aiming for transient gene expression, examples of methods include those in which COS cells that comprise a gene expressing the SV40 T antigen in the chromosome are transformed with a vector (such as pcD) carrying an SV40 replication origin. The replication origin may be that of a polyomavirus, adenovirus, bovine papilloma virus (BPV), or the like. Also, to amplify the gene copy number in the host cells, selection markers, such as the aminoglycoside transferase (APH) gene, thymidine kinase (TK) gene, *E. coli* xanthine-guanine phosphoribosyl transferase (Ecogpt) gene, and the dihydrofolate reductase (dhfr) gene, may be comprised in the expression vector.

The DNAs of the present invention can be expressed in animals by, for example, inserting DNAs of the invention into appropriate vectors and introducing these vectors into living cells via retroviral methods, liposome methods, cationic liposome methods, adenovirus methods, and such.

The host cells into which vectors of the present invention are introduced are not particularly limited. For example, *E. coli* and various animal cells can be used. The host cells of the present invention can be used, for example, as production systems for producing and expressing the proteins of the present invention. The systems for producing the proteins comprise in vitro and in vivo systems. Production systems that use eukaryotic cells or prokaryotic cells are examples of in vitro production systems.

Eukaryotic host cells that can be used are, for example, animal cells, plant cells, and fungi cells. Mammalian cells, for example, CHO, COS, 3T3, myeloma, BHK (baby hamster kidney), HeLa, Vero, amphibian cells (e.g., *Xenopus oocytes*), and insect cells (e.g. Sf9, Sf21, Tn5) are known as animal cells. Among CHO cells, those defective in the DHFR gene, dhfr-CHO and CEO K-1, are particularly preferable. Of the animal cells, CHO cells are particularly preferable for large-scale expression. Vectors can be introduced into host cells by, for example, calcium phosphate methods, DEAE-dextran methods, methods using cationic liposome DOTAP (Boehringer-Mannheim), electroporation methods, and lipofection methods.

As plant cells, cells originating for example from *Nicotiana tabacum* are known as protein-producing systems and may be used as callus cultures. As fungal cells, yeast such as *Saccharomyces*, including *Saccharomyces cerevisiae*, or filamentous fungi such as *Aspergillus*, including *Aspergillus niger*, are known.

In the case prokaryotic cells are used, production systems which use bacterial cells are known. Examples of bacterial cells include *E. coli*, for example, JM109, DH5α, HB101 and such and *Bacillus subtilis* are also known.

These cells are transformed by desired DNAs, and the transformants are cultured in vitro to obtain proteins. Transformants can be cultured using known methods. For example, the culture media for animal cells may be culture media such as DMEM, MEM, RPMI1640, or IMDM, and may be used with or without serum supplements such as fetal calf serum (FCS). The pH of the culture medium is preferably between about 6 and 8. Such cells are typically cultured at about 30 to 40° C. for about 15 to 200 hours, and the culture medium may be replaced, aerated, or stirred as necessary.

Production systems using animal and plant hosts may be used as systems for producing proteins in vivo. Target DNAs are introduced into these animal or plant hosts, and proteins are produced in the body of the animals or plants, and then recovered. These animals and plants are included in the "hosts" of the present invention.

The animals to be used for the production systems described above comprise mammals and insects. Mammals such as goats, pigs, sheep, mice, and cattle may be used. Alternatively, the mammals may be transgenic animals.

For instance, target DNAs may be prepared as fusion genes with genes that encode proteins specifically produced in milk, such as goat β casein gene. DNA fragments comprising the fusion genes are injected into goat embryos, which are then introduced back in to female goats. Target proteins are recovered from the milk produced by the transgenic goats (i.e., those goats born from the goats that received the embryos) or from their offspring. Appropriate hormones may be administered to increase the volume of milk comprising the proteins produced by transgenic goats.

Alternatively, insects such as silkworms may be used as hosts. In the case silkworms are use, baculoviruses, into which DNAs encoding desired proteins have been inserted, can be used to infect silkworms, and the desired proteins can be obtained from their body fluids.

In addition, when using plants, tobacco, for example, can be used. When using tobacco, DNAs encoding desired proteins may be inserted into plant expression vectors, such as pMON 530, which are introduced into bacteria, such as *Agro-* bacterium tumefaciens. Then, the bacteria are used to infect tobacco, such as Nicotiana tabacum, and the desired proteins can be obtained from the leaves.

Peptides of the present invention, obtained as above, can be isolated from the inside or outside (the medium and such) of host cells, and purified as substantially pure homogeneous peptides. Methods for separating and purifying peptides are not limited to any specific methods; in fact, any standard method for separating and purifying proteins may be used. For instance, column chromatography, filters, ultrafiltration, salting out, solvent precipitation, solvent extraction, distillation, immunoprecipitation, SDS-polyacrylamide gel electrophoresis, isoelectric point electrophoresis, dialysis, and recrystallization may be appropriately selected and combined to separate and purify the proteins.

Chromatography such as affinity chromatography, ion-exchange chromatography, hydrophobic chromatography, gel filtration, reverse phase chromatography and adsorption chromatography may be used. These chromatographies can be performed using liquid chromatographies, such as HPLC and FPLC. Thus, the present invention also encompasses highly purified proteins produced by the above purification methods.

The proteins may also be arbitrarily modified, or peptides may be partially removed, by the action of appropriate protein modification enzymes on the proteins, before or after purification. Protein modification enzymes such as trypsin, chymotrypsin, lysylendopeptidase, protein kinase, and glucosidase are used.

The present invention relates to antibodies that bind to the peptides,

The present invention also provides antibodies that bind to the proteins of the present invention. Examples of the antibodies of the present invention comprise monoclonal antibodies, polyclonal antibodies, antibody mutants, and fragments thereof.

These antibodies can be prepared by methods known to those skilled in the art. Polyclonal antibodies can be obtained, for example, by the following process: A small animal (such as a rabbit) is immunized with a juvenile hormone acid methyltransferase of Bombyx mori, Drosophila melanogaster, Anopheles gambiae, Spodoptera litura, or Helicoverpa armigera, or a recombinant protein expressed in a microorganism (such as Escherichia coli) as a fusion protein with GST, or a partial peptide thereof, and the serum is obtained. The serum is purified and prepared, for example, by ammonium sulfate precipitation, protein A or protein G column chromatography, DEAR ion-exchange chromatography, or amity column coupled with the juvenile hormone acid methyltransferase of Bombyx mori, Drosophila melanogaster, Anopheles gambiae, Spodoptera litura, or Helicoverpa armigera or synthetic peptides. Monoclonal antibodies can be obtained, for example, by the following process: A small animal (such as a mouse) is immunized with a juvenile hormone acid methyltransferase of Bombyx mori, Drosophila melanogaster, Anopheles gambiae, Spodoptera litura, or Helicoverpa armigera, or a partial peptide thereof, then the spleen is excised from the mouse and ground to separate the cells. The cells are fused with mouse myeloma cells using a reagent such as polyethylene glycol, thus obtaining fused cells (hybridoma) from which are selected clones that produce antibodies which bind to a juvenile hormone acid methyltransferase of Bombyx mori, Drosophila melanogaster, Anopheles gambiae, Spodoptera litura, or Helicoverpa armigera. The hybridomas thus obtained are then implanted intraperitoneally to a mouse, ascites are then recovered from the mouse, and monoclonal antibodies are obtained. Monoclonal antibodies thus obtained are purified by, for example, ammonium sulfate precipitation, protein A or protein G column chromatography, DEAE ion-exchange chromatography, or by an affinity column coupled with the juvenile hormone acid methyltransferase of Bombyx mori, Drosophila melanogaster, Anopheles gambiae, Spodoptera litura, or Helicoverpa armigera or a synthetic peptide.

In the present invention, "mutant antibody" refers to antibodies with amino acid sequence variations, in which one or more amino acid residues are altered. A "mutant antibody" of the present invention comprises variously altered amino acid variants, as long as they have the same binding specificity as the original antibody. Such mutants have less than 100% homology or similarity to an amino acid sequence that has at least 75%, more preferably at least 80%, even more preferably at least 85%, still more preferably at least 90%, and most preferably at least 95% amino acid sequence homology or similarity to the amino acid sequence of the variable domain of a heavy or light chain of an antibody.

Administering antibodies of the present invention to subjects enables detection of cancer cells, cancer cell-associated antigens, or endometrial cells developed at site other than inside the uterus in the subjects. The detection can be performed by methods known to those skilled in the art, by binding labeling substances to the antibodies.

The labeling substances are not particularly limited, so long as they can be used for immunological measurement methods. Specifically, enzymes, fluorescent substances, luminescent substances, radioactive substances, metal chelates and such can be used. Preferable labeling enzymes include, for example, peroxidase, alkaline phosphatase, β-D-galactosidase, malate dehydrogenase, staphylococcal nuclease, delta-5-steroid isomerase, α-glycerol phosphate dehydrogenase, triosephosphate isomerase, horseradish peroxidase, asparaginase, glucose oxidase, ribonuclease, urease, catalase, glucose-6-phosphate dehydrogenase, glucoamylase, acetylcholinesterase. Preferable fluorescent substances include, for example, fluorescein isothiocyanate, phycobiliprotein, rhodamine, phycoerythrin, phycocyanin, allophycocyanin, ortho-phthalaldehyde. Preferable luminescent substances include isoluminol, lucigenin, luminol, aromatic acridinium ester, imidazole, acridinium salts and modified esters thereof, luciferin, luciferase, aequorin and such. Preferable radioactive substances include $^{125}I$, $^{127}I$, $^{131}I$, $^{14}C$, $^{3}H$, $^{32}P$, $^{35}S$ and such.

Methods for binding the aforementioned labeling substances to antibodies are known. Specifically, direct labeling and indirect labeling can be used. As the direct labeling, methods in which antibodies or antibody fragments are chemically covalently bound with labels using cross-linking agents are common. Cross-linking agents such as N,N'-ortho-phenylene-dimaleimide, N-succinimidyl 4-(N-maleimidomethyl)cyclohexane acid, N-succinimidyl 6-maleimido hexane acid, 4,4'-dithiopyridine, and other known cross-linking agents can be used. These cross-linking agents can be reacted with enzymes and antibodies by known methods, depending on the characteristics of each of the cross-linking agents. In addition, methods can also be used wherein the antibodies are bound to a low molecular weight hapten, such as biotin, dinitrophenyl, pyridoxal or fluorescamine, and then indirectly labeled with a binding element that recognizes them. With regard to biotin, avidin, or streptavidine are used as recognizing ligands. On the other hand, with regard to dinitrophenyl, pyridoxal, or fluorescamine, antibodies that recognize these haptens are labeled. When labeling antibodies, horseradish peroxidase can be used as the labeling enzyme. This enzyme is advantageous since it can react with multiple substrates and can be readily bound to antibodies through the periodic acid method. Furthermore, in some cases, antibody fragments, for example Fab', Fab, and F(ab')$_2$, are used as the antibodies. Enzyme-labeled antibodies can be obtained by similar treatment, regardless of whether they are polyclonal or monoclonal antibodies. More sensitive immunoassay systems can be achieved by using known methods, such as affinity chromatography, to purify the enzyme-labeled products obtained using the aforementioned cross-linking agents. Purified enzyme-labeled antibodies are stored with the addition of thimerosal and such as antiseptics, and glycerin and such as stabilizers. By lyophilizing and storing in a cool and dark place, the labeled antibodies can be stored over longer periods.

If the antibodies of the present invention are used in combination with the aforementioned labeling substances, they can also be used as cancer tumor markers, immunostaining antibodies, or endometrial cell markers.

Herein, a "subject" indicates an organism, a part of the organism's body, or a part that has been excised or excreted from the organism, to which an agent (including a marker or the like) of the present invention is administered. The organisms are not particularly limited and include animals (for example, humans, domestic animal species, and wild animals).

Further, the "part of the organism's body" is not particularly limited; however, cancer cells and endometrial cells can be mentioned as preferable examples.

According to the present invention, cancer cells are exemplified more specifically by cancer cells of leukemia, colorectal cancer, lung cancer, breast cancer, head and neck squamous cancers, esophageal cancer, gastric cancer, thyroid cancer, osteosarcoma, chondrosarcoma, ovarian cancer, uterus cancer, renal cancer, pancreatic cancer, or glioblastoma. The cancer cells are not particularly limited in the present invention; however, more preferable examples are cancer cells of ovarian cancer, pancreatic cancer, or lung cancer. Moreover, more specific examples of endometrial cells in the present invention include endometrial cells that developed at sites other than the inside of the uterus during endometriosis. The sites other than the inside of the uterus are not particularly limited, and the myometrium can be mentioned as a preferable example. With regard to endometriosis, the condition where the development of the endometrium is limited to the myometrium is called adenomyosis uteri.

According to the present invention, "administer" includes oral and parenteral administrations.

Oral administration includes administration in the form of oral agents. The oral agents can be selected from drug forms such as granules, powders, tablets, capsules, solvents, emulsions and suspensions.

Parenteral administration can include administration in the form of injections. Exemplary injections include hypodermic injections, intramuscular injections, intraperitoneal injections and such. Furthermore, the effects of the methods of the present invention can be achieved by using gene therapy methods to introduce into living bodies those genes comprising the oligonucleotides to be administered. In addition, the agents of the present invention may be locally administered to regions that are to be treated. For example, administration can be performed by local infusion during operations, by using catheters, or by targeted gene delivery of DNAs encoding peptides of the present invention.

Examples of the agents of the present invention include reagents and DNA vaccines.

Pharmaceutically acceptable carriers, such as preservatives and stabilizers, may be added to the present agents. "Pharmaceutically acceptable" means that the material itself does not have the above-mentioned activity, but that it can be administered along with the above-mentioned agents.

As the stabilizers, gelatin or dextran at around 0.2%, sodium glutamate at 0.1% to 1.0%, lactose at about 5%, or sorbitol at about 2% can be used; however, the present invention is not limited thereto. As preservatives, such as thimerosal at around 0.01% or β-propionolactone at around 0.1% can be used; however, the present invention is not limited thereto.

When preparing injections, pH-adjusting agents, buffers, stabilizers, preservatives and such are added as required to prepare hypodermic, intramuscular, or intraperitoneal injections by conventional methods. The injections may also be formulated as ready-to-use preparations in the form of solid preparations by storing the solutions into containers and lyophilizing, for example. Moreover, dosages for one administration may be stored in containers, or dosages may be stored in the same container.

Various known methods may be employed when inoculating the agents of the present invention. Preferable inoculation methods include hypodermic injections, intramuscular injections, and percutaneous inoculations; however, the present invention is not limited thereto.

The dosages differ depending on the age, sex, body weight and condition of the patients, as well as the therapeutic effect, administration method, treatment time and/or the type of active ingredient contained in the agents; however, the agents can generally be administered to adults at a range of 0.1 mg to 500 mg, and preferably 0.5 mg to 20 mg at a time per individual. However, since the dosages change depending on various conditions, in some cases, smaller amounts than the above-mentioned dosages may be sufficient and, in other cases, dosages beyond the above-mentioned range may be required.

Appropriate inoculation methods are decided after considering the type of agent, the type of subject to be inoculated, and such. Containers such as vials and pre-filled syringe products can be employed. According to needs, the products may be solutions or powders made by lyophilization and such. The products may be for one or multiple inoculations. The dosages change depending on the type, body weight and age of the subjects to be administered, as well as the administration methods and such; however, those skilled in the art can appropriately select suitable dosages.

Furthermore, when administering the agents of the present invention to parts of an organism that has been excised or excreted from the organism, the agents may be "contacted" to the parts of the organism.

Moreover, the "contact" in the present invention is performed depending on the condition of the organisms. Examples include spraying the present agents on to the parts of the organism, adding the present agents to crushed parts of the organism, and such; however, the present invention is not limited thereto. When the parts of the organism are cultured cells, the above-mentioned "contact" can also be performed by adding the present agents to the cell culture medium, or by introducing DNAs comprising the oligonucleotides of the present invention into cells constituting the parts of the organism.

When carrying out the methods of the present invention, the agents of the present invention may be administered as one part of a pharmaceutical composition along with at least one known chemotherapeutic agent. Alternatively, the agents of the present invention may be administered separately from at least one known anti-cancer agent. In one embodiment, the agents of the present invention and the known chemotherapeutic agents may be administered at practically the same time.

The descriptions "subject" and "administer" used herein below have the same meaning as explained above.

The present invention relates to methods for activating T cells in subjects, where the methods comprise the step of administering these peptides into the subjects; the present invention also relates to T cells activated via these methods.

Herein, the T cells to be activated are not particularly limited. Preferable examples include helper T cells which promote immune responses, and conversely, suppressor T cells which suppress immune responses, as well as killer T cells which directly kill cancer cells and cells infected with pathogens.

More preferable examples include IL-4-producing human CD4-positive T cells, IFNγ-producing human CD4-positive T cells, TNFα-producing human CD4-positive T cells, and TNFα-producing human CD8-positive T cells.

According to the present invention, "activating T cells" means activating the functions of the various above-mentioned T cells and enhancing the production of these T cells; that is, "activating T cells" means the same as enhancing cellular immune responses. T cell activation can be measured by measuring the intensity of multiple activation markers expressed on the CD4 and CD8 cells. Exemplary activation markers include, but are not limited to, CD4 and IL-4, IFNγ, or TNFα for helper T cells, and CD8 and TNFα for killer T cells and suppressor T cells.

T cell activation can be measured according to methods known to those skilled in the art. Specifically, it can also be performed using the methods described in the Examples.

Herein, the period of T cells activation is not particularly limited; enhancement of T cell activation may be transient or for a certain period of time.

Transient enhancement indicates that the activated T cell state, caused by the administration of the peptides of the present invention, continues for a certain period of time and then returns to a constant state.

The present invention relates to methods for preventing or treating cancer diseases in subjects, where the methods comprise the step of administering these peptides or these antibodies to the subjects.

The present invention relates to methods for preventing or treating cancer diseases or endometriosis in subjects, where the methods comprise following steps (a) to (c):
(a) adding an above peptide to T cells;
(b) culturing the T cells of (a); and
(c) administering the T cells obtained in (b) to a subject.

The above-mentioned methods may also comprise, prior to step (a), a step wherein chemotherapy with anti-cancer agents is performed on the subject. The chemotherapy with anti-cancer agents is not particularly limited; however, chemotherapy combined with autologous peripheral blood stem cell transplantation is a more preferable example.

Herein, "preventing or treating cancer diseases or endometriosis" more specifically indicates manifesting a cell proliferation-suppressing effect or cell death-inducing effect, Further, the above-mentioned phrase also encompasses the improvement to normal state of a mutation or expressional change of a cancer-associated gene in a cancer cell. Furthermore, the above-mentioned phrase also encompasses suppression of the expression of endometrial cells that developed at a site other than inside the uterus during endometriosis. According to the above-mentioned methods, the period of amelioration of the cancer diseases or endometriosis is not particularly limited, and amelioration may be transient or for a certain period of time.

The present invention relates to agents for preventing or treating cancer diseases or endometriosis, which comprise the above peptides as active ingredients. Further, the present invention also relates to agents for preventing or treating cancer diseases or endometriosis, which comprise the above antibodies as active ingredients. In addition, the present invention also relates to agents for preventing or treating cancer diseases or endometriosis, which comprise the above T cells as active ingredients.

Pharmaceutically acceptable carriers, such as preservatives and stabilizers may be added to the agents of the present invention (which include the antibodies, T cells, markers and so on). "Pharmaceutically acceptable" indicates that the material itself does not possess the above-mentioned activities, but that it can be administered with the above-mentioned agents.

As stabilizers, gelatin or dextran at around 0.2%, sodium glutamate at 0.1% to 1.0%, lactose at about 5%, or sorbitol at about 2% can be used; however, the present invention is not limited thereto. As preservatives, thimerosal at around 0.01% or β-propionolactone at around 0.1% can be used; however, the present invention is not limited thereto.

When preparing injections, pH-adjusting agents, buffers, stabilizers, preservatives and such are added as required to prepare hypodermic, intramuscular, or intravenous injections by conventional methods. The injections may also be formulated as ready-to-use preparations in the form of solid preparations by storing the solutions into containers and lyophilizing, for example. Moreover, dosages for one administration may be stored in containers, or dosages may be stored in the same container. Appropriate inoculation methods can be decided after consideration of the type of agent, the type of subject to be inoculated, and such. Containers such as vials and pre-filled syringe products can be employed. According to needs, the products may be solutions or powders made by lyophilization and such. The products may be for one or multiple inoculations. The dosages change depending on the type, body weight, and age of the subjects to be administered, as well as the administration methods and such; however, those skilled in the art can appropriately select suitable dosages.

All prior art references cited herein are incorporated by reference into this description.

EXAMPLES

Hereinbelow, the present invention will be specifically described with reference to the Examples, but it is not to be construed as being limited thereto, Each of the Examples was conducted on the subjects below based on the following experimental conditions.

<Subjects>

After explaining the "Research relating to cell therapy against ovarian cancer", which had been approved by the Ethics Committee of the Saitama Medical University (Japan), peripheral venous blood samples (comprising T cells, B cells, antigen presenting cells and such as the mononuclear cell fraction) to be used for the present research (hereinafter referred to as 'blood samples') were donated by 25 ovarian cancer patients and eight healthy subjects with consent, and were anonymously analyzed (one blood sample per subject). In addition, blood samples after chemotherapy against ovarian cancer (Ikeba K, Okubo M, Takeda 5, et al.: Five-year results of cyclic semi-high dose chemotherapy supported by autologous peripheral blood stem cell transplantation in patients with advanced ovarian cancer, Int I Clin Oncol. 9: 113-119, 2004) were donated by six ovarian cancer patients to whom anti-cancer agents were being administered. As for the blood samples, 10 ml of blood was safely collected by physicians from the veins of the participants into test tubes containing an anticoagulant (heparin sodium).

<Cell Culture>

All operations concerning cell culture were performed aseptically. First, human peripheral mononuclear cell fractions (comprising T cells, B cells, macrophages and such; hereinafter referred to as "mononuclear cell samples") were prepared from the blood samples by density gradient centrifugation. Next, these mononuclear cells were suspended at $1\times10^5$ cell/ml in complete media having the following composition:

Complete Medium: RPMI1640 culture medium (Gibco Laboratories Inc., Grand Island, N.Y.) to which 10% fetal bovine serum (Cell Culture Laboratories, Cleveland, Ohio), 0.2 mM L-glutamine, 100 U/mL penicillin, 100 μg/mL streptomycin (Gibco Laboratories Inc.), and 0.2 ng/mL recombinant human IL-2 (Dainippon Pharmaceutical Co., Tokyo, Japan) have been mixed.

Theses mononuclear cell samples were placed still in V-bottomed 96-well tissue culture plastic plates (Flow Laboratories Inc., Horsham, Pa.) in the presence and absence of peptides, and cultured for 48 hours at 37° C. in a $CO_2$ culture apparatus (Sanyo Medica, Osaka, Japan).

<Detection of Intracellular Cytokines in CD4-Positive Cells>

A number of mouse-derived anti-human specific monoclonal antibodies with different fluorescences (hereinafter referred to as 'monoclonal antibodies') were used to simultaneously analyze by double-staining the CD markers CD4 and CD8, which are on the T cell membranes, and the cytokines within the T cells. As the monoclonal antibodies, products labeled with either fluorescent substance phycoerythrin (hereinafter 'PE') or fluorescein isothiocyanate (hereinafter 'FITC') were used (Miltenyi Biotec, Glandbach, Germany). For detection, a flow cytometry apparatus FACScan (Becton Dickinson) was used to measure the frequency of cells to which the monoclonal antibodies had bound. Positive cells are automatically detected by the flow cytometry apparatus. In brief, the cells are exposed to lasers, an excitation fluorescence is captured only from those cells to which the antibody of interest had bound, and the number of positive cells is calculated and displayed on computers.

Since positive cells cannot be identified after the cytokines have been secreted to the outside of the cells, detection was performed at a stage where the cytokines are inside the cells. Therefore, the Cytofix/Cytoperm Kit (Pharmingen, San Diego, Calif.) was used for the analysis, using methods recommended by the manufacturer and a positive control for detection recommended by the kit (Prussin C, Metcalfe D, Detection of intracytoplasmic cytokine using flow cytometry and directly conjugated anti-cytokine antibodies, J Immunol Meth. 188: 117-128, 1995). Specifically, brefeldin A (Pharmingen, San Diego, Calif.) was added at 0.7 μl/1 ml/well to stop protein production in the Golgi apparatus, and the peptide-stimulated mononuclear cell samples were treated at 37° C. for two hours. Next, the culture plates were placed on ice and the reaction was stopped by adding physiological saline at 4° C. The mononuclear cell samples were transferred into 15 ml tubes as though by washing with the physiological saline at 4° C., and were then centrifuged at 1600 rpm for ten minutes to remove the supernatant.

First, to dye CD4s on the cell surface, 10 μl of FITC-labeled mouse anti-human CD4 was added, with CD8 monoclonal antibody as a control, and this was reacted at 4° C. for 30 minutes. The cells were then separated with 0.5% bovine serum albumin/physiological saline at 4° C., then 0.5% bovine serum albumin/physiological saline at 4° C. was added thereto, and this was centrifuged at 1600 rpm for ten minutes at 4° C. to remove the supernatant.

Next, the mononuclear cell samples were fixed and their cell membranes were permeabilized. The cells were suspended in 250 μl of Cytofix/Cytoperm (Pharmingen) solution and reacted at 4° C. for 20 minutes. 10 μl of the aforementioned fluorescently labeled anti-IFNγ monoclonal antibody or anti-IL-4 monoclonal antibody was added to these mononuclear cell samples and reacted at 4° C. for 30 minutes. Then, the cells were separated by adding 0.5% bovine serum albumin/physiological saline at 4° C., and 0.5% BSA/PBS at 4° C. was further added thereto. After centrifugation at 1600 rpm for ten minutes at 4° C., the supernatant was removed. The cells were then washed and resuspended in PBS to analyze them using the flow cytometry apparatus FACScan (Becton Dickinson).

The results were recorded as: number of double staining-positive cells/total number of counted mononuclear cells ×100=positive cell frequency (%). Furthermore, peptide antigen-specific T cell reactions were determined to be positive when the individual frequencies of positive cells in the mononuclear cell samples were the same as or greater than the mean plus two standard deviations (mean+2SD) of the negative control group, where the negative control was a mononuclear cell sample group that had been stimulated with analogue peptide (OVCA10 stimulation). In addition, each of the peptide-stimulated groups were compared by using t-tests to measure the significant difference.

Example 1

Analysis of the Presence or Absence of T Cell Fractions Required for Cell Therapy in a Patient's Peripheral Blood After Chemotherapy with Anti-Cancer Agents Anti-cancer agents have the side effects of immune suppression or bone marrow suppression. Chemotherapy against ovarian cancers may cause changes in the cellular fractions in a patient's peripheral blood, and particularly, may reduce T cell number. Therefore, the cellular fractions contained in the blood samples of six patients were analyzed, where the blood samples had been taken on the day the peripheral leukocyte number had returned to normal values following chemotherapy with anti-cancer agents (after an average of 14 days). The blood samples were fluorescently immunostained using monoclonal antibodies (Fujisawa Pharmaceutical Co., Tokyo, Japan) against CD3 (general T cells), CD4 (helper T cells), CD8 (cytotoxic T cells), CD25 (activated T cells), CD45RA (naive T cells), CD4RO (memory T cells), CD 14 (monocytes), and CD 19 (B cells) for the Cluster of Differentiation (hereinafter referred to as 'CD') of blood cells; and the number of positive cells was analyzed using the flow cytometry apparatus FACScan (Becton Dickinson, San Jose, Calif.).

The results of the above experiment showed that the mean value of cells positive for the T cell marker CD3 was 58.5% over the six cases (standard value range: 48.9-89.0%; Nakahara K. T/B cell subset, blood surface markers, Guide for clinical testing 2003-2004, pp. 766-780, edited by Wada O., Bunkodo Co., Tokyo, 2003). Similarly, the mean value was 13.1% for CD19-positive cells which are B cells (3.0-26.1%), 5.9% (2% or lower) for CD14-positive cells which are monocytes, 31.0% for CD25-positive cells which are activated T cells, 19.5% for CD4-positive 45RA-positive cells which are naive-type helper T cells), 10.5% for CD4-positive 45RO-positive cells which are the memory-type helper T cells, 30.0% for all CD4-positive cells (24.0-61.0%), 4.0% for CD8-positive 45RA-positive cells which are naive-type cytotoxic T cells), 2.9% for CD8-positive 45RO-positive cells which are the memory-type cytotoxic T cells, and 6.9% for all CD8-positive cells (17.0-44.0%).

These results showed that, 14 days after chemotherapy, the number of T cells and B cells in the patients' peripheral blood are within normal range, and the number of monocytes has increased. In addition, in the T cell subset, the number of CD8-positive T cells was small, while CD4-positive T cells were abundant. Moreover, the result that the CD4-positive 45RO-positive cells, which are memory T cells, occupy 10.5% of the mononuclear cell samples indicates that, even after chemotherapy, enough mature T cells for use in cell therapy are present in the peripheral blood.

Example 2

Design of Analogue Peptides

CA125 was reported as the name of an antigen recognized by a monoclonal antibody prepared by Bast R C Jr. et al. in 1981 by immunizing mice with an ovarian cancer cell line antigen (Bast R C, Penney M, Lazarus H, Reactivity of a monoclonal antibody with human ovarian carcinoma, J Clin Invest. 68:1331-1337, 1981). In all ovarian, cancers, the positive rate for CA125 is about 70%, and in serous adenocarcinoma cell type, which is the most frequently seen in ovarian cancers, the positive rate is as much as about 90%. The absolute amount of CA125 characteristically increases with the progress of the cancer, and CA125 has been used as the most characteristic tumor marker for ovarian cancer cells. However, its molecular structure was only revealed quite recently. The amino acid sequence of the full-length CA125 is shown as SEQ ID NO: 45. CA125 is a protein to which sugar chains have been added, and it is one of the macromolecules called mucin. The core protein portion is called MUC after mucin, and CA125 was named MUC16, as one of the many MUCs present in vivo. The amino acid sequence of the core protein of this MUC16 was reported in 2001 by Yin B. et al. (Ym B W, Lloyd K O. Molecular cloning of the CA125 ovarian cancer antigen identification as a new mucin, MUC16, J Biol Chem. 276: 27371-27375, 2001). However, hitherto, the possibility of using CA125 as a cancer tumor-rejection antigen (an antigen that is immunologically recognized to eliminate cancer cells) had not yet been examined. Therefore, in the present invention, the ovarian cancer-associated antigen CA125 was used as a cancer tumor-rejection antigen.

Since T cells fundamentally recognize only the amino acid sequences presented on MHCs, only the amino acid sequence of MUC16, which is the core protein portion of CA125 not comprising the glycoproteins, was subjected to analysis. MUC16 comprises two types of sequences that repeat 78 amino acids eleven or twelve times (Yin B W, Lloyd K O. Molecular cloning of the CA125 ovarian cancer antigen identification as a new mucin, MUC16, J Biol Chem. 276: 27371-27375, 2001). When the present inventors prepared these sites containing repetitive sequences of 78 amino acid residues as synthetic peptides, they prepared them not as peptides with sequences completely identical to the original, but as similar peptides (hereinafter referred to as 'analogue peptides') by substituting with sequences having common amino acid hydrophobicity, hydrophilicity, or charge (FIGS. 1 to 3).

Generally, an epitope of a CD4-positive T cell comprises about 20 amino acid residues or less. Therefore, a preliminary experiment was performed with a total of 48 analogue peptides, by dividing the two repeat sequences and the remaining whole sequence into 20 amino acid residues. These 48 analogue peptides were custom-synthesized by an ISO9001-certified company (SIGMA Genosys Japan, Ishikari, Japan). Next, one repeat sequence portion for which a positive reaction had been observed in the preliminary experiment was analyzed by preparing an analogue peptide series of seven peptides of 20 amino acid residues each, where ten amino acid residues at the carboxyl end of each of the peptides overlapped with each other (FIG. 4). The concentrations of analogue peptides for mononuclear cell stimulation were 0, 5, 10, 15 , and 50 µM.

Example 3

Detection of Ovarian Cancer Antigen-Specific CD4-Positive T Cells

Antigen-specific T cells are known to produce IFNγ or IL-4 when activated (Fujiwara H., Immune response of T cells, Immunology of T cell system, pp. 155-174, written and edited by Fujiwara H., Chugai Igaku, Tokyo, 1993). When a T cell expressing IL-4 or IFNγ is detected after addition of ovarian cancer antigen MUC16 analogue peptide to a mononuclear cell fraction comprising T cells and stimulation by culturing, this serves as evidence of the presence of MUC16 antigen-specific T cells, and at the same time it means that the ovarian cancer antigen MUC16 analogue peptide comprises an epitope for T cells. However, when none of the ovarian cancer antigen MUC16 analogue peptides can activate the T cells, it means there are no MUC16 antigen-specific T cells.

In the preliminary experiment on six cases, CD4-positive/IL-4-positive cells were detected for a range between OVCA8 and OVCA14 among the 48 analogue peptides. Therefore, next, the present inventors used five analogue peptides, OVCA9 to OVCA 13 (SEQ ID NOs: 14, 13, 11, 12 and 15), to mononuclear cell samples of 33 subjects to detect CD4 and IL-4 or CD4 and IFNγ. As a result (Table 1, upper section), 27 of the 32 mononuclear cell samples (84.4%) became IL-4 positive (the mononuclear cell number was insufficient for one sample, thus this sample was omitted from the analysis), and 26 of the 33 mononuclear cell samples (78.8%) became IFNγ-positive after OVCA 11 stimulation. OVCA11: GHTAPGPLLVPFTLNFTITN (SEQ ID NO: 11) was thus demonstrated to activate T cells in an antigen-specific manner. Furthermore, OVCA12: PFTLNFTITNLRYEENMRHP (SEQ ID NO: 12) caused activation of IL-4-positive T cells in 18 of the 33 mononuclear cell samples, and of IFNγ-positive T cells in 13 of the 33 mononuclear cell samples. This positive reaction was concentration-dependent when the analogue peptide concentration was between 5 µM to 50 µM.

Typical examples of the results of flow cytometry analysis detecting IL-4 are shown in FIGS. 6 and 7. In these examples, positive cells were hardly detected in the control to which analogue peptide was not added, and in the mononuclear cell sample to which only IL-2 was added, the positive cell frequency being 0.04% and 0%, respectively. Furthermore, even when analogue peptides were added, cells that reacted to OVCA9(SEQ ID NO: 14) or OVCA10 (SEQ ID NO: 13) stimulation were hardly detected, the positive cell frequency being 0.05%. However, positive cells could be detected in 7.06% of mononuclear cell samples after stimulation with analogue peptide OVCA 11(SEQ ID NO: 11). In addition, some positive cells (0.57%) were present for OVCA12 (SEQ ID NO: 12).

Figure 8:
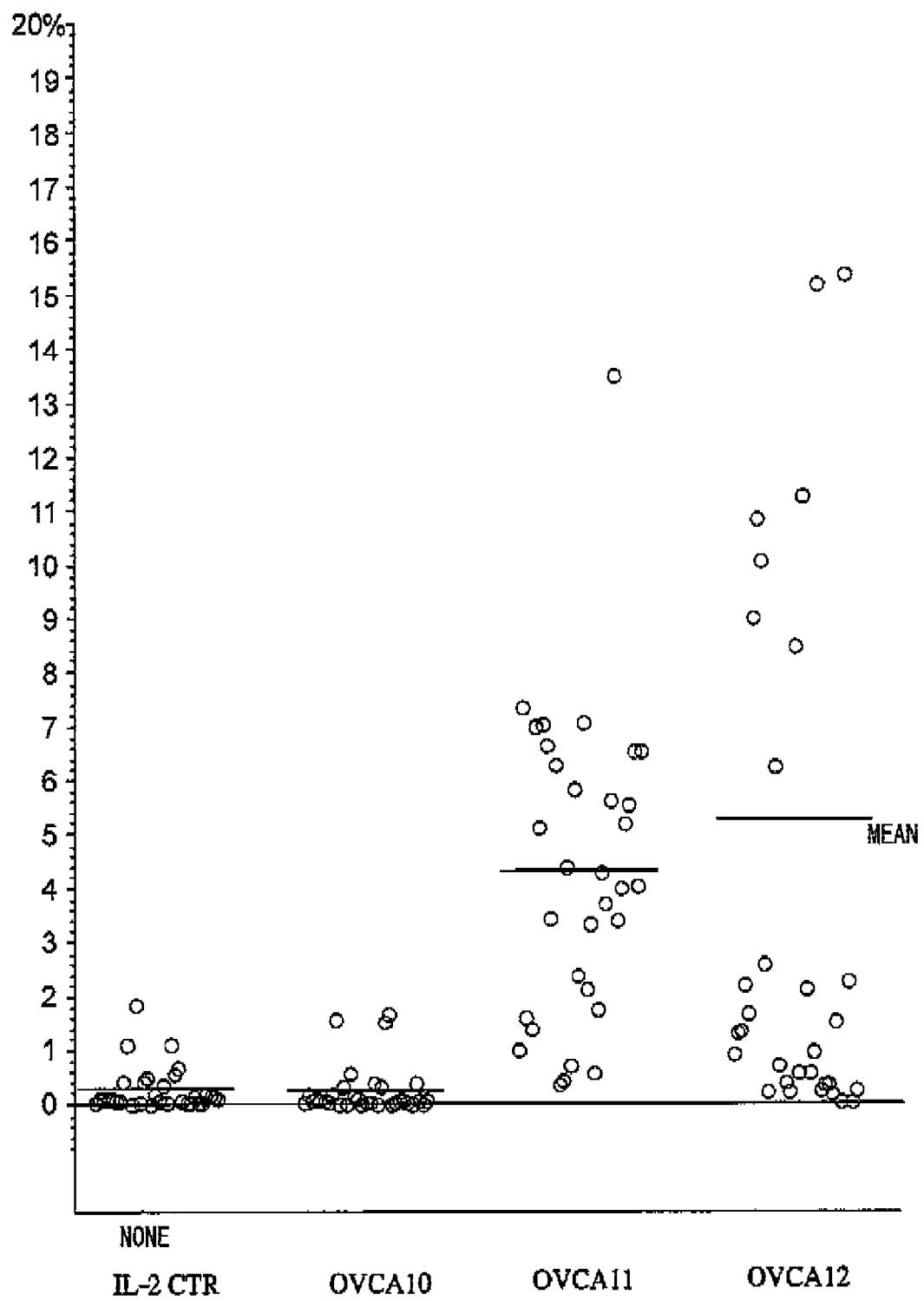
FIG. 8 shows the frequency of CD4-positive/IL-4-producing T cells. The frequency of positive cells was higher and had a statistically significant difference for mononuclear cell sample groups to which OVCA11 or OVCA 12 was added, as compared to mononuclear sample groups to which OVCA10 was added. The analogue peptide concentrations were 15 µM each.

The frequency of CD4-positive/IL-4-positive cells in all the analyzed mononuclear cell samples (FIG. 8) was an mean±standard deviation of 0.287±0.405% (32 samples), 0.252±0.448% (33 samples), 4.314±2.805% (32 samples) and 5.263±9.059% (33 samples) for the control mononuclear cell sample without the addition of analogue peptide and cultured with IL-2 alone (hereinafter referred to as 'Ctr-MNC'), the mononuclear cell sample to which analogue peptide OVCA10 (SEQ ID NO: 13) was added (hereinafter 'OVCA10-MNC'), the mononuclear cell sample to which analogue peptide OVCA11 (SEQ ID NO: 11) was added (hereinafter 'OVCA11-MNC'), and the mononuclear cell sample to which analogue peptide OVCA12 (SEQ ID NO: 12) was added (hereinafter 'OVCA12-MNC'), respectively. When the CD4-positive/IL-4-positive frequencies for OVCA11-MNC and OVCA12-MNC were compared to that of Ctr-MNC and OVCA10-MNC, statistically significant differences were obtained by t-tests, with $p<0.001$ for Ctr-MNC vs. OVCA11-MNC, $p=0.0028$ for Ctr-MNC vs. OVCA12-MNC, $p<0.001$ for OVCA10-MNC vs. OVCA11-MNC, and $p=0.0031$ for OVCA10-MNC vs. OVCA12-MNC.

Next, typical examples of the results of flow cytometry analysis detecting IFNγ are shown in FIGS. 9 and 10. In this example, positive cells were hardly detected, being 0.02% for the control to which analogue peptide was not added, and 0.08% for the sample to which only IL-2 was added. Furthermore, even when analogue peptides were added, T cells reacting to stimulation by OVCA9 (SEQ ID NO: 14) and OVCA10 were as low as 0.02% and 0.11%, respectively. However, analogue peptide stimulation with OVCA11 (SEQ II) NO: 11) resulted in detection of 3.12% positive cells. Few positive cells (0.28%) were present for OVCA12 (SEQ ID NO: 12).

Figure 11:
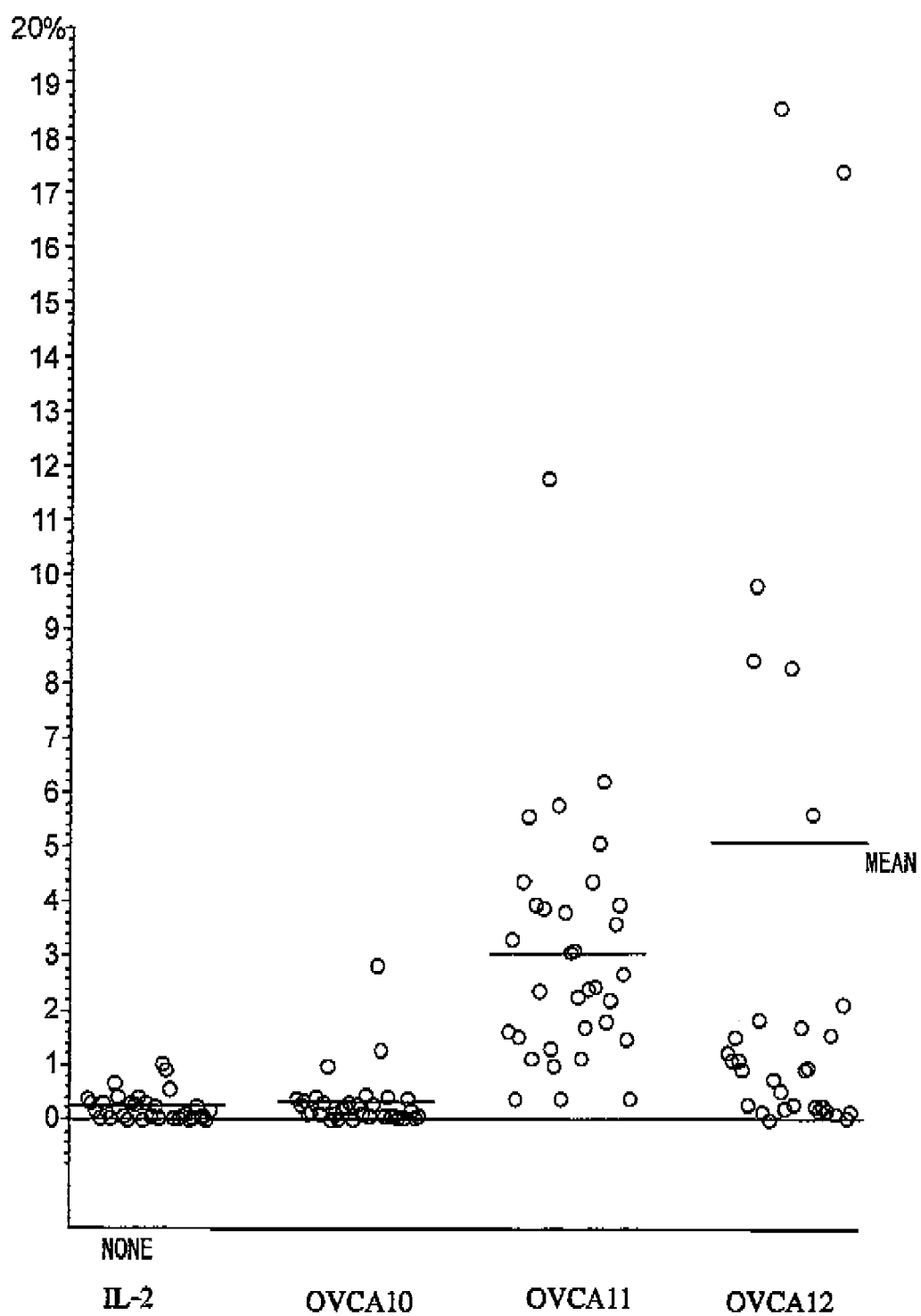
FIG. 11 shows the frequency of CD4-positive/IFNγ-producing T cells. The frequency of positive cells was higher and had a statistically significant difference for mononuclear cell sample groups to which OVCA11 or OVCA 12 was added as compared to mononuclear sample groups to which OVCA10 was added. The analogue peptide concentrations were 15 µM each.

The frequency of CD4-positive/INFγ-positive cells in all of the analyzed mononuclear cell samples (FIG. 11) was an mean±standard deviation of 0.243±0.258% (32 samples), 0.328±0.525% (33 samples), 3.037±2.234% (33 samples) and 5.071±10.315% (33 samples) for Ctr-MNC, OVCA10-MNC, OVCA11-MNC, and OVCA12-MNC, respectively. When CD4-positive/IFNγ-positive frequencies were compared between the mononuclear cell sample groups, statistically significant differences were obtained by t-tests, with $p<0.001$ for Ctr-MNC vs. OVCA11-MNC, $p=0.0116$ for Ctr-MNC vs. OVCA12-MNC, $p<0.001$ for OVCA10-MNC vs. OVCA11-MNC, and $p=0.0128$ for OVCA10-MNC vs. OVCA12-MNC.

The reaction of analogue peptide antigen-specific T cells was judged to be positive when the mean+2SD of the OVCA10-MNC group (1.148% for IL-4; 1.378% for IFNγ) or higher was obtained; the frequencies of positive mononuclear cell samples determined this way are shown in the upper section of Table 1. OVCA11-MNC resulted in 84.4% of IL-4 positives and 78.8% of IFNγ-positives; thus, OVCA11-MNC was recognized in many mononuclear cell samples and its frequencies were higher than those with OVCA12-MNC. In the patient group and healthy group, the average number of IL-4-positive cells was 4.12% and 4.89% respectively, and the average number of IFNγ-positive cells was 2.85% and 3.48%, respectively; this difference was not significant, but numbers tended to be smaller in the patient group than in the healthy group. The above results demonstrate the presence, in human peripheral blood, of T cells that recognize in an antigen-specific manner the amino acid sequences of the analogue peptides OVCA11 and OVCA12 of MUC16, i.e. GHTAPGPLLVPFTLNFTITNLRYEENMRHP (SEQ ID NO: 45), and produce IL-4 or IFNγ.

TABLE 1

| ID | SEQUENCE | CD4+ | IL-4+ | CD4+ | IFNγ+ | SEQ ID NO |
|---|---|---|---|---|---|---|
| OVCA9 | STPGTSTVHLGTSGTPASLP | 0/29 | 0% | 2/29 | 6.9% | 14 |
| OVCA10 | GTSGTPASLPGHTAPGPLLV | 1/33 | 3.0% | 1/33 | 3.0% | 13 |
| OVCA11 | GHTAPGPLLVPFTLNFTITN | 27/32 | 84.4% | 26/33 | 78.8% | 11 |
| OVCA12 | PFTLNFTITNLRYEENMRHP | 18/33 | 54.5% | 13/33 | 39.4% | 12 |
| OVCA13 | LRYEENMRHPGSRKFNTTER | 0/6 | 0% | 0/6 | 0% | 15 |
| OVCA101 | GHTAPVPLLI | 0/14 | 0% | 2/14 | 14.3% | 4 |
| OVCA102 | GHTAPGPLLV | 0/14 | 0% | 1/14 | 7.1% | 5 |
| OVCA103 | RPIVPGPLLV | 0/14 | 0% | 1/14 | 7.1% | 6 |
| OVCA104 | ETTATGPLLV | 0/14 | 0% | 1/14 | 7.1% | 7 |
| OVCA105 | GPTTASPLLV | 1/14 | 0% | 1/14 | 7.1% | 8 |
| OVCA106 | GPSAASPLLV | 2/14 | 14.3% | 2/14 | 14.3% | 9 |
| OVCA107 | PFTLNFTITN | 5/9 | 55.6% | 3/8 | 37.5% | 2 |
| OVCA108 | LFTLNPTITN | 5/9 | 55.6% | 2/8 | 25.0% | 3 |
| OVCA115 | LRYEENMRHP | 1/9 | 11.1% | 0/8 | 0% | 10 |

Positive sample > mean of control + 2 × SD.
Number of positive samples/tested samples × 100 (%)

Example 4

Measurement of Tumor Cytotoxic Activity of Activated T Cells

T cells activated in an antigen-specific manner are known to produce tumor necrosis factor α (TNFα) when they injure target cells, such as tumor cells. Therefore, the OVCA11-stimulated T cells obtained in [Example 3] were analyzed by flow cytometry to determine whether they indeed produced TNFα, using a similar method to [Example 3] and combinations of CD4 and TNFα, and CD8 and TNFα. FIG. 12 shows a typical example of the results. The frequency of CD4-positive/THFα-positive T cells was 0.44% before OVCA stimulation, and increased to 5.76% after OVCA11 stimulation. Similarly, CD8-positive/THFα-positive T cells, known to have stronger cytotoxicity, increased from 0.28% to 3.98%. These results confirmed that OVCA11 analogue peptide not only activates CD4-positive cells in an antigen-specific manner such that IL-4 and IFNγ are produced, but also induces the production of TNFα by CD4-positive and CD8-positive cells.

Example 5

Analysis of the CD4-Positive T Cell Epitope

The results of [Example 3] limited the site comprising the T cell epitope to within the regions of analogue peptides OVCA11: GHTAPGPLLVPFTLNFTITN (SEQ ID NO: 11) and OVCA12: PFTLNFTITNLRYEENNMRHP (SEQ ID NO: 12) (which are different from the original sequence).

Next, to determine the T cell epitope (based not on the analogues but on the original sequence), the present inventors went back to the original amino acid sequence of the 11-times repeat sequences of MUC16 from which the 30 amino acid residue sequence: GHTAPGPLLVPFTLNFTITNLRYEENMRHP (SEQ ID NO: 45) common to OVCA11 and OVCA12 was derived. Furthermore, the sequence was divided into lots of ten amino acid residues to prepare OVCA101 (SEQ ID NO: 4), 102 (SEQ ID NO: 5), 103 (SEQ ID NO: 6), 104 (SEQ ID NO: 7), 105 (SEQ ID NO: 8), 106 (SEQ ID NO: 9), 107 (SEQ ID NO: 2), 108 (SEQ ID NO: 3), 109, 110, 111, 112, 113, 114, 115 (SEQ ID NO: 10) (FIG. 5), and T cells positive for IL-4 or IFNγ were detected using a method similar to the above.

Figure 14:
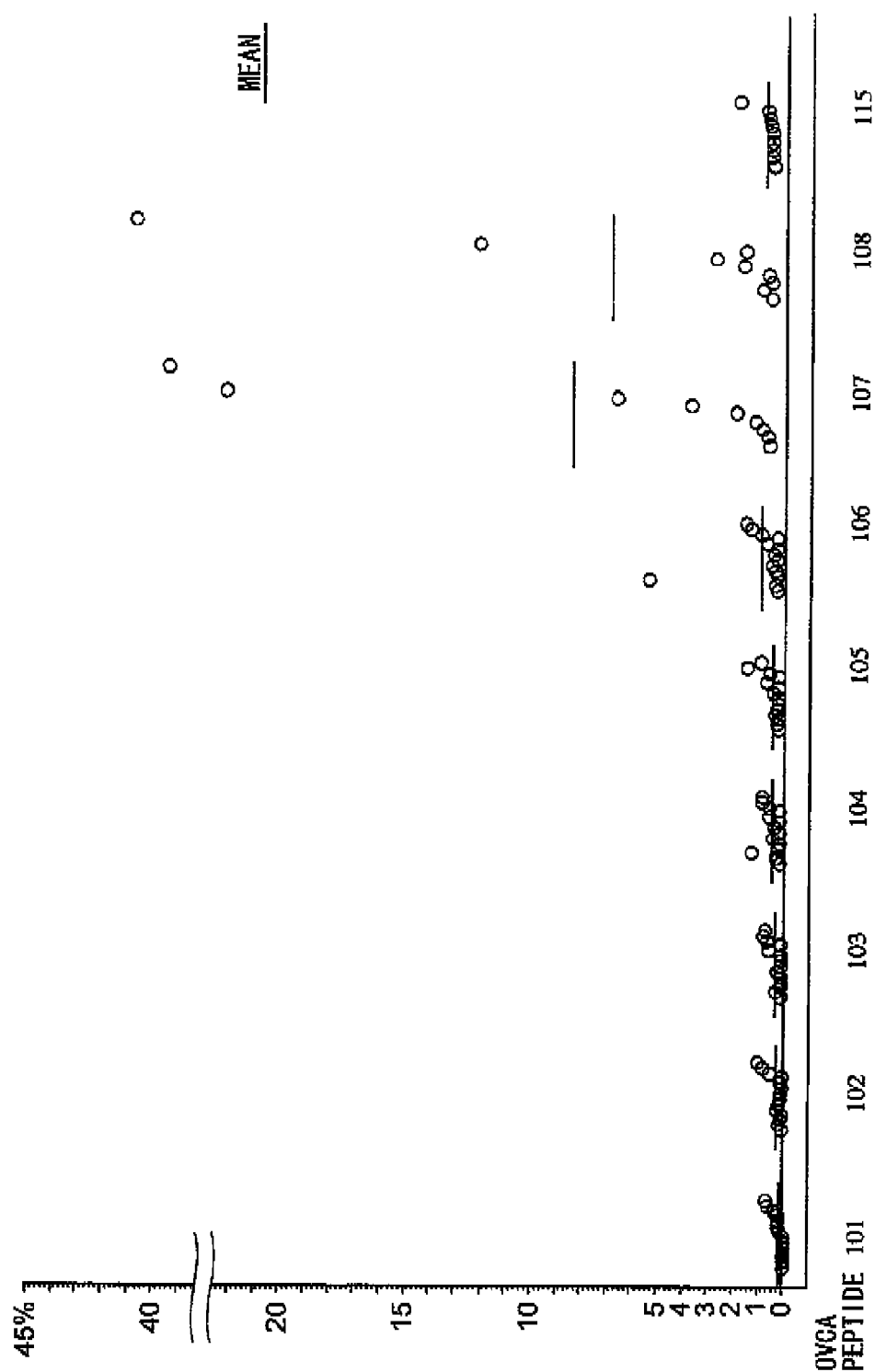
FIG. 14 shows the frequency of CD4-positive/IL-4-producing T cells at the time of epitope determination. High frequency cases could be detected from among the mononuclear sample groups to which OVCA107 or OVCA108 had been added. The analogue peptide concentrations were 15 µM each.

Typical examples of the results of flow cytometry analysis for CD4 and IL-4-positive cells are shown in FIG. 13. According to this example, OVCA107 peptide stimulation resulted in detection of 6.32% IL-4-positive cells. FIG. 14 depicts a graph showing the frequency of IL-4-positive cells for each of the mononuclear cell samples. The CD4-positive/IL-4-positive frequencies of the patient's mononuclear cell samples were expressed as a mean standard deviation% and were: OVCA101-MNC: 0.181±0.231% (14 samples); OVCA102-MNC: 0.231±0.309% (14 samples); OVCA103-MNC: 0.211±0.269% (14 samples); OVCA104-MNC: 0.301±0.340% (14 samples); OVCA105-MNC: 0.243±0.358% (14 samples); OVCA106-MNC: 0.649±1.337% (14 samples); OVCA107-MNC: 8.036±12.870% (9 samples); OVCA108-MNC: 6.471±13.319% (9 samples); and OVCA115-MNC: 0.281±0.424% (9 samples).

Figure 16:
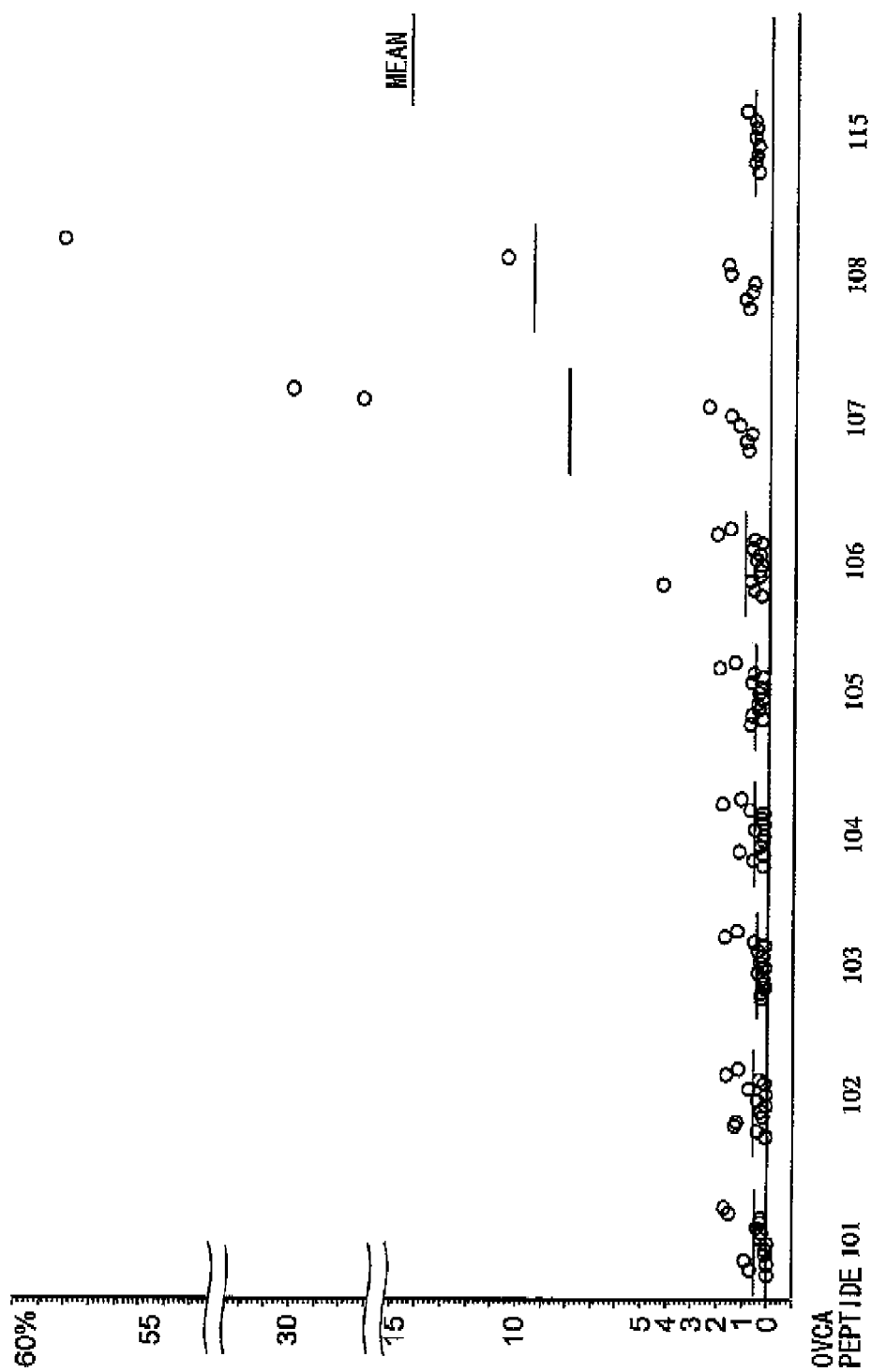
FIG. 16 shows the frequency of CD4-positive/IFNγ-producing T cells at the time of epitope determination. High frequency cases could be detected from among the mononuclear sample groups to which OVCA107 or OVCA108 had been added. The analogue peptide concentrations were 15 µM each.

Typical examples of the results of flow cytometry analysis for CD4 and IFNγ-positive cells are shown in FIG. 15. According to this example, OVCA107 stimulation resulted in detection of 2.10% positive cells. FIG. 16 depicts a graph showing the frequency of IFNγ-positive cells for each of the mononuclear cell samples. The CD4-positive/IFNγexpression-positive frequencies of the patient's mononuclear cell samples were expressed as a mean ± standard deviation% and were: OVCA101-MNC: 0.471±0.562% (14samples); OVCA102-MNC: 0.532±0.545% (14 samples); OVCA103-MNC: 0.331±0.467% (14samples); OVCA104-MNC: 0.376±0.490% (14 samples); OVCA105-MNC: 0.379±0.497% (14 samples); OVCA106-MNC: 0.641±1.082% (14 samples); OVCA107-MNC: 7.626±12.448% (8samples); OVCA108-MNC: 8.963±19.939% (8 samples); and OVCA115-MNC: 0.161±0.157% (8 samples).

Of the peptides with ten amino acid residues that reproduced the MUC16 primary amino acid structure sequence (FIG. 5), OVCA107 (SEQ ID NO: 2) and OVCA108 (SEQ ID NO: 3) were recognized by CD4-positive T cells, but OVCA101 to OVCA106 (SEQ ID NOs: 4 to 9) and OVCA115 (SEQ ID NO: 10) were not (Table 1). This result suggests that the amino acid sequence of the epitope for CD4-positive T cells is P/LFTLNFTITN (SEQ ID NO: 51). OVCA107 (SEQ ID NO: 2) and OVCA108 (SEQ ID NO: 3) are polypeptides that differ by one amino acid sequence (P/L) (see FIG. 5), but both are recognized by the mononuclear cell samples at almost the same frequency, with little difference (see Table 1, lower section). In view of the above, the substitution of P or L does not seem to influence the affinity for MHC class II molecules; therefore, a shorter T cell epitope can be said to be FTLNFTITN (SEQ ID NO: 1).

Peptides comprising this sequence of nine or ten amino acids can be used for T cell therapy. However, generally, the length of an epitope for CD4-positive T cells is said to be around 20 amino acid residues (Fujiwara H., Immune response of T cells, Immunology of T cell system, pp. 155-174, written and edited by Fujiwara H., Chugai Igaku, Tokyo, 1993). Indeed, when the frequency of positive T cells after stimulation with synthetic peptide OVCA107, which only comprises the epitope, was compared with that after stimulation with analogue peptide OVCA11, even if the molar concentration of the peptides were unified, the variance of the values of the positive T cell frequencies was less, and the reaction was more stable, when the cells were stimulated with OVCA11 than with OVCA107. Therefore, the analogue peptide OVCA11: GHTAPGPLLVPFTLNFTITN (SEQ ID NO: 11) is considered to be most suitable for T cell activation. Further, the number of positive mononuclear cell samples showing a frequency that was the same as or higher than the control's mean+2SD was larger than for OVCA107 stimulation, and peaked at 84.4% for OVCA11 stimulation. Therefore, it is thought that this analogue peptide seems less likely to develop differences between MHC class II molecule-dependent immune reactions of individuals, or that the analogue peptide has a sequence with an affinity that is tolerated by multiple MHC class II molecules, or a sequence that enhances the reaction of T cells. Thus, it is considered that the OVCA11 analogue peptide with 20 amino acid residues is better suited to cell therapy than the use of the short epitope region alone as the peptide.

The present invention reavealed that cell therapy can supplement chemotherapy. Thus, assuming that it is performed after chemotherapy (see FIG. 17), mononuclear cell fractions of peripheral blood from patients after the use of anti-cancer agents were analyzed. The results showed that two weeks after standard chemotherapy, the numbers of T cells and B cells returned to within normal range without further decrease, and the number of monocytes, which are antigen-presenting cells, increased, as did the number of CD4-positive T cells. These CD4-positive T cells, or helper T cells, comprised a sufficient number of memory T cells, which are involved in antigen re-recognition (CD4-positive/45RO-positive T cells). Compared to treatments of blood tumors, in chemotherapy against solid cancers such as ovarian cancers, suppression of hematopoietic cells by anti-cancer agents is weak. Therefore, with regard to the recovery of blood cells following suppression, it is said that mature memory T cells remaining in the periphery increase before naive T cells mobilized from the bone marrow increase, to reconstitute the T cells (Takahama Y., Dynamics/maintenance/differentiation of peripheral T cells, Immunology, the latest illustrated, edited by Koyasu S., Yodosha, Tokyo, 2003). The analysis of the present inventors also indicated that a sufficient number of memory T cells are comprised in the peripheral blood after chemotherapy, and that the state following chemotherapy with a standard dose of anti-cancer agent is even advantageous for T cell therapy.

Figure 17:
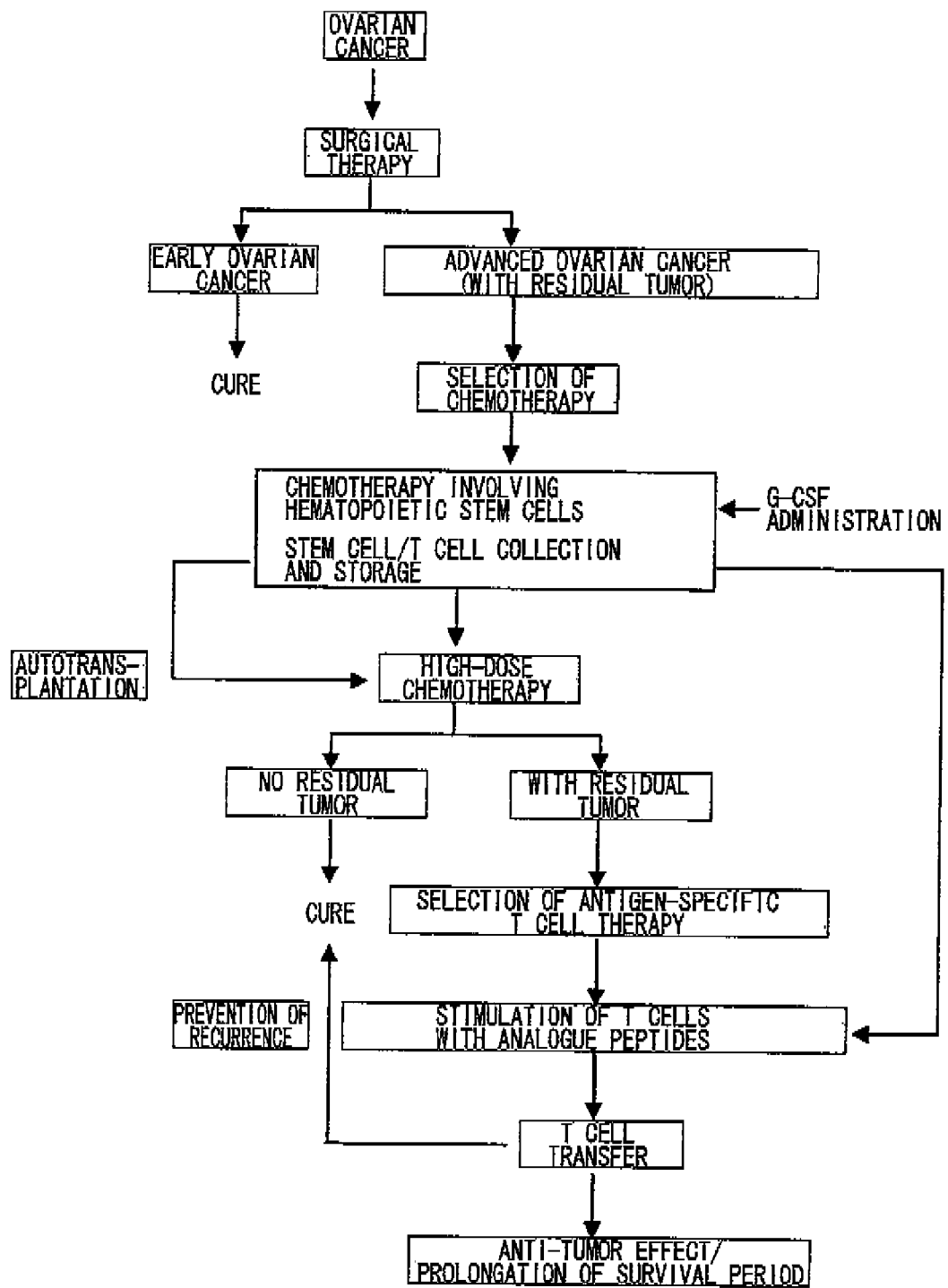
FIG. 17 shows a strategy of antigen-specific T cell therapy supplementing chemotherapy.
Figure 18:
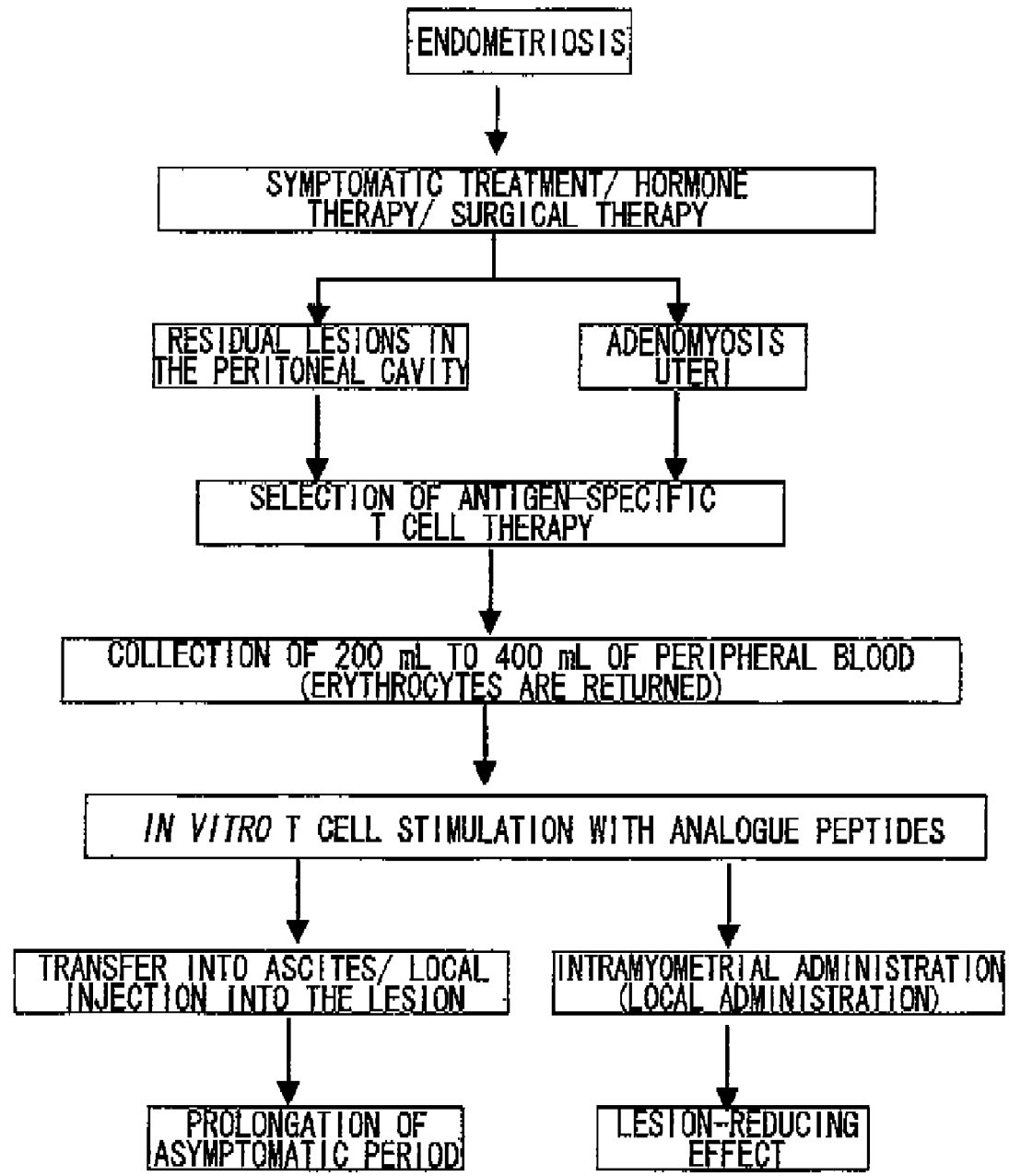
FIG. 18 shows a strategy of antigen-specific T cell therapy against endometriosis (adenomyosis uteri).

Of all chemotherapies performed against advanced ovarian cancers, chemotherapy combined with autologous peripheral blood stem cell transplantation provides the best therapeutic results (Ikeba K, Okubo M, Takeda S. et al., Five-year results of cyclic semi-high dose chemotherapy supported by autologous peripheral blood stem cell transplantation in patients with advanced ovarian cancer, Int J Clin Oncol. 9:113-119, 2004). In this therapeutic method, only hematopoietic stem cells, which were comprised at a few percent or so in mass-collected peripheral blood mononuclear cell fractions, were merely used to aid bone marrow functions that declined due to chemotherapy. The present analysis revealed that T cells for T cell therapy can be sufficiently obtained even after chemotherapy, thus demonstrating that peripheral mononuclear cell fractions collected during anti-cancer agent chemotherapy with autologous peripheral blood stem cell mobilization can be used for T cell therapy. In fact, since an extracorporeal circulation-type continuous centrifugal apparatus is used for collecting mononuclear cells during chemotherapy with peripheral blood stem cell mobilization, a large quantity of $2 \times 10^{10}$ mononuclear cells or more can be collected from an adult patient with a body weight of 50 kg or more. Based on the present measurement results that 10.5% are memory T cells even after chemotherapy, the number of memory T cells that can be collected using a continuous centrifugal apparatus reaches $2 \times 10^9$ cells. This is a number sufficient for use in cell therapy. Obtaining an equivalent number of T cells using conventional methods would require several months. From this perspective as well, antigen-specific T cell therapy strategies that use autologous T cells mass-obtained at the recovery stage of chemotherapy is considered advantageous (FIG. 17).

Industrial Applicability

The results of the present invention show that, by activating T cells of ovarian cancer patients with ovarian cancer antigen analogue peptides in vitro, and then returning them into the peripheral blood vessels or peritoneal cavity of the patients, advanced ovarian cancers can be treated through the mechanisms of: Th1-type CD4-positive T cells specific to ovarian cancer antigen analogue peptides, which (1) injure cancer cells indirectly via IFN and directly via TNFα; (2) exert an anti-tumor effect by assisting CD8-positive T cells; and (3) produce specific antibodies. Furthermore, in addition to the method of activating T cells outside the body and returning them to the body, it may be possible to treat or prevent ovarian cancers that produce ovarian cancer antigens by administering the ovarian cancer antigen analogue peptides to ovarian cancer patients as peptide vaccines to induce T cells and antibodies that recognize the ovarian cancer antigen analogue peptides in the body of the patients. Moreover, ovarian cancers which produce ovarian cancer antigens (CA125) may be treated by industrially producing components of immune antibodies (immunoglobulins) via heterologous immunization or genetic engineering methods using the ovarian cancer antigen analogue peptides as antigens, and then administering the anti-ovarian cancer antigen (CA125) antibodies to ovarian cancer patients. In addition, in contrast to conventional sugar chain-recognizing antibodies, these antibodies recognize amino acids and can be widely used as highly sensitive antibodies for tumor markers or immunostaining. Further, there are cases where the production of the ovarian cancer antigen CA125 has been detected in parts of pancreatic cancers, lung cancers, endometriosis (in particular, adenomyosis uteri), and such, in addition to ovarian, cancers. Therefore, similar treatments may be performed on all lesions that produce the ovarian cancer antigen CA125.

The invention claimed is:

1. A peptide that consists of 30 or fewer amino acids, wherein the peptide comprises the amino acid sequence of Phe-Thr-Leu-Asn-Phe-Thr-Ile-Thr-Asn (SEQ ID NO:1).

2. The peptide of claim 1, wherein the peptide induces T cell activation.

3. The peptide of claim 1, wherein the peptide comprises the amino acid sequence of Pro-Phe-Thr-Leu-Asn-Phe-Thr-Ile-Thr-Asn (SEQ ID NO:2).

4. The peptide of claim 3, wherein the peptide induces T cell activation.

5. The peptide of claim 1, wherein the peptide comprises the amino acid sequence of Leu-Phe-Thr-Leu-Asn-Phe-Thr-Ile-Thr-Asn (SEQ ID NO:3).

6. The peptide of claim 5, wherein the peptide induces T cell activation.

7. The peptide of claim 1, wherein the peptide comprises the amino acid sequence of Gly-His-Thr-Ala-Pro-Gly-Pro-Leu-Leu-Val-Pro-Phe-Thr-Leu-Asn-Phe-Thr-Ile-Thr-Asn (SEQ ID NO:11).

8. The peptide of claim 7, wherein the peptide induces T cell activation.

9. A peptide that comprises the amino acid sequence of Pro-Phe-Thr-Leu-Asn-Phe-Thr-Ile-Thr-Asn-Leu-Arg-Tyr-Glu-Glu-Asn-Met-Arg-His-Pro (SEQ ID NO:12).

10. The peptide of claim 9, wherein the amino acid sequence of the peptide consists of 30 or fewer amino acids.

11. The peptide of claim 9, wherein the peptide induces T cell activation.

* * * * *

SEQUENCE LISTING

```
<160> NUMBER OF SEQ ID NOS: 51

<210> SEQ ID NO 1
<211> LENGTH: 9
<212> TYPE: PRT
<213> ORGANISM: Homo sapiens

<400> SEQUENCE: 1

Phe Thr Leu Asn Phe Thr Ile Thr Asn
1               5

<210> SEQ ID NO 2
<211> LENGTH: 10
<212> TYPE: PRT
<213> ORGANISM: Homo sapiens

<400> SEQUENCE: 2

Pro Phe Thr Leu Asn Phe Thr Ile Thr Asn
1               5                   10
```

<210> SEQ ID NO 3
<211> LENGTH: 10
<212> TYPE: PRT
<213> ORGANISM: Homo sapiens

<400> SEQUENCE: 3

Leu Phe Thr Leu Asn Phe Thr Ile Thr Asn
1               5                   10

<210> SEQ ID NO 4
<211> LENGTH: 10
<212> TYPE: PRT
<213> ORGANISM: Homo sapiens

<400> SEQUENCE: 4

Gly His Thr Ala Pro Val Pro Leu Leu Ile
1               5                   10

<210> SEQ ID NO 5
<211> LENGTH: 10
<212> TYPE: PRT
<213> ORGANISM: Homo sapiens

<400> SEQUENCE: 5

Gly His Thr Ala Pro Gly Pro Leu Leu Val
1               5                   10

<210> SEQ ID NO 6
<211> LENGTH: 10
<212> TYPE: PRT
<213> ORGANISM: Homo sapiens

<400> SEQUENCE: 6

Arg Pro Ile Val Pro Gly Pro Leu Leu Val
1               5                   10

<210> SEQ ID NO 7
<211> LENGTH: 10
<212> TYPE: PRT
<213> ORGANISM: Homo sapiens

<400> SEQUENCE: 7

Glu Thr Thr Ala Thr Gly Pro Leu Leu Val
1               5                   10

<210> SEQ ID NO 8
<211> LENGTH: 10
<212> TYPE: PRT
<213> ORGANISM: Homo sapiens

<400> SEQUENCE: 8

Gly Pro Thr Thr Ala Ser Pro Leu Leu Val
1               5                   10

<210> SEQ ID NO 9
<211> LENGTH: 10
<212> TYPE: PRT
<213> ORGANISM: Homo sapiens

<400> SEQUENCE: 9

Gly Pro Ser Ala Ala Ser Pro Leu Leu Val
1               5                   10

```
<210> SEQ ID NO 10
<211> LENGTH: 10
<212> TYPE: PRT
<213> ORGANISM: Homo sapiens

<400> SEQUENCE: 10

Leu Arg Tyr Glu Glu Asn Met Arg His Pro
1               5                   10

<210> SEQ ID NO 11
<211> LENGTH: 20
<212> TYPE: PRT
<213> ORGANISM: Homo sapiens

<400> SEQUENCE: 11

Gly His Thr Ala Pro Gly Pro Leu Leu Val Pro Phe Thr Leu Asn Phe
1               5                   10                  15

Thr Ile Thr Asn
            20

<210> SEQ ID NO 12
<211> LENGTH: 20
<212> TYPE: PRT
<213> ORGANISM: Homo sapiens

<400> SEQUENCE: 12

Pro Phe Thr Leu Asn Phe Thr Ile Thr Asn Leu Arg Tyr Glu Glu Asn
1               5                   10                  15

Met Arg His Pro
            20

<210> SEQ ID NO 13
<211> LENGTH: 20
<212> TYPE: PRT
<213> ORGANISM: Homo sapiens

<400> SEQUENCE: 13

Gly Thr Ser Gly Thr Pro Ala Ser Leu Pro Gly His Thr Ala Pro Gly
1               5                   10                  15

Pro Leu Leu Val
            20

<210> SEQ ID NO 14
<211> LENGTH: 20
<212> TYPE: PRT
<213> ORGANISM: Homo sapiens

<400> SEQUENCE: 14

Ser Thr Pro Gly Thr Ser Thr Val His Leu Gly Thr Ser Gly Thr Pro
1               5                   10                  15

Ala Ser Leu Pro
            20

<210> SEQ ID NO 15
<211> LENGTH: 20
<212> TYPE: PRT
<213> ORGANISM: Homo sapiens

<400> SEQUENCE: 15

Leu Arg Tyr Glu Glu Asn Met Arg His Pro Gly Ser Arg Lys Phe Asn
1               5                   10                  15

Thr Thr Glu Arg
            20
```

-continued

```
<210> SEQ ID NO 16
<211> LENGTH: 78
<212> TYPE: PRT
<213> ORGANISM: Homo sapiens

<400> SEQUENCE: 16

Leu Phe Lys Ser Thr Ser Val Gly Pro Leu Tyr Ser Gly Cys Arg Leu
1               5                   10                  15

Thr Leu Leu Arg Pro Lys Lys Arg Lys Val Ala Thr Arg Val Asp Thr
            20                  25                  30

Ile Cys Thr Leu Arg Leu Asp Pro Thr Gly Pro Arg Leu Asn Arg Gln
        35                  40                  45

Arg Leu Tyr Leu Lys Leu Ser Gln Leu Thr Asn Ser Val Thr Glu Leu
    50                  55                  60

Gly Pro Tyr Thr Leu Asp Arg Asp Ser Leu Tyr Val Asn Gly
65                  70                  75

<210> SEQ ID NO 17
<211> LENGTH: 78
<212> TYPE: PRT
<213> ORGANISM: Homo sapiens

<400> SEQUENCE: 17

Leu Phe Lys Ser Thr Ser Val Gly Pro Leu Tyr Ser Gly Cys Arg Leu
1               5                   10                  15

Thr Leu Leu Arg Pro Glu Lys Asp Gly Glu Ala Thr Lys Val Asp Ala
            20                  25                  30

Ile Cys Thr Leu Arg Leu Asp Pro Leu Ile Pro Gly Leu Asp Arg Glu
        35                  40                  45

Arg Leu Tyr Trp Glu Leu Ser Gln Leu Thr Asn Ser Val Thr Glu Leu
    50                  55                  60

Gly Pro Tyr Thr Leu Asp Arg Asp Ser Leu Tyr Val Asn Gly
65                  70                  75

<210> SEQ ID NO 18
<211> LENGTH: 78
<212> TYPE: PRT
<213> ORGANISM: Homo sapiens

<400> SEQUENCE: 18

Leu Phe Lys Ser Thr Ser Val Gly Pro Leu Tyr Ser Gly Cys Arg Leu
1               5                   10                  15

Thr Leu Leu Arg Pro Glu Lys Asp Gly Ala Ala Thr Gly Val Asp Ala
            20                  25                  30

Ile Cys Thr Leu Arg Leu Asp Pro Gln Gly Pro Gly Leu Asp Arg Glu
        35                  40                  45

Arg Leu Tyr Trp Glu Leu Ser Gln Leu Thr Asn Ser Val Thr Glu Leu
    50                  55                  60

Gly Pro Tyr Thr Leu Asp Arg Asp Ser Leu Tyr Val Asn Gly
65                  70                  75

<210> SEQ ID NO 19
<211> LENGTH: 42
<212> TYPE: PRT
<213> ORGANISM: Homo sapiens
```

-continued

```
<400> SEQUENCE: 19

Arg Val Asp Pro Ile Gly Pro Gly Leu Asp Arg Glu Arg Leu Tyr Trp
1               5                   10                  15

Glu Leu Ser Gln Leu Thr Asn Ser Ile Thr Glu Leu Gly Pro Tyr Thr
            20                  25                  30

Leu Asp Arg Asp Ser Leu Tyr Val Asn Gly
        35                  40

<210> SEQ ID NO 20
<211> LENGTH: 78
<212> TYPE: PRT
<213> ORGANISM: Homo sapiens

<400> SEQUENCE: 20

Leu Phe Lys Ser Thr Ser Val Gly Pro Leu Tyr Ser Gly Cys Arg Leu
1               5                   10                  15

Thr Leu Leu Arg Pro Glu Lys His Gly Ala Ala Thr Gly Val Asp Ala
            20                  25                  30

Ile Cys Thr Leu Arg Leu Asp Pro Thr Gly Pro Gly Leu Asp Arg Glu
        35                  40                  45

Arg Leu Tyr Trp Glu Leu Ser Gln Leu Thr Asn Ser Val Thr Glu Leu
    50                  55                  60

Gly Pro Tyr Thr Leu Asp Arg Asp Ser Leu Tyr Val Asn Gly
65                  70                  75

<210> SEQ ID NO 21
<211> LENGTH: 78
<212> TYPE: PRT
<213> ORGANISM: Homo sapiens

<400> SEQUENCE: 21

Leu Phe Lys Ser Thr Ser Val Gly Pro Leu Tyr Ser Gly Cys Arg Leu
1               5                   10                  15

Thr Leu Leu Arg Pro Glu Lys Arg Gly Ala Ala Thr Gly Val Asp Thr
            20                  25                  30

Ile Cys Thr His Arg Leu Asp Pro Leu Asn Pro Gly Leu Asp Arg Glu
        35                  40                  45

Gln Leu Tyr Trp Glu Leu Ser Lys Leu Thr Arg Gly Ile Ile Glu Leu
    50                  55                  60

Gly Pro Tyr Leu Leu Asp Arg Gly Ser Leu Tyr Val Asn Gly
65                  70                  75

<210> SEQ ID NO 22
<211> LENGTH: 78
<212> TYPE: PRT
<213> ORGANISM: Homo sapiens

<400> SEQUENCE: 22

Leu Phe Lys Asn Thr Ser Ile Gly Pro Leu Tyr Ser Ser Cys Arg Leu
1               5                   10                  15

Thr Leu Leu Arg Pro Glu Lys Asp Lys Ala Ala Thr Arg Val Asp Ala
            20                  25                  30

Ile Cys Thr His His Pro Asp Pro Gln Ser Pro Gly Leu Asn Arg Glu
        35                  40                  45

Gln Leu Tyr Trp Glu Leu Ser Gln Leu Thr His Gly Ile Thr Glu Leu
    50                  55                  60

Gly Pro Tyr Thr Leu Asp Arg Asp Ser Leu Tyr Val Asp Gly
65                  70                  75
```

<210> SEQ ID NO 23
<211> LENGTH: 78
<212> TYPE: PRT
<213> ORGANISM: Homo sapiens

<400> SEQUENCE: 23

```
Leu Phe Lys Ser Thr Ser Val Gly Pro Leu Tyr Ser Gly Cys Arg Leu
1               5                   10                  15

Thr Leu Leu Arg Pro Glu Lys Asp Gly Val Ala Thr Arg Val Asp Ala
            20                  25                  30

Ile Cys Thr His Arg Pro Asp Pro Lys Ile Pro Gly Leu Asp Arg Gln
        35                  40                  45

Gln Leu Tyr Trp Glu Leu Ser Gln Leu Thr His Trp Ile Thr Glu Leu
    50                  55                  60

Gly Pro Tyr Thr Leu Asp Arg Asp Ser Leu Tyr Val Asn Gly
65                  70                  75
```

<210> SEQ ID NO 24
<211> LENGTH: 78
<212> TYPE: PRT
<213> ORGANISM: Homo sapiens

<400> SEQUENCE: 24

```
Leu Phe Lys Asn Thr Ser Val Ser Ser Leu Tyr Ser Gly Cys Arg Leu
1               5                   10                  15

Thr Leu Leu Arg Pro Glu Lys Asp Gly Ala Ala Thr Arg Val Asp Ala
            20                  25                  30

Val Cys Thr His Arg Pro Asp Pro Lys Ser Pro Gly Leu Asp Arg Glu
        35                  40                  45

Arg Leu Tyr Trp Lys Leu Ser Gln Leu Thr His Gly Ile Thr Glu Leu
    50                  55                  60

Gly Pro Tyr Thr Leu Asp Arg His Ser Leu Tyr Val Asn Gly
65                  70                  75
```

<210> SEQ ID NO 25
<211> LENGTH: 78
<212> TYPE: PRT
<213> ORGANISM: Homo sapiens

<400> SEQUENCE: 25

```
Val Phe Lys Asn Thr Ser Val Gly Pro Leu Tyr Ser Gly Cys Arg Leu
1               5                   10                  15

Thr Leu Leu Arg Pro Lys Lys Asp Gly Ala Ala Thr Lys Val Asp Ala
            20                  25                  30

Ile Cys Thr Tyr Arg Pro Asp Pro Lys Ser Pro Gly Leu Asp Arg Glu
        35                  40                  45

Gln Leu Tyr Trp Glu Leu Ser Gln Leu Thr His Ser Ile Thr Glu Leu
    50                  55                  60

Gly Pro Tyr Thr Leu Asp Arg Asp Ser Leu Tyr Val Asn Gly
65                  70                  75
```

<210> SEQ ID NO 26
<211> LENGTH: 78
<212> TYPE: PRT
<213> ORGANISM: Homo sapiens -continued

```
<400> SEQUENCE: 26

Leu Phe Lys Ser Thr Ser Val Gly Pro Leu Tyr Ser Gly Ser Pro Leu
1               5                   10                  15

Thr Leu Leu Arg Pro Glu Lys Asp Gly Thr Ala Thr Gly Val Asp Ala
            20                  25                  30

Ile Cys Thr His His Pro Asp Pro Lys Ser Pro Arg Leu Asp Arg Glu
        35                  40                  45

Gln Leu Tyr Trp Glu Leu Ser Gln Leu Thr His Asn Ile Thr Glu Leu
    50                  55                  60

Gly Pro Tyr Ala Leu Asp Asn Asp Ser Leu Phe Val Asn Gly
65                  70                  75

<210> SEQ ID NO 27
<211> LENGTH: 78
<212> TYPE: PRT
<213> ORGANISM: Homo sapiens

<400> SEQUENCE: 27

Leu Phe Lys Asn Thr Ser Val Gly Pro Leu Tyr Ser Gly Ser Arg Leu
1               5                   10                  15

Thr Leu Leu Arg Pro Glu Lys Asp Gly Glu Ala Thr Gly Val Asp Ala
            20                  25                  30

Ile Cys Thr His Arg Pro Asp Pro Thr Gly Pro Gly Leu Asp Arg Glu
        35                  40                  45

Gln Leu Tyr Leu Glu Leu Ser Gln Leu Thr His Ser Ile Thr Glu Leu
    50                  55                  60

Gly Pro Tyr Thr Leu Asp Arg Asp Ser Leu Tyr Val Asn Gly
65                  70                  75

<210> SEQ ID NO 28
<211> LENGTH: 78
<212> TYPE: PRT
<213> ORGANISM: Homo sapiens

<400> SEQUENCE: 28

Leu Phe Lys Ser Thr Ser Val Gly Pro Leu Tyr Ser Gly Cys Arg Leu
1               5                   10                  15

Thr Leu Leu Arg Pro Glu Lys Asp Gly Ala Ala Thr Gly Val Asp Ala
            20                  25                  30

Ile Cys Thr Leu Arg Pro Asp Pro Lys Ser Pro Gly Leu Asp Arg Glu
        35                  40                  45

Gln Leu Tyr Trp Glu Leu Ser Gln Leu Thr His Ser Ile Thr Glu Leu
    50                  55                  60

Gly Pro Tyr Thr Leu Asp Arg Asp Ser Leu Tyr Val Asn Gly
65                  70                  75

<210> SEQ ID NO 29
<211> LENGTH: 78
<212> TYPE: PRT
<213> ORGANISM: Homo sapiens

<400> SEQUENCE: 29

Phe Asn Pro Trp Ser Phe Met Thr Thr Thr Arg Ile Gly Asp Val Pro
1               5                   10                  15

Ala Met Asp Leu Ala Thr Ser Glu Ile Pro Ser Ser Lys Ser Arg Pro
            20                  25                  30

Ile Thr Thr Val His Leu Leu Val Leu Phe Thr Leu Asn Phe Thr Ile
        35                  40                  45
```

```
Thr Asn Leu Gln Tyr Met Ala Asp Met Gly Gln Pro Gly Ser Leu Lys
         50                  55                  60

Phe Asn Thr Thr Glu Arg Val Met Gln Gly Leu Leu Lys Pro
 65                  70                  75
```

<210> SEQ ID NO 30
<211> LENGTH: 78
<212> TYPE: PRT
<213> ORGANISM: Homo sapiens

<400> SEQUENCE: 30

```
Phe Thr Gln Gln Ser Ser Val Ser Thr Ser Ile Pro Val Thr Ser
  1               5                  10                  15

Ile Val Tyr Leu Glu Thr Ser Arg Thr Pro Pro Ser Leu Pro Glu Thr
                 20                  25                  30

Ser Ala Ala Ser Pro Leu Leu Val Pro Phe Thr Leu Asn Phe Thr Ile
                 35                  40                  45

Thr Asn Leu Gln Tyr Glu Glu Ala Met Gln His Pro Gly Ser Arg Lys
         50                  55                  60

Phe Asn Thr Thr Glu Arg Val Leu Gln Gly Leu Leu Ser Pro
 65                  70                  75
```

<210> SEQ ID NO 31
<211> LENGTH: 78
<212> TYPE: PRT
<213> ORGANISM: Homo sapiens

<400> SEQUENCE: 31

```
Phe Thr His Arg Ser Ser Val Pro Thr Thr Ser Ile Pro Gly Thr Ser
  1               5                  10                  15

Ala Val His Leu Glu Thr Ser Lys Thr Pro Ala Ser Leu Pro Gly His
                 20                  25                  30

Thr Ala Pro Gly Pro Leu Leu Val Pro Phe Thr Leu Asn Phe Thr Ile
                 35                  40                  45

Thr Asn Leu Gln Tyr Glu Glu Asp Met Trp His Pro Gly Ser Arg Lys
         50                  55                  60

Phe Asn Thr Thr Glu Arg Val Leu Gln Gly Leu Leu Lys Pro
 65                  70                  75
```

<210> SEQ ID NO 32
<211> LENGTH: 78
<212> TYPE: PRT
<213> ORGANISM: Homo sapiens

<400> SEQUENCE: 32

```
Phe Asn Pro Trp Ser Ser Val Pro Thr Thr Ser Thr Pro Gly Thr Ser
  1               5                  10                  15

Thr Val His Leu Ala Thr Ser Gly Thr Pro Ser Ser Leu Pro Gly His
                 20                  25                  30

Thr Ala Pro Val Pro Leu Leu Ile Pro Phe Thr Leu Asn Phe Thr Ile
                 35                  40                  45

Thr Asn Leu His Tyr Glu Glu Asn Met Gln His Pro Gly Ser Arg Lys
         50                  55                  60

Phe Asn Thr Thr Glu Arg Val Leu Gln Gly Leu Leu Lys Pro
 65                  70                  75
```

<210> SEQ ID NO 33
<211> LENGTH: 78
<212> TYPE: PRT
<213> ORGANISM: Homo sapiens

```
<400> SEQUENCE: 33

Phe Thr His Arg Ser Ser Val Pro Thr Thr Ser Ile Pro Gly Thr Ser
1               5                   10                  15

Ala Val His Leu Glu Thr Ser Gly Thr Pro Ala Ser Leu Pro Gly His
            20                  25                  30

Thr Ala Pro Gly Pro Leu Leu Val Pro Phe Thr Leu Asn Phe Thr Ile
        35                  40                  45

Thr Asn Leu Gln Tyr Glu Glu Asp Met Arg His Pro Gly Ser Arg Lys
    50                  55                  60

Phe Asn Thr Thr Glu Arg Val Leu Gln Gly Leu Leu Lys Pro
65                  70                  75

<210> SEQ ID NO 34
<211> LENGTH: 78
<212> TYPE: PRT
<213> ORGANISM: Homo sapiens

<400> SEQUENCE: 34

Phe Thr His Arg Asn Phe Val Pro Ile Thr Ser Thr Pro Gly Thr Ser
1               5                   10                  15

Thr Val His Leu Gly Thr Ser Glu Thr Pro Ser Ser Leu Pro Arg Pro
            20                  25                  30

Ile Val Pro Gly Pro Leu Leu Val Pro Phe Thr Leu Asn Phe Thr Ile
        35                  40                  45

Thr Asn Leu Gln Tyr Glu Glu Ala Met Arg His Pro Gly Ser Arg Lys
    50                  55                  60

Phe Asn Thr Thr Glu Arg Val Leu Gln Gly Leu Leu Arg Pro
65                  70                  75

<210> SEQ ID NO 35
<211> LENGTH: 78
<212> TYPE: PRT
<213> ORGANISM: Homo sapiens

<400> SEQUENCE: 35

Phe Thr His Trp Ser Pro Ile Pro Thr Thr Ser Thr Pro Gly Thr Ser
1               5                   10                  15

Ile Val Asn Leu Gly Thr Ser Gly Ile Pro Pro Ser Leu Pro Glu Thr
            20                  25                  30

Thr Ala Thr Gly Pro Leu Leu Val Pro Phe Thr Leu Asn Phe Thr Ile
        35                  40                  45

Thr Asn Leu Gln Tyr Glu Glu Asn Met Gly Arg Pro Gly Ser Arg Lys
    50                  55                  60

Phe Asn Ile Thr Glu Ser Val Leu Gln Gly Leu Leu Lys Pro
65                  70                  75

<210> SEQ ID NO 36
<211> LENGTH: 78
<212> TYPE: PRT
<213> ORGANISM: Homo sapiens

<400> SEQUENCE: 36

Phe Thr His Gln Ser Ser Met Thr Thr Arg Thr Pro Asp Thr Ser
1               5                   10                  15

Thr Met His Leu Ala Thr Ser Arg Thr Pro Ala Ser Leu Ser Gly Pro
            20                  25                  30

Thr Thr Ala Ser Pro Leu Leu Val Leu Phe Thr Ile Asn Phe Thr Ile
        35                  40                  45
```

```
Thr Asn Leu Arg Tyr Glu Glu Asn Met His His Pro Gly Ser Arg Lys
         50                  55                  60

Phe Phe Thr Thr Glu Arg Val Leu Gln Gly Leu Leu Arg Pro
 65                  70                  75
```

<210> SEQ ID NO 37
<211> LENGTH: 78
<212> TYPE: PRT
<213> ORGANISM: Homo sapiens

<400> SEQUENCE: 37

```
Phe Thr Gln Arg Ser Ser Val Pro Thr Thr Ser Ile Pro Gly Thr Pro
 1               5                  10                  15

Thr Val Asp Leu Gly Thr Ser Gly Thr Pro Val Ser Lys Pro Gly Pro
                 20                  25                  30

Ser Ala Ala Ser Pro Leu Leu Val Leu Phe Thr Leu Asn Phe Thr Ile
                 35                  40                  45

Thr Asn Leu Arg Tyr Glu Glu Asn Met Gln His Pro Gly Ser Arg Lys
         50                  55                  60

Phe Asn Thr Thr Glu Arg Val Leu Gln Gly Leu Leu Arg Ser
 65                  70                  75
```

<210> SEQ ID NO 38
<211> LENGTH: 77
<212> TYPE: PRT
<213> ORGANISM: Homo sapiens

<400> SEQUENCE: 38

```
Phe Thr His Arg Ser Ser Val Ser Thr Thr Ser Thr Pro Gly Thr Pro
 1               5                  10                  15

Thr Val Tyr Leu Gly Ala Ser Lys Thr Pro Ala Ser Ile Phe Gly Pro
                 20                  25                  30

Ser Ala Ala Ser His Leu Leu Ile Leu Phe Thr Leu Asn Phe Thr Ile
                 35                  40                  45

Thr Asn Leu Arg Tyr Glu Glu Asn Met Trp Pro Gly Ser Arg Lys Phe
         50                  55                  60

Asn Thr Thr Glu Arg Val Leu Gln Gly Leu Leu Arg Pro
 65                  70                  75
```

<210> SEQ ID NO 39
<211> LENGTH: 56
<212> TYPE: PRT
<213> ORGANISM: Homo sapiens

<400> SEQUENCE: 39

```
Phe Thr His Arg Ser Ser Val Pro Thr Thr Ser Thr Gly Val Val Ser
 1               5                  10                  15

Glu Glu Pro Phe Thr Leu Asn Phe Thr Ile Asn Asn Leu Arg Tyr Met
                 20                  25                  30

Ala Asp Met Gly Gln Pro Gly Ser Leu Lys Phe Asn Ile Thr Asp Asn
                 35                  40                  45

Val Met Gln His Leu Leu Ser Pro
         50                  55
```

<210> SEQ ID NO 40
<211> LENGTH: 78
<212> TYPE: PRT
<213> ORGANISM: Homo sapiens

```
-continued

<400> SEQUENCE: 40

Phe Thr His Arg Ser Ser Val Pro Thr Thr Ser Thr Pro Gly Thr Ser
1               5                   10                  15

Thr Val His Leu Gly Thr Ser Gly Thr Pro Ala Ser Leu Pro Gly His
            20                  25                  30

Thr Ala Pro Gly Pro Leu Leu Val Pro Phe Thr Leu Asn Phe Thr Ile
        35                  40                  45

Thr Asn Leu Arg Tyr Glu Glu Asn Met Arg His Pro Gly Ser Arg Lys
    50                  55                  60

Phe Asn Thr Thr Glu Arg Val Leu Gln Gly Leu Leu Arg Pro
65                  70                  75

<210> SEQ ID NO 41
<211> LENGTH: 545
<212> TYPE: PRT
<213> ORGANISM: Homo sapiens

<400> SEQUENCE: 41

Leu Phe Gln Arg Ser Ser Leu Gly Ala Arg Tyr Thr Gly Cys Arg Val
1               5                   10                  15

Ile Ala Leu Arg Ser Val Lys Asn Gly Ala Glu Thr Arg Val Asp Leu
            20                  25                  30

Leu Cys Thr Tyr Leu Gln Pro Leu Ser Gly Pro Gly Leu Pro Ile Lys
        35                  40                  45

Gln Val Phe His Glu Leu Ser Gln Gln Thr His Gly Ile Thr Arg Leu
    50                  55                  60

Gly Pro Tyr Ser Leu Asp Lys Asp Ser Leu Tyr Leu Asn Gly Tyr Asn
65                  70                  75                  80

Glu Pro Gly Pro Asp Glu Pro Pro Thr Thr Pro Lys Pro Ala Thr Thr
                85                  90                  95

Phe Leu Pro Pro Leu Ser Glu Ala Thr Thr Ala Met Gly Tyr His Leu
            100                 105                 110

Lys Thr Leu Thr Leu Asn Phe Thr Ile Ser Asn Leu Gln Tyr Ser Pro
        115                 120                 125

Asp Met Gly Lys Gly Ser Ala Thr Phe Asn Ser Thr Glu Gly Val Leu
    130                 135                 140

Gln His Leu Leu Arg Pro Leu Phe Gln Lys Ser Ser Met Gly Pro Phe
145                 150                 155                 160

Tyr Leu Gly Cys Gln Leu Ile Ser Leu Arg Pro Glu Lys Asp Gly Ala
                165                 170                 175

Ala Thr Gly Val Asp Thr Thr Cys Thr Tyr His Pro Asp Pro Val Gly
            180                 185                 190

Pro Gly Leu Asp Ile Gln Gln Leu Tyr Trp Glu Leu Ser Gln Leu Thr
        195                 200                 205

His Gly Val Thr Gln Leu Gly Phe Tyr Val Leu Asp Arg Asp Ser Leu
    210                 215                 220

Phe Ile Asn Gly Tyr Ala Pro Gln Phe Leu Ser Ile Arg Gly Glu Tyr
225                 230                 235                 240

Gln Ile Asn Phe His Ile Val Asn Trp Asn Leu Ser Asn Pro Asp Pro
                245                 250                 255

Thr Ser Ser Glu Tyr Ile Thr Leu Leu Arg Asp Ile Gln Asp Lys Val
            260                 265                 270

Thr Thr Leu Tyr Lys Gly Ser Gln Leu His Asp Thr Phe Arg Phe Cys
        275                 280                 285
```

-continued

```
Leu Val Thr Asn Leu Thr Met Asp Ser Val Leu Val Thr Lys Ala
            290                 295                 300
Leu Phe Ser Ser Asn Leu Asp Pro Ser Leu Val Glu Gln Val Phe Leu
305                 310                 315                 320
Asp Lys Thr Leu Phe Ala Ser Phe His Trp Leu Gly Ser Thr Tyr Gln
                325                 330                 335
Leu Val Asp Ile His Val Thr Glu Met Glu Ser Ser Val Tyr Gln Pro
            340                 345                 350
Gly Ser Ser Ser Thr Gln His Phe Tyr Pro Asn Phe Ile Thr Thr
            355                 360                 365
Asn Leu Pro Tyr Ser Gln Asp Lys Ala Gln Pro Gly Thr Thr Asn Tyr
370                 375                 380
Gln Arg Asn Lys Arg Asn Ile Glu Asp Ala Leu Asn Gln Leu Phe Arg
385                 390                 395                 400
Asn Ser Ser Ile Lys Ser Tyr Phe Ser Asp Cys Gln Val Ser Thr Phe
                405                 410                 415
Arg Ser Val Pro Asn Arg His His Thr Gly Val Asp Ser Leu Cys Asn
            420                 425                 430
Phe Ser Pro Leu Ala Arg Arg Val Asp Arg Val Ala Ile Tyr Glu Glu
            435                 440                 445
Phe Leu Arg Met Thr Arg Asn Gly Thr Gln Leu Gln Asn Phe Thr Leu
450                 455                 460
Asp Arg Ser Ser Val Leu Val Asp Gly Tyr Ser Pro Asn Arg Asn Glu
465                 470                 475                 480
Pro Leu Thr Gly Asn Ser Asp Leu Pro Phe Trp Ala Val Ile Leu Ile
                485                 490                 495
Gly Leu Ala Gly Leu Leu Gly Leu Ile Thr Cys Leu Ile Cys Gly Val
            500                 505                 510
Leu Val Thr Thr Arg Arg Arg Lys Lys Glu Gly Glu Tyr Asn Val Gln
            515                 520                 525
Gln Gln Cys Pro Gly Tyr Tyr Gln Ser His Leu Asp Leu Glu Asp Leu
530                 535                 540
Gln
545

<210> SEQ ID NO 42
<211> LENGTH: 20
<212> TYPE: PRT
<213> ORGANISM: Homo sapiens

<400> SEQUENCE: 42

Phe Thr His Arg Ser Ser Val Pro Thr Thr Ser Thr Pro Gly Thr Ser
1               5                   10                  15

Thr Val His Leu
            20

<210> SEQ ID NO 43
<211> LENGTH: 18
<212> TYPE: PRT
<213> ORGANISM: Homo sapiens

<400> SEQUENCE: 43

Gly Ser Arg Lys Phe Asn Thr Thr Glu Arg Val Leu Gln Gly Leu Leu
1               5                   10                  15

Arg Pro
```

<210> SEQ ID NO 44
<211> LENGTH: 6995
<212> TYPE: PRT
<213> ORGANISM: Homo sapiens

<400> SEQUENCE: 44

Pro Val Thr Ser Leu Leu Thr Pro Gly Leu Val Ile Thr Thr Asp Arg
1               5                   10                  15

Met Gly Ile Ser Arg Glu Pro Gly Thr Ser Thr Ser Asn Leu Ser
            20                  25                  30

Ser Thr Ser His Glu Arg Leu Thr Thr Leu Glu Asp Thr Val Asp Thr
        35                  40                  45

Glu Ala Met Gln Pro Ser Thr His Thr Ala Val Thr Asn Val Arg Thr
    50                  55                  60

Ser Ile Ser Gly His Glu Ser Gln Ser Ser Val Leu Ser Asp Ser Glu
65                  70                  75                  80

Thr Pro Lys Ala Thr Ser Pro Met Gly Thr Thr Tyr Thr Met Gly Glu
                85                  90                  95

Thr Ser Val Ser Ile Ser Thr Ser Asp Phe Phe Glu Thr Ser Arg Ile
            100                 105                 110

Gln Ile Glu Pro Thr Ser Ser Leu Thr Ser Gly Leu Arg Glu Thr Ser
        115                 120                 125

Ser Ser Glu Arg Ile Ser Ser Ala Thr Glu Gly Ser Thr Val Leu Ser
130                 135                 140

Glu Val Pro Ser Gly Ala Thr Thr Glu Val Ser Arg Thr Glu Val Ile
145                 150                 155                 160

Ser Ser Arg Gly Thr Ser Met Ser Gly Pro Asp Gln Phe Thr Ile Ser
                165                 170                 175

Pro Asp Ile Ser Thr Glu Ala Ile Thr Arg Leu Ser Thr Ser Pro Ile
            180                 185                 190

Met Thr Glu Ser Ala Glu Ser Ala Ile Thr Ile Glu Thr Gly Ser Pro
        195                 200                 205

Gly Ala Thr Ser Glu Gly Thr Leu Thr Leu Asp Thr Ser Thr Thr Thr
    210                 215                 220

Phe Trp Ser Gly Thr His Ser Thr Ala Ser Pro Gly Phe Ser His Ser
225                 230                 235                 240

Glu Met Thr Thr Leu Met Ser Arg Thr Pro Gly Asp Val Pro Trp Pro
                245                 250                 255

Ser Leu Pro Ser Val Glu Glu Ala Ser Ser Val Ser Ser Ser Leu Ser
            260                 265                 270

Ser Pro Ala Met Thr Ser Thr Ser Phe Phe Ser Thr Leu Pro Glu Ser
        275                 280                 285

Ile Ser Ser Ser Pro His Pro Val Thr Ala Leu Leu Thr Leu Gly Pro
    290                 295                 300

Val Lys Thr Thr Asp Met Leu Arg Thr Ser Ser Glu Pro Glu Thr Ser
305                 310                 315                 320

Ser Pro Pro Asn Leu Ser Ser Thr Ser Ala Glu Ile Leu Ala Thr Ser
                325                 330                 335

Glu Val Thr Lys Asp Arg Glu Lys Ile His Pro Ser Ser Asn Thr Pro
            340                 345                 350

Val Val Asn Val Gly Thr Val Ile Tyr Lys His Leu Ser Pro Ser Ser
        355                 360                 365

Val Leu Ala Asp Leu Val Thr Thr Lys Pro Thr Ser Pro Met Ala Thr
    370                 375                 380

```
Thr Ser Thr Leu Gly Asn Thr Ser Val Ser Thr Ser Thr Pro Ala Phe
385                 390                 395                 400

Pro Glu Thr Met Met Thr Gln Pro Thr Ser Leu Thr Ser Gly Leu
                405                 410                 415

Arg Glu Ile Ser Thr Ser Gln Glu Thr Ser Ser Ala Thr Glu Arg Ser
            420                 425                 430

Ala Ser Leu Ser Gly Met Pro Thr Gly Ala Thr Thr Lys Val Ser Arg
        435                 440                 445

Thr Glu Ala Leu Ser Leu Gly Arg Thr Ser Thr Pro Gly Pro Ala Gln
    450                 455                 460

Ser Thr Ile Ser Pro Glu Ile Ser Thr Glu Thr Ile Thr Arg Ile Ser
465                 470                 475                 480

Thr Pro Leu Thr Thr Thr Gly Ser Ala Glu Met Thr Ile Thr Pro Lys
                485                 490                 495

Thr Gly His Ser Gly Ala Ser Ser Gln Gly Thr Phe Thr Leu Asp Thr
                500                 505                 510

Ser Ser Arg Ala Ser Trp Pro Gly Thr His Ser Ala Ala Thr His Arg
        515                 520                 525

Ser Pro His Ser Gly Met Thr Thr Pro Met Ser Arg Gly Pro Glu Asp
    530                 535                 540

Val Ser Trp Pro Ser Arg Pro Ser Val Glu Lys Thr Ser Pro Pro Ser
545                 550                 555                 560

Ser Leu Val Ser Leu Ser Ala Val Thr Ser Pro Ser Pro Leu Tyr Ser
                565                 570                 575

Thr Pro Ser Glu Ser Ser His Ser Ser Pro Leu Arg Val Thr Ser Leu
                580                 585                 590

Phe Thr Pro Val Met Met Lys Thr Thr Asp Met Leu Asp Thr Ser Leu
        595                 600                 605

Glu Pro Val Thr Thr Ser Pro Pro Ser Met Asn Ile Thr Ser Asp Glu
    610                 615                 620

Ser Leu Ala Thr Ser Lys Ala Thr Met Glu Thr Glu Ala Ile Gln Leu
625                 630                 635                 640

Ser Glu Asn Thr Ala Val Thr Gln Met Gly Thr Ile Ser Ala Arg Gln
                645                 650                 655

Glu Phe Tyr Ser Ser Tyr Pro Gly Leu Pro Glu Pro Ser Lys Val Thr
            660                 665                 670

Ser Pro Val Val Thr Ser Ser Thr Ile Lys Asp Ile Val Ser Thr Thr
        675                 680                 685

Ile Pro Ala Ser Ser Glu Ile Thr Arg Ile Glu Met Glu Ser Thr Ser
    690                 695                 700

Thr Leu Thr Pro Thr Pro Arg Glu Thr Thr Ser Gln Glu Ile His
705                 710                 715                 720

Ser Ala Thr Lys Pro Ser Thr Val Pro Tyr Lys Ala Leu Thr Ser Ala
                725                 730                 735

Thr Ile Glu Asp Ser Met Thr Gln Val Met Ser Ser Arg Gly Pro
            740                 745                 750

Ser Pro Asp Gln Ser Thr Met Ser Gln Asp Ile Ser Thr Glu Val Ile
        755                 760                 765

Thr Arg Leu Ser Thr Ser Pro Ile Lys Thr Glu Ser Thr Glu Met Thr
    770                 775                 780

Ile Thr Thr Gln Thr Gly Ser Pro Gly Ala Thr Ser Arg Gly Thr Leu
785                 790                 795                 800

Thr Leu Asp Thr Ser Thr Thr Phe Met Ser Gly Thr His Ser Thr Ala
                805                 810                 815
```

-continued

```
Ser Gln Gly Phe Ser His Ser Gln Met Thr Ala Leu Met Ser Arg Thr
                820                 825                 830

Pro Gly Glu Val Pro Trp Leu Ser His Pro Ser Val Glu Ala Ser
        835                 840                 845

Ser Ala Ser Phe Ser Leu Ser Ser Pro Val Met Thr Ser Ser Pro
850                 855                 860

Val Ser Ser Thr Leu Pro Asp Ser Ile His Ser Ser Leu Pro Val
865                 870                 875                 880

Thr Ser Leu Leu Thr Ser Gly Leu Val Lys Thr Thr Glu Leu Leu Gly
                885                 890                 895

Thr Ser Ser Glu Pro Glu Thr Ser Ser Pro Pro Asn Leu Ser Ser Thr
                900                 905                 910

Ser Ala Glu Ile Leu Ala Thr Thr Glu Val Thr Thr Asp Thr Glu Lys
                915                 920                 925

Leu Glu Met Thr Asn Val Val Thr Ser Gly Tyr Thr His Glu Ser Pro
                930                 935                 940

Ser Ser Val Leu Ala Asp Ser Val Thr Thr Lys Ala Thr Ser Ser Met
945                 950                 955                 960

Gly Ile Thr Tyr Pro Thr Gly Asp Thr Asn Val Leu Thr Ser Thr Pro
                965                 970                 975

Ala Phe Ser Asp Thr Ser Arg Ile Gln Thr Lys Ser Lys Leu Ser Leu
                980                 985                 990

Thr Pro Gly Leu Met Glu Thr Ser Ile Ser Glu Glu Thr Ser Ser Ala
        995                 1000                1005

Thr Glu Lys Ser Thr Val Leu Ser Ser Val Pro Thr Gly Ala Thr
    1010                1015                1020

Thr Glu Val Ser Arg Thr Glu Ala Ile Ser Ser Ser Arg Thr Ser
    1025                1030                1035

Ile Pro Gly Pro Ala Gln Ser Thr Met Ser Ser Asp Thr Ser Met
    1040                1045                1050

Glu Thr Ile Thr Arg Ile Ser Thr Pro Leu Thr Arg Lys Glu Ser
    1055                1060                1065

Thr Asp Met Ala Ile Thr Pro Lys Thr Gly Pro Ser Gly Ala Thr
    1070                1075                1080

Ser Gln Gly Thr Phe Thr Leu Asp Ser Ser Ser Thr Ala Ser Trp
    1085                1090                1095

Pro Gly Thr His Ser Ala Thr Thr Gln Arg Phe Pro Arg Ser Val
    1100                1105                1110

Val Thr Thr Pro Met Ser Arg Gly Pro Glu Asp Val Ser Trp Pro
    1115                1120                1125

Ser Pro Leu Ser Val Glu Lys Asn Ser Pro Pro Ser Ser Leu Val
    1130                1135                1140

Ser Ser Ser Ser Val Thr Ser Pro Ser Pro Leu Tyr Ser Thr Pro
    1145                1150                1155

Ser Gly Ser Ser His Ser Ser Pro Val Pro Val Thr Ser Leu Phe
    1160                1165                1170

Thr Ser Ile Met Met Lys Ala Thr Asp Met Leu Asp Ala Ser Leu
    1175                1180                1185

Glu Pro Glu Thr Thr Ser Ala Pro Asn Met Asn Ile Thr Ser Asp
    1190                1195                1200

Glu Ser Leu Ala Ala Ser Lys Ala Thr Glu Thr Glu Ala Ile
    1205                1210                1215

His Val Phe Glu Asn Thr Ala Ala Ser His Val Glu Thr Thr Ser
    1220                1225                1230
```

```
Ala Thr Glu Glu Leu Tyr Ser Ser Pro Gly Phe Ser Glu Pro
1235                1240                1245

Thr Lys Val Ile Ser Pro Val Val Thr Ser Ser Ile Arg Asp
1250                1255                1260

Asn Met Val Ser Thr Thr Met Pro Gly Ser Ser Gly Ile Thr Arg
1265                1270                1275

Ile Glu Ile Glu Ser Met Ser Ser Leu Thr Pro Gly Leu Arg Glu
1280                1285                1290

Thr Arg Thr Ser Gln Asp Ile Thr Ser Ser Thr Glu Thr Ser Thr
1295                1300                1305

Val Leu Tyr Lys Met Pro Ser Gly Ala Thr Pro Glu Val Ser Arg
1310                1315                1320

Thr Glu Val Met Pro Ser Ser Arg Thr Ser Ile Pro Gly Pro Ala
1325                1330                1335

Gln Ser Thr Met Ser Leu Asp Ile Ser Asp Glu Val Val Thr Arg
1340                1345                1350

Leu Ser Thr Ser Pro Ile Met Thr Glu Ser Ala Glu Ile Thr Ile
1355                1360                1365

Thr Thr Gln Thr Gly Tyr Ser Leu Ala Thr Ser Gln Val Thr Leu
1370                1375                1380

Pro Leu Gly Thr Ser Met Thr Phe Leu Ser Gly Thr His Ser Thr
1385                1390                1395

Met Ser Gln Gly Leu Ser His Ser Glu Met Thr Asn Leu Met Ser
1400                1405                1410

Arg Gly Pro Glu Ser Leu Ser Trp Thr Ser Pro Arg Phe Val Glu
1415                1420                1425

Thr Thr Arg Ser Ser Ser Ser Leu Thr Ser Leu Pro Leu Thr Thr
1430                1435                1440

Ser Leu Ser Pro Val Ser Ser Thr Leu Leu Asp Ser Ser Pro Ser
1445                1450                1455

Ser Pro Leu Pro Val Thr Ser Leu Ile Leu Pro Gly Leu Val Lys
1460                1465                1470

Thr Thr Glu Val Leu Asp Thr Ser Ser Glu Pro Lys Thr Ser Ser
1475                1480                1485

Ser Pro Asn Leu Ser Ser Thr Ser Val Glu Ile Pro Ala Thr Ser
1490                1495                1500

Glu Ile Met Thr Asp Thr Glu Lys Ile His Pro Ser Ser Asn Thr
1505                1510                1515

Ala Val Ala Lys Val Arg Thr Ser Ser Ser Val His Glu Ser His
1520                1525                1530

Ser Ser Val Leu Ala Asp Ser Glu Thr Thr Ile Thr Ile Pro Ser
1535                1540                1545

Met Gly Ile Thr Ser Ala Val Glu Asp Thr Thr Val Phe Thr Ser
1550                1555                1560

Asn Pro Ala Phe Ser Glu Thr Arg Arg Ile Pro Thr Glu Pro Thr
1565                1570                1575

Phe Ser Leu Thr Pro Gly Phe Arg Glu Thr Ser Thr Ser Glu Glu
1580                1585                1590

Thr Thr Ser Ile Thr Glu Thr Ser Ala Val Leu Phe Gly Val Pro
1595                1600                1605

Thr Ser Ala Thr Thr Glu Val Ser Met Thr Glu Ile Met Ser Ser
1610                1615                1620

Asn Arg Thr His Ile Pro Asp Ser Asp Gln Ser Thr Met Ser Pro
1625                1630                1635
```

-continued

```
Asp Ile Ile Thr Glu Val Ile Thr Arg Leu Ser Ser Ser Ser Met
    1640                1645                1650
Met Ser Glu Ser Thr Gln Met Thr Ile Thr Thr Gln Lys Ser Ser
    1655                1660                1665
Pro Gly Ala Thr Ala Gln Ser Thr Leu Thr Leu Ala Thr Thr Thr
    1670                1675                1680
Ala Pro Leu Ala Arg Thr His Ser Thr Val Pro Pro Arg Phe Leu
    1685                1690                1695
His Ser Glu Met Thr Thr Leu Met Ser Arg Ser Pro Glu Asn Pro
    1700                1705                1710
Ser Trp Lys Ser Ser Pro Phe Val Glu Lys Thr Ser Ser Ser Ser
    1715                1720                1725
Ser Leu Leu Ser Leu Pro Val Thr Thr Ser Pro Ser Val Ser Ser
    1730                1735                1740
Thr Leu Pro Gln Ser Ile Pro Ser Ser Ser Phe Ser Val Thr Ser
    1745                1750                1755
Leu Leu Thr Pro Gly Met Val Lys Thr Thr Asp Thr Ser Thr Glu
    1760                1765                1770
Pro Gly Thr Ser Leu Ser Pro Asn Leu Ser Gly Thr Ser Val Glu
    1775                1780                1785
Ile Leu Ala Ala Ser Glu Val Thr Thr Asp Thr Glu Lys Ile His
    1790                1795                1800
Pro Ser Ser Ser Met Ala Val Thr Asn Val Gly Thr Thr Ser Ser
    1805                1810                1815
Gly His Glu Leu Tyr Ser Ser Val Ser Ile His Ser Glu Pro Ser
    1820                1825                1830
Lys Ala Thr Tyr Pro Val Gly Thr Pro Ser Ser Met Ala Glu Thr
    1835                1840                1845
Ser Ile Ser Thr Ser Met Pro Ala Asn Phe Glu Thr Thr Gly Phe
    1850                1855                1860
Glu Ala Glu Pro Phe Ser His Leu Thr Ser Gly Leu Arg Lys Thr
    1865                1870                1875
Asn Met Ser Leu Asp Thr Ser Ser Val Thr Pro Thr Asn Thr Pro
    1880                1885                1890
Ser Ser Pro Gly Ser Thr His Leu Leu Gln Ser Ser Lys Thr Asp
    1895                1900                1905
Phe Thr Ser Ser Ala Lys Thr Ser Ser Pro Asp Trp Pro Pro Ala
    1910                1915                1920
Ser Gln Tyr Thr Glu Ile Pro Val Asp Ile Ile Thr Pro Phe Asn
    1925                1930                1935
Ala Ser Pro Ser Ile Thr Glu Ser Thr Gly Ile Thr Ser Phe Pro
    1940                1945                1950
Glu Ser Arg Phe Thr Met Ser Val Thr Glu Ser Thr His His Leu
    1955                1960                1965
Ser Thr Asp Leu Leu Pro Ser Ala Glu Thr Ile Ser Thr Gly Thr
    1970                1975                1980
Val Met Pro Ser Leu Ser Glu Ala Met Thr Ser Phe Ala Thr Thr
    1985                1990                1995
Gly Val Pro Arg Ala Ile Ser Gly Ser Gly Ser Pro Phe Ser Arg
    2000                2005                2010
Thr Glu Ser Gly Pro Gly Asp Ala Thr Leu Ser Thr Ile Ala Glu
    2015                2020                2025
Ser Leu Pro Ser Ser Thr Pro Val Pro Phe Ser Ser Ser Thr Phe
    2030                2035                2040
```

```
Thr  Thr  Thr  Asp  Ser  Ser  Thr  Ile  Pro  Ala  Leu  His  Glu  Ile  Thr
2045                2050                     2055

Ser  Ser  Ser  Ala  Thr  Pro  Tyr  Arg  Val  Asp  Thr  Ser  Leu  Gly  Thr
2060                2065                     2070

Glu  Ser  Ser  Thr  Thr  Glu  Gly  Arg  Leu  Val  Met  Val  Ser  Thr  Leu
2075                2080                     2085

Asp  Thr  Ser  Ser  Gln  Pro  Gly  Arg  Thr  Ser  Ser  Pro  Ile  Leu
2090                2095                     2100

Asp  Thr  Arg  Met  Thr  Glu  Ser  Val  Glu  Leu  Gly  Thr  Val  Thr  Ser
2105                2110                     2115

Ala  Tyr  Gln  Val  Pro  Ser  Leu  Ser  Thr  Arg  Leu  Thr  Arg  Thr  Asp
2120                2125                     2130

Gly  Ile  Met  Glu  His  Ile  Thr  Lys  Ile  Pro  Asn  Glu  Ala  Ala  His
2135                2140                     2145

Arg  Gly  Thr  Ile  Arg  Pro  Val  Lys  Gly  Pro  Gln  Thr  Ser  Thr  Ser
2150                2155                     2160

Pro  Ala  Ser  Pro  Lys  Gly  Leu  His  Thr  Gly  Gly  Thr  Lys  Arg  Met
2165                2170                     2175

Glu  Thr  Thr  Thr  Thr  Ala  Leu  Lys  Thr  Thr  Thr  Thr  Ala  Leu  Lys
2180                2185                     2190

Thr  Thr  Ser  Arg  Ala  Thr  Leu  Thr  Thr  Ser  Val  Tyr  Thr  Pro  Thr
2195                2200                     2205

Leu  Gly  Thr  Leu  Thr  Pro  Leu  Asn  Ala  Ser  Met  Gln  Met  Ala  Ser
2210                2215                     2220

Thr  Ile  Pro  Thr  Glu  Met  Met  Ile  Thr  Thr  Pro  Tyr  Val  Phe  Pro
2225                2230                     2235

Asp  Val  Pro  Glu  Thr  Thr  Ser  Ser  Leu  Ala  Thr  Ser  Leu  Gly  Ala
2240                2245                     2250

Glu  Thr  Ser  Thr  Ala  Leu  Pro  Arg  Thr  Thr  Pro  Ser  Val  Phe  Asn
2255                2260                     2265

Arg  Glu  Ser  Glu  Thr  Thr  Ala  Ser  Leu  Val  Ser  Arg  Ser  Gly  Ala
2270                2275                     2280

Glu  Arg  Ser  Pro  Val  Ile  Gln  Thr  Leu  Asp  Val  Ser  Ser  Ser  Glu
2285                2290                     2295

Pro  Asp  Thr  Thr  Ala  Ser  Trp  Val  Ile  His  Pro  Ala  Glu  Thr  Ile
2300                2305                     2310

Pro  Thr  Val  Ser  Lys  Thr  Thr  Pro  Asn  Phe  Phe  His  Ser  Glu  Leu
2315                2320                     2325

Asp  Thr  Val  Ser  Ser  Thr  Ala  Thr  Ser  His  Gly  Ala  Asp  Val  Ser
2330                2335                     2340

Ser  Ala  Ile  Pro  Thr  Asn  Ile  Ser  Pro  Ser  Glu  Leu  Asp  Ala  Leu
2345                2350                     2355

Thr  Pro  Leu  Val  Thr  Ile  Ser  Gly  Thr  Asp  Thr  Ser  Thr  Thr  Phe
2360                2365                     2370

Pro  Thr  Leu  Thr  Lys  Ser  Pro  His  Glu  Thr  Glu  Thr  Arg  Thr  Thr
2375                2380                     2385

Trp  Leu  Thr  His  Pro  Ala  Glu  Thr  Ser  Ser  Thr  Ile  Pro  Arg  Thr
2390                2395                     2400

Ile  Pro  Asn  Phe  Ser  His  His  Glu  Ser  Asp  Ala  Thr  Pro  Ser  Ile
2405                2410                     2415

Ala  Thr  Ser  Pro  Gly  Ala  Glu  Thr  Ser  Ser  Ala  Ile  Pro  Ile  Met
2420                2425                     2430

Thr  Val  Ser  Pro  Gly  Ala  Glu  Asp  Leu  Val  Thr  Ser  Gln  Val  Thr
2435                2440                     2445
```

```
Ser Ser Gly Thr Asp Arg Asn Met Thr Ile Pro Thr Leu Thr Leu
    2450                2455                2460

Ser Pro Gly Glu Pro Lys Thr Ile Ala Ser Leu Val Thr His Pro
    2465                2470                2475

Glu Ala Gln Thr Ser Ser Ala Ile Pro Thr Ser Thr Ile Ser Pro
    2480                2485                2490

Ala Val Ser Arg Leu Val Thr Ser Met Val Thr Ser Leu Ala Ala
    2495                2500                2505

Lys Thr Ser Thr Thr Asn Arg Ala Leu Thr Asn Ser Pro Gly Glu
    2510                2515                2520

Pro Ala Thr Thr Val Ser Leu Val Thr His Ser Ala Gln Thr Ser
    2525                2530                2535

Pro Thr Val Pro Trp Thr Thr Ser Ile Phe Phe His Ser Lys Ser
    2540                2545                2550

Asp Thr Thr Pro Ser Met Thr Thr Ser His Gly Ala Glu Ser Ser
    2555                2560                2565

Ser Ala Val Pro Thr Pro Thr Val Ser Thr Glu Val Pro Gly Val
    2570                2575                2580

Val Thr Pro Leu Val Thr Ser Ser Arg Ala Val Ile Ser Thr Thr
    2585                2590                2595

Ile Pro Ile Leu Thr Leu Ser Pro Gly Glu Pro Glu Thr Thr Pro
    2600                2605                2610

Ser Met Ala Thr Ser His Gly Glu Ala Ser Ser Ala Ile Pro
    2615                2620                2625

Thr Pro Thr Val Ser Pro Gly Val Pro Gly Val Val Thr Ser Leu
    2630                2635                2640

Val Thr Ser Ser Arg Ala Val Thr Ser Thr Thr Ile Pro Ile Leu
    2645                2650                2655

Thr Phe Ser Leu Gly Glu Pro Glu Thr Thr Pro Ser Met Ala Thr
    2660                2665                2670

Ser His Gly Thr Glu Ala Gly Ser Ala Val Pro Thr Val Leu Pro
    2675                2680                2685

Glu Val Pro Gly Met Val Thr Ser Leu Val Ala Ser Ser Arg Ala
    2690                2695                2700

Val Thr Ser Thr Thr Leu Pro Thr Leu Thr Leu Ser Pro Gly Glu
    2705                2710                2715

Pro Glu Thr Thr Pro Ser Met Ala Thr Ser His Gly Ala Glu Ala
    2720                2725                2730

Ser Ser Thr Val Pro Thr Val Ser Pro Glu Val Pro Gly Val Val
    2735                2740                2745

Thr Ser Leu Val Thr Ser Ser Gly Val Asn Ser Thr Ser Ile
    2750                2755                2760

Pro Thr Leu Ile Leu Ser Pro Gly Glu Leu Glu Thr Thr Pro Ser
    2765                2770                2775

Met Ala Thr Ser His Gly Ala Glu Ala Ser Ser Ala Val Pro Thr
    2780                2785                2790

Pro Thr Val Ser Pro Gly Val Ser Gly Val Val Thr Pro Leu Val
    2795                2800                2805

Thr Ser Ser Arg Ala Val Thr Ser Thr Thr Ile Pro Ile Leu Thr
    2810                2815                2820

Leu Ser Ser Ser Glu Pro Glu Thr Thr Pro Ser Met Ala Thr Ser
    2825                2830                2835

His Gly Val Glu Ala Ser Ser Ala Val Leu Thr Val Ser Pro Glu
    2840                2845                2850
```

-continued

Val Pro Gly Met Val Thr Phe Leu Val Thr Ser Ser Arg Ala Val
2855            2860                2865

Thr Ser Thr Thr Ile Pro Thr Leu Thr Ile Ser Ser Asp Glu Pro
2870            2875                2880

Glu Thr Thr Thr Ser Leu Val Thr His Ser Glu Ala Lys Met Ile
2885            2890                2895

Ser Ala Ile Pro Thr Leu Gly Val Ser Pro Thr Val Gln Gly Leu
2900            2905                2910

Val Thr Ser Leu Val Thr Ser Ser Gly Ser Glu Thr Ser Ala Phe
2915            2920                2925

Ser Asn Leu Thr Val Ala Ser Ser Gln Pro Glu Thr Ile Asp Ser
2930            2935                2940

Trp Val Ala His Pro Gly Thr Glu Ala Ser Ser Val Val Pro Thr
2945            2950                2955

Leu Thr Val Ser Thr Gly Glu Pro Phe Thr Asn Ile Ser Leu Val
2960            2965                2970

Thr His Pro Ala Glu Ser Ser Thr Leu Pro Arg Thr Thr Ser
2975            2980                2985

Arg Phe Ser His Ser Glu Leu Asp Thr Met Pro Ser Thr Val Thr
2990            2995                3000

Ser Pro Glu Ala Glu Ser Ser Ala Ile Ser Thr Thr Ile Ser
3005            3010                3015

Pro Gly Ile Pro Gly Val Leu Thr Ser Leu Val Thr Ser Ser Gly
3020            3025                3030

Arg Asp Ile Ser Ala Thr Phe Pro Thr Val Pro Glu Ser Pro His
3035            3040                3045

Glu Ser Glu Ala Thr Ala Ser Trp Val Thr His Pro Ala Val Thr
3050            3055                3060

Ser Thr Thr Val Pro Arg Thr Thr Pro Asn Tyr Ser His Ser Glu
3065            3070                3075

Pro Asp Thr Thr Pro Ser Ile Ala Thr Ser Pro Gly Ala Glu Ala
3080            3085                3090

Thr Ser Asp Phe Pro Thr Ile Thr Val Ser Pro Asp Val Pro Asp
3095            3100                3105

Met Val Thr Ser Gln Val Thr Ser Ser Gly Thr Asp Thr Ser Ile
3110            3115                3120

Thr Ile Pro Thr Leu Thr Leu Ser Ser Gly Glu Pro Glu Thr Thr
3125            3130                3135

Thr Ser Phe Ile Thr Tyr Ser Glu Thr His Thr Ser Ser Ala Ile
3140            3145                3150

Pro Thr Leu Pro Val Ser Pro Asp Ala Ser Lys Met Leu Thr Ser
3155            3160                3165

Leu Val Ile Ser Ser Gly Thr Asp Ser Thr Thr Thr Phe Pro Thr
3170            3175                3180

Leu Thr Glu Thr Pro Tyr Glu Pro Glu Thr Thr Ala Ile Gln Leu
3185            3190                3195

Ile His Pro Ala Glu Thr Asn Thr Met Val Pro Arg Thr Thr Pro
3200            3205                3210

Lys Phe Ser His Ser Lys Ser Asp Thr Thr Leu Pro Val Ala Ile
3215            3220                3225

Thr Ser Pro Gly Pro Glu Ala Ser Ser Ala Val Ser Thr Thr Thr
3230            3235                3240

Ile Ser Pro Asp Met Ser Asp Leu Val Thr Ser Leu Val Pro Ser
3245            3250                3255

```
Ser Gly Thr Asp Thr Ser Thr Thr Phe Pro Thr Leu Ser Glu Thr
            3260                3265                3270

Pro Tyr Glu Pro Glu Thr Thr Ala Thr Trp Leu Thr His Pro Ala
    3275                3280                3285

Glu Thr Ser Thr Thr Val Ser Gly Thr Ile Pro Asn Phe Ser His
        3290                3295                3300

Arg Gly Ser Asp Thr Ala Pro Ser Met Val Thr Ser Pro Gly Val
    3305                3310                3315

Asp Thr Arg Ser Gly Val Pro Thr Thr Ile Pro Pro Ser Ile
        3320                3325                3330

Pro Gly Val Val Thr Ser Gln Val Thr Ser Ser Ala Thr Asp Thr
    3335                3340                3345

Ser Thr Ala Ile Pro Thr Leu Thr Pro Ser Pro Gly Glu Pro Glu
        3350                3355                3360

Thr Thr Ala Ser Ser Ala Thr His Pro Gly Thr Gln Thr Gly Phe
    3365                3370                3375

Thr Val Pro Ile Arg Thr Val Pro Ser Ser Glu Pro Asp Thr Met
        3380                3385                3390

Ala Ser Trp Val Thr His Pro Pro Gln Thr Ser Thr Pro Val Ser
    3395                3400                3405

Arg Thr Thr Ser Ser Phe Ser His Ser Ser Pro Asp Ala Thr Pro
    3410                3415                3420

Val Met Ala Thr Ser Pro Arg Thr Glu Ala Ser Ser Ala Val Leu
    3425                3430                3435

Thr Thr Ile Ser Pro Gly Ala Pro Glu Met Val Thr Ser Gln Ile
    3440                3445                3450

Thr Ser Ser Gly Ala Ala Thr Ser Thr Thr Val Pro Thr Leu Thr
    3455                3460                3465

His Ser Pro Gly Met Pro Glu Thr Thr Ala Leu Leu Ser Thr His
    3470                3475                3480

Pro Arg Thr Glu Thr Ser Lys Thr Phe Pro Ala Ser Thr Val Phe
    3485                3490                3495

Pro Gln Val Ser Glu Thr Thr Ala Ser Leu Thr Ile Arg Pro Gly
    3500                3505                3510

Ala Glu Thr Ser Thr Ala Leu Pro Thr Gln Thr Thr Ser Ser Leu
    3515                3520                3525

Phe Thr Leu Leu Val Thr Gly Thr Ser Arg Val Asp Leu Ser Pro
    3530                3535                3540

Thr Ala Ser Pro Gly Val Ser Ala Lys Thr Ala Pro Leu Ser Thr
    3545                3550                3555

His Pro Gly Thr Glu Thr Ser Thr Met Ile Pro Thr Ser Thr Leu
    3560                3565                3570

Ser Leu Gly Leu Leu Glu Thr Thr Gly Leu Leu Ala Thr Ser Ser
    3575                3580                3585

Ser Ala Glu Thr Ser Thr Ser Thr Leu Thr Leu Thr Val Ser Pro
    3590                3595                3600

Ala Val Ser Gly Leu Ser Ser Ala Ser Ile Thr Thr Asp Lys Pro
    3605                3610                3615

Gln Thr Val Thr Ser Trp Asn Thr Glu Thr Ser Pro Ser Val Thr
    3620                3625                3630

Ser Val Gly Pro Pro Glu Phe Ser Arg Thr Val Thr Gly Thr Thr
    3635                3640                3645

Met Thr Leu Ile Pro Ser Glu Met Pro Thr Pro Pro Lys Thr Ser
    3650                3655                3660
```

-continued

His Gly Glu Gly Val Ser Pro Thr Thr Ile Leu Arg Thr Thr Met
3665                3670                     3675

Val Glu Ala Thr Asn Leu Ala Thr Thr Gly Ser Ser Pro Thr Val
3680                3685                     3690

Ala Lys Thr Thr Thr Thr Phe Asn Thr Leu Ala Gly Ser Leu Phe
3695                3700                     3705

Thr Pro Leu Thr Thr Pro Gly Met Ser Thr Leu Ala Ser Glu Ser
3710                3715                     3720

Val Thr Ser Arg Thr Ser Tyr Asn His Arg Ser Trp Ile Ser Thr
3725                3730                     3735

Thr Ser Ser Tyr Asn Arg Arg Tyr Trp Thr Pro Ala Thr Ser Thr
3740                3745                     3750

Pro Val Thr Ser Thr Phe Ser Pro Gly Ile Ser Thr Ser Ser Ile
3755                3760                     3765

Pro Ser Ser Thr Ala Ala Thr Val Pro Phe Met Val Pro Phe Thr
3770                3775                     3780

Leu Asn Phe Thr Ile Thr Asn Leu Gln Tyr Glu Glu Asp Met Arg
3785                3790                     3795

His Pro Gly Ser Arg Lys Phe Asn Ala Thr Glu Arg Glu Leu Gln
3800                3805                     3810

Gly Leu Leu Lys Pro Leu Phe Arg Asn Ser Ser Leu Glu Tyr Leu
3815                3820                     3825

Tyr Ser Gly Cys Arg Leu Ala Ser Leu Arg Pro Glu Lys Asp Ser
3830                3835                     3840

Ser Ala Thr Ala Val Asp Ala Ile Cys Thr His Arg Pro Asp Pro
3845                3850                     3855

Glu Asp Leu Gly Leu Asp Arg Glu Arg Leu Tyr Trp Glu Leu Ser
3860                3865                     3870

Asn Leu Thr Asn Gly Ile Gln Glu Leu Gly Pro Tyr Thr Leu Asp
3875                3880                     3885

Arg Asn Ser Leu Tyr Val Asn Gly Phe Thr His Arg Ser Ser Met
3890                3895                     3900

Pro Thr Thr Ser Thr Pro Gly Thr Ser Thr Val Asp Val Gly Thr
3905                3910                     3915

Ser Gly Thr Pro Ser Ser Ser Pro Ser Pro Thr Thr Ala Gly Pro
3920                3925                     3930

Leu Leu Met Pro Phe Thr Leu Asn Phe Thr Ile Thr Asn Leu Gln
3935                3940                     3945

Tyr Glu Glu Asp Met Arg Arg Thr Gly Ser Arg Lys Phe Asn Thr
3950                3955                     3960

Met Glu Ser Val Leu Gln Gly Leu Leu Lys Pro Leu Phe Lys Asn
3965                3970                     3975

Thr Ser Val Gly Pro Leu Tyr Ser Gly Cys Arg Leu Thr Leu Leu
3980                3985                     3990

Arg Pro Glu Lys Asp Gly Ala Ala Thr Gly Val Asp Ala Ile Cys
3995                4000                     4005

Thr His Arg Leu Asp Pro Lys Ser Pro Gly Leu Asn Arg Glu Gln
4010                4015                     4020

Leu Tyr Trp Glu Leu Ser Lys Leu Thr Asn Asp Ile Glu Glu Leu
4025                4030                     4035

Gly Pro Tyr Thr Leu Asp Arg Asn Ser Leu Tyr Val Asn Gly Phe
4040                4045                     4050

Thr His Gln Ser Ser Val Ser Thr Thr Ser Thr Pro Gly Thr Ser
4055                4060                     4065

-continued

Thr Val Asp Leu Arg Thr Ser Gly Thr Pro Ser Ser Leu Ser Ser
4070            4075                4080

Pro Thr Ile Met Ala Ala Gly Pro Leu Leu Val Pro Phe Thr Leu
4085            4090                4095

Asn Phe Thr Ile Thr Asn Leu Gln Tyr Gly Glu Asp Met Gly His
4100            4105                4110

Pro Gly Ser Arg Lys Phe Asn Thr Thr Glu Arg Val Leu Gln Gly
4115            4120                4125

Leu Leu Gly Pro Ile Phe Lys Asn Thr Ser Val Gly Pro Leu Tyr
4130            4135                4140

Ser Gly Cys Arg Leu Thr Ser Leu Arg Ser Glu Lys Asp Gly Ala
4145            4150                4155

Ala Thr Gly Val Asp Ala Ile Cys Ile His His Leu Asp Pro Lys
4160            4165                4170

Ser Pro Gly Leu Asn Arg Glu Arg Leu Tyr Trp Glu Leu Ser Gln
4175            4180                4185

Leu Thr Asn Gly Ile Lys Glu Leu Gly Pro Tyr Thr Leu Asp Arg
4190            4195                4200

Asn Ser Leu Tyr Val Asn Gly Phe Thr His Arg Thr Ser Val Pro
4205            4210                4215

Thr Thr Ser Thr Pro Gly Thr Ser Thr Val Asp Leu Gly Thr Ser
4220            4225                4230

Gly Thr Pro Phe Ser Leu Pro Ser Pro Ala Thr Ala Gly Pro Leu
4235            4240                4245

Leu Val Leu Phe Thr Leu Asn Phe Thr Ile Thr Asn Leu Lys Tyr
4250            4255                4260

Glu Glu Asp Met His Arg Pro Gly Ser Arg Lys Phe Asn Thr Thr
4265            4270                4275

Glu Arg Val Leu Gln Thr Leu Val Gly Pro Met Phe Lys Asn Thr
4280            4285                4290

Ser Val Gly Leu Leu Tyr Ser Gly Cys Arg Leu Thr Leu Leu Arg
4295            4300                4305

Ser Glu Lys Asp Gly Ala Ala Thr Gly Val Asp Ala Ile Cys Thr
4310            4315                4320

His Arg Leu Asp Pro Lys Ser Pro Gly Val Asp Arg Glu Gln Leu
4325            4330                4335

Tyr Trp Glu Leu Ser Gln Leu Thr Asn Gly Ile Lys Glu Leu Gly
4340            4345                4350

Pro Tyr Thr Leu Asp Arg Asn Ser Leu Tyr Val Asn Gly Phe Thr
4355            4360                4365

His Trp Ile Pro Val Pro Thr Ser Ser Thr Pro Gly Thr Ser Thr
4370            4375                4380

Val Asp Leu Gly Ser Gly Thr Pro Ser Ser Leu Pro Ser Pro Thr
4385            4390                4395

Ser Ala Thr Ala Gly Pro Leu Leu Val Pro Phe Thr Leu Asn Phe
4400            4405                4410

Thr Ile Thr Asn Leu Lys Tyr Glu Glu Asp Met His Cys Pro Gly
4415            4420                4425

Ser Arg Lys Phe Asn Thr Thr Glu Arg Val Leu Gln Ser Leu Leu
4430            4435                4440

Gly Pro Met Phe Lys Asn Thr Ser Val Gly Pro Leu Tyr Ser Gly
4445            4450                4455

Cys Arg Leu Thr Leu Leu Arg Ser Glu Lys Asp Gly Ala Ala Thr
4460            4465                4470

-continued

| | | | | | | | | | | | |
|---|---|---|---|---|---|---|---|---|---|---|---|
|Gly|Val|Asp|Ala|Ile|Cys|Thr|His|Arg|Leu|Asp|Pro|Lys|Ser|Pro|
|4475| | | | |4480| | | | |4485| | | | |

Gly Val Asp Arg Glu Gln Leu Tyr Trp Glu Leu Ser Gln Leu Thr
    4490            4495            4500

Asn Gly Ile Lys Glu Leu Gly Pro Tyr Thr Leu Asp Arg Asn Ser
    4505            4510            4515

Leu Tyr Val Asn Gly Phe Thr His Gln Thr Ser Ala Pro Asn Thr
    4520            4525            4530

Ser Thr Pro Gly Thr Ser Thr Val Asp Leu Gly Thr Ser Gly Thr
    4535            4540            4545

Pro Ser Ser Leu Pro Ser Pro Thr Ser Ala Gly Pro Leu Leu Val
    4550            4555            4560

Pro Phe Thr Leu Asn Phe Thr Ile Thr Asn Leu Gln Tyr Glu Glu
    4565            4570            4575

Asp Met His His Pro Gly Ser Arg Lys Phe Asn Thr Thr Glu Arg
    4580            4585            4590

Val Leu Gln Gly Leu Leu Gly Pro Met Phe Lys Asn Thr Ser Val
    4595            4600            4605

Gly Leu Leu Tyr Ser Gly Cys Arg Leu Thr Leu Leu Arg Pro Glu
    4610            4615            4620

Lys Asn Gly Ala Ala Thr Gly Met Asp Ala Ile Cys Ser His Arg
    4625            4630            4635

Leu Asp Pro Lys Ser Pro Gly Leu Asn Arg Glu Gln Leu Tyr Trp
    4640            4645            4650

Glu Leu Ser Gln Leu Thr His Gly Ile Lys Glu Leu Gly Pro Tyr
    4655            4660            4665

Thr Leu Asp Arg Asn Ser Leu Tyr Val Asn Gly Phe Thr His Arg
    4670            4675            4680

Ser Ser Val Ala Pro Thr Ser Thr Pro Gly Thr Ser Thr Val Asp
    4685            4690            4695

Leu Gly Thr Ser Gly Thr Pro Ser Ser Leu Pro Ser Pro Thr Thr
    4700            4705            4710

Ala Val Pro Leu Leu Val Pro Phe Thr Leu Asn Phe Thr Ile Thr
    4715            4720            4725

Asn Leu Gln Tyr Gly Glu Asp Met Arg His Pro Gly Ser Arg Lys
    4730            4735            4740

Phe Asn Thr Thr Glu Arg Val Leu Gln Gly Leu Leu Gly Pro Leu
    4745            4750            4755

Phe Lys Asn Ser Ser Val Gly Pro Leu Tyr Ser Gly Cys Arg Leu
    4760            4765            4770

Ile Ser Leu Arg Ser Glu Lys Asp Gly Ala Ala Thr Gly Val Asp
    4775            4780            4785

Ala Ile Cys Thr His His Leu Asn Pro Gln Ser Pro Gly Leu Asp
    4790            4795            4800

Arg Glu Gln Leu Tyr Trp Gln Leu Ser Gln Met Thr Asn Gly Ile
    4805            4810            4815

Lys Glu Leu Gly Pro Tyr Thr Leu Asp Arg Asn Ser Leu Tyr Val
    4820            4825            4830

Asn Gly Phe Thr His Arg Ser Ser Gly Leu Thr Thr Ser Thr Pro
    4835            4840            4845

Trp Thr Ser Thr Val Asp Leu Gly Thr Ser Gly Thr Pro Ser Pro
    4850            4855            4860

Val Pro Ser Pro Thr Thr Ala Gly Pro Leu Leu Val Pro Phe Thr
    4865            4870            4875

-continued

Leu Asn Phe Thr Ile Thr Asn Leu Gln Tyr Glu Glu Asp Met His
4880                    4885                4890

Arg Pro Gly Ser Arg Lys Phe Asn Ala Thr Glu Arg Val Leu Gln
4895                    4900                4905

Gly Leu Leu Ser Pro Ile Phe Lys Asn Ser Ser Val Gly Pro Leu
4910                    4915                4920

Tyr Ser Gly Cys Arg Leu Thr Ser Leu Arg Pro Glu Lys Asp Gly
4925                    4930                4935

Ala Ala Thr Gly Met Asp Ala Val Cys Leu Tyr His Pro Asn Pro
4940                    4945                4950

Lys Arg Pro Gly Leu Asp Arg Glu Gln Leu Tyr Trp Glu Leu Ser
4955                    4960                4965

Gln Leu Thr His Asn Ile Thr Glu Leu Gly Pro Tyr Ser Leu Asp
4970                    4975                4980

Arg Asp Ser Leu Tyr Val Asn Gly Phe Thr His Gln Asn Ser Val
4985                    4990                4995

Pro Thr Thr Ser Thr Pro Gly Thr Ser Thr Val Tyr Trp Ala Thr
5000                    5005                5010

Thr Gly Thr Pro Ser Ser Phe Pro Gly His Thr Glu Pro Gly Pro
5015                    5020                5025

Leu Leu Ile Pro Phe Thr Phe Asn Phe Thr Ile Thr Asn Leu His
5030                    5035                5040

Tyr Glu Glu Asn Met Gln His Pro Gly Ser Arg Lys Phe Asn Thr
5045                    5050                5055

Thr Glu Arg Val Leu Gln Gly Leu Leu Lys Pro Leu Phe Lys Asn
5060                    5065                5070

Thr Ser Val Gly Pro Leu Tyr Ser Gly Cys Arg Leu Thr Leu Leu
5075                    5080                5085

Arg Pro Glu Lys Gln Glu Ala Ala Thr Gly Val Asp Thr Ile Cys
5090                    5095                5100

Thr His Arg Val Asp Pro Ile Gly Pro Gly Leu Asp Arg Glu Arg
5105                    5110                5115

Leu Tyr Trp Glu Leu Ser Gln Leu Thr Asn Ser Ile Thr Glu Leu
5120                    5125                5130

Gly Pro Tyr Thr Leu Asp Arg Asp Ser Leu Tyr Val Asn Gly Phe
5135                    5140                5145

Asn Pro Trp Ser Ser Val Pro Thr Thr Ser Thr Pro Gly Thr Ser
5150                    5155                5160

Thr Val His Leu Ala Thr Ser Gly Thr Pro Ser Ser Leu Pro Gly
5165                    5170                5175

His Thr Ala Pro Val Pro Leu Leu Ile Pro Phe Thr Leu Asn Phe
5180                    5185                5190

Thr Ile Thr Asn Leu His Tyr Glu Glu Asn Met Gln His Pro Gly
5195                    5200                5205

Ser Arg Lys Phe Asn Thr Thr Glu Arg Val Leu Gln Gly Leu Leu
5210                    5215                5220

Lys Pro Leu Phe Lys Ser Thr Ser Val Gly Pro Leu Tyr Ser Gly
5225                    5230                5235

Cys Arg Leu Thr Leu Leu Arg Pro Glu Lys His Gly Ala Ala Thr
5240                    5245                5250

Gly Val Asp Ala Ile Cys Thr Leu Arg Leu Asp Pro Thr Gly Pro
5255                    5260                5265

Gly Leu Asp Arg Glu Arg Leu Tyr Trp Glu Leu Ser Gln Leu Thr
5270                    5275                5280

```
-continued

Asn Ser Val Thr Glu Leu Gly Pro Tyr Thr Leu Asp Arg Asp Ser
5285                5290                5295

Leu Tyr Val Asn Gly Phe Thr His Arg Ser Ser Val Pro Thr Thr
5300                5305                5310

Ser Ile Pro Gly Thr Ser Ala Val His Leu Glu Thr Ser Gly Thr
5315                5320                5325

Pro Ala Ser Leu Pro Gly His Thr Ala Pro Gly Pro Leu Leu Val
5330                5335                5340

Pro Phe Thr Leu Asn Phe Thr Ile Thr Asn Leu Gln Tyr Glu Glu
5345                5350                5355

Asp Met Arg His Pro Gly Ser Arg Lys Phe Asn Thr Thr Glu Arg
5360                5365                5370

Val Leu Gln Gly Leu Leu Lys Pro Leu Phe Lys Ser Thr Ser Val
5375                5380                5385

Gly Pro Leu Tyr Ser Gly Cys Arg Leu Thr Leu Leu Arg Pro Glu
5390                5395                5400

Lys Arg Gly Ala Ala Thr Gly Val Asp Thr Ile Cys Thr His Arg
5405                5410                5415

Leu Asp Pro Leu Asn Pro Gly Leu Asp Arg Glu Gln Leu Tyr Trp
5420                5425                5430

Glu Leu Ser Lys Leu Thr Arg Gly Ile Ile Glu Leu Gly Pro Tyr
5435                5440                5445

Leu Leu Asp Arg Gly Ser Leu Tyr Val Asn Gly Phe Thr His Arg
5450                5455                5460

Asn Phe Val Pro Ile Thr Ser Thr Pro Gly Thr Ser Thr Val His
5465                5470                5475

Leu Gly Thr Ser Glu Thr Pro Ser Ser Leu Pro Arg Pro Ile Val
5480                5485                5490

Pro Gly Pro Leu Leu Val Pro Phe Thr Leu Asn Phe Thr Ile Thr
5495                5500                5505

Asn Leu Gln Tyr Glu Glu Ala Met Arg His Pro Gly Ser Arg Lys
5510                5515                5520

Phe Asn Thr Thr Glu Arg Val Leu Gln Gly Leu Leu Arg Pro Leu
5525                5530                5535

Phe Lys Asn Thr Ser Ile Gly Pro Leu Tyr Ser Ser Cys Arg Leu
5540                5545                5550

Thr Leu Leu Arg Pro Glu Lys Asp Lys Ala Ala Thr Arg Val Asp
5555                5560                5565

Ala Ile Cys Thr His His Pro Asp Pro Gln Ser Pro Gly Leu Asn
5570                5575                5580

Arg Glu Gln Leu Tyr Trp Glu Leu Ser Gln Leu Thr His Gly Ile
5585                5590                5595

Thr Glu Leu Gly Pro Tyr Thr Leu Asp Arg Asp Ser Leu Tyr Val
5600                5605                5610

Asp Gly Phe Thr His Trp Ser Pro Ile Pro Thr Thr Ser Thr Pro
5615                5620                5625

Gly Thr Ser Ile Val Asn Leu Gly Thr Ser Gly Ile Pro Pro Ser
5630                5635                5640

Leu Pro Glu Thr Thr Ala Thr Gly Pro Leu Leu Val Pro Phe Thr
5645                5650                5655

Leu Asn Phe Thr Ile Thr Asn Leu Gln Tyr Glu Glu Asn Met Gly
5660                5665                5670

His Pro Gly Ser Arg Lys Phe Asn Ile Thr Glu Ser Val Leu Gln
5675                5680                5685
```

| | | | | | | | | | | |
|---|---|---|---|---|---|---|---|---|---|---|
|Gly|Leu|Leu|Lys|Pro|Leu|Phe|Lys|Ser|Thr|Ser|Val|Gly|Pro|Leu|
| |5690| | | |5695| | | |5700| | | | | |

Gly Leu Leu Lys Pro Leu Phe Lys Ser Thr Ser Val Gly Pro Leu
    5690                5695                5700

Tyr Ser Gly Cys Arg Leu Thr Leu Leu Arg Pro Glu Lys Asp Gly
    5705                5710                5715

Val Ala Thr Arg Val Asp Ala Ile Cys Thr His Arg Pro Asp Pro
    5720                5725                5730

Lys Ile Pro Gly Leu Asp Arg Gln Gln Leu Tyr Trp Glu Leu Ser
    5735                5740                5745

Gln Leu Thr His Ser Ile Thr Glu Leu Gly Pro Tyr Thr Leu Asp
    5750                5755                5760

Arg Asp Ser Leu Tyr Val Asn Gly Phe Thr Gln Arg Ser Ser Val
    5765                5770                5775

Pro Thr Thr Ser Thr Pro Gly Thr Phe Thr Val Gln Pro Glu Thr
    5780                5785                5790

Ser Glu Thr Pro Ser Ser Leu Pro Gly Pro Thr Ala Thr Gly Pro
    5795                5800                5805

Val Leu Leu Pro Phe Thr Leu Asn Phe Thr Ile Ile Asn Leu Gln
    5810                5815                5820

Tyr Glu Glu Asp Met His Arg Pro Gly Ser Arg Lys Phe Asn Thr
    5825                5830                5835

Thr Glu Arg Val Leu Gln Gly Leu Leu Met Pro Leu Phe Lys Asn
    5840                5845                5850

Thr Ser Val Ser Ser Leu Tyr Ser Gly Cys Arg Leu Thr Leu Leu
    5855                5860                5865

Arg Pro Glu Lys Asp Gly Ala Ala Thr Arg Val Asp Ala Val Cys
    5870                5875                5880

Thr His Arg Pro Asp Pro Lys Ser Pro Gly Leu Asp Arg Glu Arg
    5885                5890                5895

Leu Tyr Trp Lys Leu Ser Gln Leu Thr His Gly Ile Thr Glu Leu
    5900                5905                5910

Gly Pro Tyr Thr Leu Asp Arg His Ser Leu Tyr Val Asn Gly Phe
    5915                5920                5925

Thr His Gln Ser Ser Met Thr Thr Thr Arg Thr Pro Asp Thr Ser
    5930                5935                5940

Thr Met His Leu Ala Thr Ser Arg Thr Pro Ala Ser Leu Ser Gly
    5945                5950                5955

Pro Thr Thr Ala Ser Pro Leu Leu Val Leu Phe Thr Ile Asn Phe
    5960                5965                5970

Thr Ile Thr Asn Leu Arg Tyr Glu Glu Asn Met His His Pro Gly
    5975                5980                5985

Ser Arg Lys Phe Asn Thr Thr Glu Arg Val Leu Gln Gly Leu Leu
    5990                5995                6000

Arg Pro Val Phe Lys Asn Thr Ser Val Gly Pro Leu Tyr Ser Gly
    6005                6010                6015

Cys Arg Leu Thr Leu Leu Arg Pro Lys Lys Asp Gly Ala Ala Thr
    6020                6025                6030

Lys Val Asp Ala Ile Cys Thr Tyr Arg Pro Asp Pro Lys Ser Pro
    6035                6040                6045

Gly Leu Asp Arg Glu Gln Leu Tyr Trp Glu Leu Ser Gln Leu Thr
    6050                6055                6060

His Ser Ile Thr Glu Leu Gly Pro Tyr Thr Leu Asp Arg Asp Ser
    6065                6070                6075

Leu Tyr Val Asn Gly Phe Thr Gln Arg Ser Ser Val Pro Thr Thr
    6080                6085                6090

-continued

```
Ser Ile Pro Gly Thr Pro Thr Val Asp Leu Gly Thr Ser Gly Thr
6095                6100                          6105

Pro Val Ser Lys Pro Gly Pro Ser Ala Ala Ser Pro Leu Leu Val
6110                6115                          6120

Leu Phe Thr Leu Asn Phe Thr Ile Thr Asn Leu Arg Tyr Glu Glu
6125                6130                          6135

Asn Met Gln His Pro Gly Ser Arg Lys Phe Asn Thr Thr Glu Arg
6140                6145                          6150

Val Leu Gln Gly Leu Leu Arg Ser Leu Phe Lys Ser Thr Ser Val
6155                6160                          6165

Gly Pro Leu Tyr Ser Gly Cys Arg Leu Thr Leu Leu Arg Pro Glu
6170                6175                          6180

Lys Asp Gly Thr Ala Thr Gly Val Asp Ala Ile Cys Thr His His
6185                6190                          6195

Pro Asp Pro Lys Ser Pro Arg Leu Asp Arg Glu Gln Leu Tyr Trp
6200                6205                          6210

Glu Leu Ser Gln Leu Thr His Asn Ile Thr Glu Leu Gly Pro Tyr
6215                6220                          6225

Ala Leu Asp Asn Asp Ser Leu Phe Val Asn Gly Phe Thr His Arg
6230                6235                          6240

Ser Ser Val Ser Thr Thr Ser Thr Pro Gly Thr Pro Thr Val Tyr
6245                6250                          6255

Leu Gly Ala Ser Lys Thr Pro Ala Ser Ile Phe Gly Pro Ser Ala
6260                6265                          6270

Ala Ser His Leu Leu Ile Leu Phe Thr Leu Asn Phe Thr Ile Thr
6275                6280                          6285

Asn Leu Arg Tyr Glu Glu Asn Met Trp Pro Gly Ser Arg Lys Phe
6290                6295                          6300

Asn Thr Thr Glu Arg Val Leu Gln Gly Leu Leu Arg Pro Leu Phe
6305                6310                          6315

Lys Asn Thr Ser Val Gly Pro Leu Tyr Ser Gly Cys Arg Leu Thr
6320                6325                          6330

Leu Leu Arg Pro Glu Lys Asp Gly Glu Ala Thr Gly Val Asp Ala
6335                6340                          6345

Ile Cys Thr His Arg Pro Asp Pro Thr Gly Pro Gly Leu Asp Arg
6350                6355                          6360

Glu Gln Leu Tyr Leu Glu Leu Ser Gln Leu Thr His Ser Ile Thr
6365                6370                          6375

Glu Leu Gly Pro Tyr Thr Leu Asp Arg Asp Ser Leu Tyr Val Asn
6380                6385                          6390

Gly Phe Thr His Arg Ser Ser Val Pro Thr Thr Ser Thr Gly Val
6395                6400                          6405

Val Ser Glu Glu Pro Phe Thr Leu Asn Phe Thr Ile Asn Asn Leu
6410                6415                          6420

Arg Tyr Met Ala Asp Met Gly Gln Pro Gly Ser Leu Lys Phe Asn
6425                6430                          6435

Ile Thr Asp Asn Val Met Gln His Leu Leu Ser Pro Leu Phe Gln
6440                6445                          6450

Arg Ser Ser Leu Gly Ala Arg Tyr Thr Gly Cys Arg Val Ile Ala
6455                6460                          6465

Leu Arg Ser Val Lys Asn Gly Ala Glu Thr Arg Val Asp Leu Leu
6470                6475                          6480

Cys Thr Tyr Leu Gln Pro Leu Ser Gly Pro Gly Leu Pro Ile Lys
6485                6490                          6495
```

-continued

Gln Val Phe His Glu Leu Ser Gln Gln Thr His Gly Ile Thr Arg
6500                5505                6510

Leu Gly Pro Tyr Ser Leu Asp Lys Asp Ser Leu Tyr Leu Asn Gly
6515                6520                6525

Tyr Asn Glu Pro Gly Pro Asp Glu Pro Pro Thr Thr Pro Lys Pro
6530                6535                6540

Ala Thr Thr Phe Leu Pro Pro Leu Ser Glu Ala Thr Thr Ala Met
6545                6550                6555

Gly Tyr His Leu Lys Thr Leu Thr Leu Asn Phe Thr Ile Ser Asn
6560                6565                6570

Leu Gln Tyr Ser Pro Asp Met Gly Lys Gly Ser Ala Thr Phe Asn
6575                6580                6585

Ser Thr Glu Gly Val Leu Gln His Leu Leu Arg Pro Leu Phe Gln
6590                6595                6600

Lys Ser Ser Met Gly Pro Phe Tyr Leu Gly Cys Gln Leu Ile Ser
6605                6610                6615

Leu Arg Pro Glu Lys Asp Gly Ala Ala Thr Gly Val Asp Thr Thr
6620                6625                6630

Cys Thr Tyr His Pro Asp Pro Val Gly Pro Gly Leu Asp Ile Gln
6635                6640                6645

Gln Leu Tyr Trp Glu Leu Ser Gln Leu Thr His Gly Val Thr Gln
6650                6655                6660

Leu Gly Phe Tyr Val Leu Asp Arg Asp Ser Leu Phe Ile Asn Gly
6665                6670                6675

Tyr Ala Pro Gln Asn Leu Ser Ile Arg Gly Glu Tyr Gln Ile Asn
6680                6685                6690

Phe His Ile Val Asn Trp Asn Leu Ser Asn Pro Asp Pro Thr Ser
6695                6700                6705

Ser Glu Tyr Ile Thr Leu Leu Arg Asp Ile Gln Asp Lys Val Thr
6710                6715                6720

Thr Leu Tyr Lys Gly Ser Gln Leu His Asp Thr Phe Arg Phe Cys
6725                6730                6735

Leu Val Thr Asn Leu Thr Met Asp Ser Val Leu Val Thr Val Lys
6740                6745                6750

Ala Leu Phe Ser Ser Asn Leu Asp Pro Ser Leu Val Glu Gln Val
6755                6760                6765

Phe Leu Asp Lys Thr Leu Asn Ala Ser Phe His Trp Leu Gly Ser
6770                6775                6780

Thr Tyr Gln Leu Val Asp Ile His Val Thr Glu Met Glu Ser Ser
6785                6790                6795

Val Tyr Gln Pro Thr Ser Ser Ser Ser Thr Gln His Phe Tyr Leu
6800                6805                6810

Asn Phe Thr Ile Thr Asn Leu Pro Tyr Ser Gln Asp Lys Ala Gln
6815                6820                6825

Pro Gly Thr Thr Asn Tyr Gln Arg Asn Lys Arg Asn Ile Glu Asp
6830                6835                6840

Ala Leu Asn Gln Leu Phe Arg Asn Ser Ser Ile Lys Ser Tyr Phe
6845                6850                6855

Ser Asp Cys Gln Val Ser Thr Phe Arg Ser Val Pro Asn Arg His
6860                6865                6870

His Thr Gly Val Asp Ser Leu Cys Asn Phe Ser Pro Leu Ala Arg
6875                6880                6885

Arg Val Asp Arg Val Ala Ile Tyr Glu Glu Phe Leu Arg Met Thr
6890                6895                6900

```
Arg  Asn  Gly  Thr  Gln  Leu  Gln  Asn  Phe  Thr  Leu  Asp  Arg  Ser  Ser
     6905                6910                     6915

Val  Leu  Val  Asp  Gly  Tyr  Ser  Pro  Asn  Arg  Asn  Glu  Pro  Leu  Thr
     6920                6925                     6930

Gly  Asn  Ser  Asp  Leu  Pro  Phe  Trp  Ala  Val  Ile  Leu  Ile  Gly  Leu
     6935                6940                     6945

Ala  Gly  Leu  Leu  Gly  Leu  Ile  Thr  Cys  Leu  Ile  Cys  Gly  Val  Leu
     6950                6955                     6960

Val  Thr  Thr  Arg  Arg  Lys  Lys  Glu  Gly  Glu  Tyr  Asn  Val  Gln
     6965                6970                     6975

Gln  Gln  Cys  Pro  Gly  Tyr  Tyr  Gln  Ser  His  Leu  Asp  Leu  Glu  Asp
     6980                6985                     6990

Leu  Gln
     6995
```

<210> SEQ ID NO 45
<211> LENGTH: 30
<212> TYPE: PRT
<213> ORGANISM: Homo sapiens

<400> SEQUENCE: 45

```
Gly  His  Thr  Ala  Pro  Gly  Pro  Leu  Leu  Val  Pro  Phe  Thr  Leu  Asn  Phe
1                 5                        10                       15

Thr  Ile  Thr  Asn  Leu  Arg  Tyr  Glu  Glu  Asn  Met  Arg  His  Pro
              20                        25                       30
```

<210> SEQ ID NO 46
<211> LENGTH: 7
<212> TYPE: PRT
<213> ORGANISM: Homo sapiens

<400> SEQUENCE: 46

```
Ala  Pro  Val  Pro  Leu  Leu  Ile
1                 5
```

<210> SEQ ID NO 47
<211> LENGTH: 7
<212> TYPE: PRT
<213> ORGANISM: Homo sapiens

<400> SEQUENCE: 47

```
Ala  Pro  Gly  Pro  Leu  Leu  Val
1                 5
```

<210> SEQ ID NO 48
<211> LENGTH: 6
<212> TYPE: PRT
<213> ORGANISM: Homo sapiens

<400> SEQUENCE: 48

```
Ala  Ser  Pro  Leu  Leu  Val
1                 5
```

<210> SEQ ID NO 49
<211> LENGTH: 5
<212> TYPE: PRT
<213> ORGANISM: Homo sapiens

<400> SEQUENCE: 49

```
Gly  Pro  Leu  Leu  Val
1                 5
```

```
-continued

<210> SEQ ID NO 50
<211> LENGTH: 4
<212> TYPE: PRT
<213> ORGANISM: Homo sapiens

<400> SEQUENCE: 50

Pro Leu Leu Val
1

<210> SEQ ID NO 51
<211> LENGTH: 10
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa indicates Pro or Leu

<400> SEQUENCE: 51

Xaa Phe Thr Leu Asn Phe Thr Ile Thr Asn
1               5                   10
```